(12) United States Patent
Sachs et al.

(10) Patent No.: US 12,168,130 B2
(45) Date of Patent: *Dec. 17, 2024

(54) SYSTEMS AND METHODS FOR RESTORING MUSCLE FUNCTION TO THE LUMBAR SPINE

(71) Applicant: Mainstay Medical Limited, County Dublin (IE)

(72) Inventors: Dan Sachs, Minneapolis, MN (US); Prashant Brijmohansingh Rawat, Blaine, MN (US); Jason Shiroff, Edina, MN (US); Peter Crosby, Blaine, MN (US)

(73) Assignee: Mainstay Medical Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/333,474

(22) Filed: Jun. 12, 2023

(65) Prior Publication Data

US 2023/0321439 A1    Oct. 12, 2023

Related U.S. Application Data

(63) Continuation of application No. 17/812,989, filed on Jul. 15, 2022, now Pat. No. 11,679,262, which is a (Continued)

(51) Int. Cl.
*A61N 1/18* (2006.01)
*A61N 1/05* (2006.01)
(Continued)

(52) U.S. Cl.
CPC ....... *A61N 1/36071* (2013.01); *A61N 1/0551* (2013.01); *A61N 1/0558* (2013.01);
(Continued)

(58) Field of Classification Search
CPC .............. A61N 1/3604; A61N 1/36062; A61N 1/36071; A61N 1/36103
See application file for complete search history.

(56) References Cited

U.S. PATENT DOCUMENTS

| 1,526,595 A | 2/1925 | George et al. |
| 3,077,884 A | 2/1963 | John et al. |
| (Continued) | | |

FOREIGN PATENT DOCUMENTS

| CN | 1211930 A | 3/1999 |
| CN | 1211930 C | 7/2005 |
| (Continued) | | |

OTHER PUBLICATIONS

Airaksinen, et al., Chapter 4. European guidelines for the management of chronic nonspecific low back pain, European spine journal [I: official publication of the European Spine Society, the European Spinal Deformity Society, and the European Section of the Cervical Spine Research Society 15 Suppl 2:S192-300 (2006), http://www.ncbi.nlm.nih.gov/pubmed/16550448.
(Continued)

*Primary Examiner* — Allen Porter
(74) *Attorney, Agent, or Firm* — Greenberg Traurig, LLP; Christopher C. Bolten; Albert K. Heng

(57) ABSTRACT

A system for restoring muscle function to the lumbar spine to treat low back pain is provided. The system may include electrodes coupled to an implantable pulse generator (IPG), a handheld activator configured to transfer a stimulation command to the IPG, and an external programmer configured to transfer programming data to the IPG. The stimulation command directs the programmable controller to stimulate the tissue in accordance with the programming data. The system may include a software-based program-
(Continued)

ming system run on a computer such that the treating physician may program and adjust stimulation parameters.

30 Claims, 24 Drawing Sheets

Related U.S. Application Data continuation of application No. 17/092,073, filed on Nov. 6, 2020, which is a continuation-in-part of application No. 16/817,574, filed on Mar. 12, 2020, now Pat. No. 10,926,083, and a continuation of application No. 15/944,730, filed on Apr. 3, 2018, now Pat. No. 10,828,490, said application No. 16/817,574 is a continuation of application No. 15/853,543, filed on Dec. 22, 2017, now Pat. No. 10,661,078, said application No. 15/944,730 is a continuation of application No. 15/299,399, filed on Oct. 20, 2016, now Pat. No. 10,016,603, said application No. 15/853,543 is a continuation of application No. 14/849,478, filed on Sep. 9, 2015, now Pat. No. 9,861,811, said application No. 15/299,399 is a continuation of application No. 14/792,430, filed on Jul. 6, 2015, now Pat. No. 9,474,906, which is a continuation of application No. 14/061,614, filed on Oct. 23, 2013, now Pat. No. 9,072,897, which is a continuation-in-part of application No. 13/858,809, filed on Apr. 8, 2013, now Pat. No. 8,606,358, said application No. 14/849,478 is a continuation of application No. 13/045,421, filed on Mar. 10, 2011, now Pat. No. 9,248,278, said application No. 13/858,809 is a continuation of application No. 12/075,174, filed on Mar. 10, 2008, now Pat. No. 8,428,728.

(60) Provisional application No. 61/339,957, filed on Mar. 11, 2010, provisional application No. 60/905,979, filed on Mar. 9, 2007.

(51) Int. Cl.
*A61N 1/36* (2006.01)
*A61N 1/372* (2006.01)
*A61N 2/00* (2006.01)
*A61N 2/06* (2006.01)

(52) U.S. Cl.
CPC ..... *A61N 1/36003* (2013.01); *A61N 1/36067* (2013.01); *A61N 1/36125* (2013.01); *A61N 1/36146* (2013.01); *A61N 1/36167* (2013.01); *A61N 1/36175* (2013.01); *A61N 1/36185* (2013.01); *A61N 1/37229* (2013.01); *A61N 1/37247* (2013.01); *A61N 2/008* (2013.01); *A61N 2/06* (2013.01); *A61N 1/36157* (2013.01)

(56) References Cited

U.S. PATENT DOCUMENTS

| | | | |
|---|---|---|---|
| 3,416,534 A | 12/1968 | Quinn |
| 3,710,777 A | 1/1973 | Sparks |
| 3,754,555 A | 8/1973 | Schmitt |
| 3,875,947 A | 4/1975 | Jula et al. |
| 3,893,463 A | 7/1975 | Williams |
| 3,902,501 A | 9/1975 | Citron et al. |
| 3,976,082 A | 8/1976 | Schmitt |
| 3,999,551 A | 12/1976 | Spitz et al. |
| 4,010,757 A | 3/1977 | Jula et al. |
| 4,026,301 A | 5/1977 | Friedman et al. |
| 4,031,899 A | 6/1977 | Renirie |
| 4,149,528 A | 4/1979 | Murphy |
| 4,235,246 A | 11/1980 | Weiss |
| 4,269,198 A | 5/1981 | Stokes |
| 4,342,317 A | 8/1982 | Axelgaard |
| 4,408,609 A | 10/1983 | Axelgaard |
| 4,418,693 A | 12/1983 | LeVeen et al. |
| 4,471,777 A | 9/1984 | McCorkle, Jr. |
| 4,528,984 A | 7/1985 | Morawetz et al. |
| 4,549,556 A | 10/1985 | Tarjan et al. |
| 4,574,806 A | 3/1986 | McCarthy |
| 4,608,986 A | 9/1986 | Beranek et al. |
| 4,658,835 A | 4/1987 | Pohndorf |
| 4,832,687 A | 5/1989 | Smith, III |
| 4,917,093 A | 4/1990 | Dufresne et al. |
| 5,069,680 A | 12/1991 | Grandjean |
| 5,199,430 A | 4/1993 | Fang et al. |
| 5,215,088 A | 6/1993 | Normann et al. |
| 5,273,053 A | 12/1993 | Pohndorf |
| 5,300,108 A | 4/1994 | Rebell et al. |
| 5,330,515 A | 7/1994 | Rutecki et al. |
| 5,376,108 A | 12/1994 | Collins et al. |
| 5,496,345 A | 3/1996 | Kieturakis et al. |
| 5,501,452 A | 3/1996 | Halvorson |
| 5,507,788 A | 4/1996 | Lieber |
| 5,522,854 A | 6/1996 | Ideker et al. |
| 5,569,183 A | 10/1996 | Kieturakis |
| 5,575,797 A | 11/1996 | Neubauer et al. |
| 5,638,825 A | 6/1997 | Yamazaki et al. |
| 5,651,781 A | 7/1997 | Grace |
| 5,733,307 A | 3/1998 | Dinsdale |
| 5,741,321 A | 4/1998 | Brennen |
| 5,760,341 A | 6/1998 | Laske et al. |
| 5,782,841 A | 7/1998 | Ritz et al. |
| 5,807,234 A | 9/1998 | Bui et al. |
| 5,873,900 A | 2/1999 | Maurer et al. |
| 5,897,584 A | 4/1999 | Herman |
| 5,916,172 A | 6/1999 | Hodges et al. |
| 5,957,968 A | 9/1999 | Belden et al. |
| 5,980,515 A | 11/1999 | Tu |
| 6,104,957 A | 8/2000 | Alo et al. |
| 6,119,516 A | 9/2000 | Hock |
| 6,314,325 B1 | 11/2001 | Fitz |
| 6,319,241 B1 | 11/2001 | King et al. |
| 6,324,414 B1 | 11/2001 | Gibbons et al. |
| 6,366,819 B1 | 4/2002 | Stokes |
| 6,381,496 B1 | 4/2002 | Meadows et al. |
| 6,406,421 B1 | 6/2002 | Grandjean et al. |
| 6,451,036 B1 | 9/2002 | Heitzmann et al. |
| 6,473,654 B1 | 10/2002 | Chinn |
| 6,516,227 B1 | 2/2003 | Meadows et al. |
| 6,527,787 B1 | 3/2003 | Fogarty et al. |
| 6,565,594 B1 | 5/2003 | Herweck et al. |
| 6,600,954 B2 | 7/2003 | Cohen et al. |
| 6,600,956 B2 | 7/2003 | Maschino et al. |
| 6,605,094 B1 | 8/2003 | Mann et al. |
| 6,671,557 B1 | 12/2003 | Gliner |
| 6,735,474 B1 | 5/2004 | Loeb et al. |
| 6,839,594 B2 | 1/2005 | Cohen et al. |
| 6,845,271 B2 | 1/2005 | Fang et al. |
| 6,862,479 B1 | 3/2005 | Whitehurst et al. |
| 6,971,393 B1 | 12/2005 | Mamo et al. |
| 7,018,384 B2 | 3/2006 | Skakoon |
| 7,096,070 B1 | 8/2006 | Jenkins et al. |
| 7,206,641 B2 | 4/2007 | Ignagni et al. |
| 7,218,970 B2 | 5/2007 | Ley et al. |
| 7,239,918 B2 | 7/2007 | Strother et al. |
| 7,286,879 B2 | 10/2007 | Wallace |
| 7,317,948 B1 | 1/2008 | King et al. |
| 7,324,852 B2 | 1/2008 | Barolat et al. |
| 7,324,853 B2 | 1/2008 | Ayal et al. |
| 7,337,005 B2 | 2/2008 | Kim et al. |
| 7,337,006 B2 | 2/2008 | Kim et al. |
| 7,369,894 B2 | 5/2008 | Gerber |
| 7,389,149 B2 | 6/2008 | Rossing et al. |
| 7,444,181 B2 | 10/2008 | Shi et al. |
| 7,447,546 B2 | 11/2008 | Kim et al. |
| 7,450,993 B2 | 11/2008 | Kim et al. |
| 7,489,561 B2 | 2/2009 | Armstrong et al. |
| 7,493,175 B2 | 2/2009 | Cates et al. |

(56) References Cited

U.S. PATENT DOCUMENTS

| | | |
|---|---|---|
| 7,499,746 B2 | 3/2009 | Buhlmann et al. |
| 7,502,651 B2 | 3/2009 | Kim et al. |
| 7,515,971 B1 | 4/2009 | Doan |
| 7,553,313 B2 | 6/2009 | Bagby |
| 7,580,753 B2 | 8/2009 | Kim et al. |
| 7,668,598 B2 | 2/2010 | Herregraven et al. |
| 7,684,866 B2 | 3/2010 | Fowler et al. |
| 7,708,763 B2 | 5/2010 | Selover et al. |
| 7,761,166 B2 | 7/2010 | Giftakis et al. |
| 7,792,591 B2 | 9/2010 | Rooney et al. |
| 7,797,053 B2 | 9/2010 | Atkinson et al. |
| 7,813,803 B2 | 10/2010 | Heruth et al. |
| 7,908,015 B2 | 3/2011 | Lazeroms et al. |
| 7,917,230 B2 | 3/2011 | Bly |
| 7,930,039 B2 | 4/2011 | Olson |
| 7,981,144 B2 | 7/2011 | Geist et al. |
| 8,016,846 B2 | 9/2011 | McFarlin et al. |
| 8,065,020 B2 | 11/2011 | Ley et al. |
| 8,082,039 B2 | 12/2011 | Kim et al. |
| 8,170,690 B2 | 5/2012 | Morgan et al. |
| 8,229,565 B2 | 7/2012 | Kim et al. |
| 8,229,656 B2 | 7/2012 | Ikushima et al. |
| 8,249,701 B2 | 8/2012 | Imran et al. |
| 8,249,713 B2 | 8/2012 | Fang et al. |
| 8,321,021 B2 | 11/2012 | Kisker et al. |
| 8,380,318 B2 | 2/2013 | Kishawi et al. |
| 8,386,045 B2 | 2/2013 | Zhao et al. |
| 8,391,966 B2 | 3/2013 | Luo et al. |
| 8,409,233 B1 | 4/2013 | Chinn et al. |
| 8,428,728 B2 | 4/2013 | Sachs |
| 8,463,383 B2 | 6/2013 | Sakai et al. |
| 8,498,697 B2 | 7/2013 | Yong et al. |
| 8,606,358 B2 | 12/2013 | Sachs |
| 8,798,005 B1 | 8/2014 | Vargantwar et al. |
| 8,886,337 B2 | 11/2014 | Bennett et al. |
| 8,965,516 B2 | 2/2015 | Bennett et al. |
| 9,072,897 B2 | 7/2015 | Sachs et al. |
| 9,079,019 B2 | 7/2015 | Crosby et al. |
| 9,108,053 B2 | 8/2015 | Crosby et al. |
| 9,186,501 B2 | 11/2015 | Rawat et al. |
| 9,248,278 B2 | 2/2016 | Crosby et al. |
| 9,320,847 B2 | 4/2016 | Rooney et al. |
| 9,339,269 B2 | 5/2016 | Geistert |
| 9,474,906 B2 | 10/2016 | Sachs et al. |
| 9,561,364 B2 | 2/2017 | Bondhus et al. |
| 9,586,041 B2 | 3/2017 | Goode et al. |
| 9,649,490 B2 | 5/2017 | Booker |
| 9,861,811 B2 | 1/2018 | Crosby et al. |
| 9,889,294 B2 | 2/2018 | Kalmann et al. |
| 9,950,159 B2 | 4/2018 | Beck et al. |
| 9,981,122 B2 | 5/2018 | Rawat et al. |
| 9,999,763 B2 | 6/2018 | Shiroff et al. |
| 10,016,603 B2 | 7/2018 | Sachs et al. |
| 10,195,419 B2 | 2/2019 | Shiroff et al. |
| 10,327,810 B2 | 6/2019 | Shiroff et al. |
| 10,448,999 B2 | 10/2019 | Schneider |
| 10,449,355 B2 | 10/2019 | Beck et al. |
| 10,471,268 B2 | 11/2019 | Crosby et al. |
| 10,653,440 B2 | 5/2020 | Goode et al. |
| 10,661,078 B2 | 5/2020 | Crosby et al. |
| 10,729,415 B2 | 8/2020 | Roeder et al. |
| 10,828,490 B2 | 11/2020 | Sachs et al. |
| 11,103,706 B2 | 8/2021 | Sachs et al. |
| 11,331,488 B2 | 5/2022 | Sachs et al. |
| 11,376,427 B2 | 7/2022 | Beck et al. |
| 11,406,421 B2 | 8/2022 | Shiroff et al. |
| 11,471,670 B2 * | 10/2022 | Crosby ............ A61N 1/36071 |
| 11,679,261 B2 * | 6/2023 | Sachs ............... A61N 1/36071 607/46 |
| 11,679,262 B2 | 6/2023 | Sachs et al. |
| 11,684,774 B2 * | 6/2023 | Crosby ............ A61N 1/36003 606/41 |
| 11,937,847 B2 | 3/2024 | Shiroff et al. |
| 11,951,310 B2 * | 4/2024 | Sachs ............... A61N 1/37229 |
| 12,048,844 B2 | 7/2024 | Crosby et al. |
| 2001/0053885 A1 | 12/2001 | Gielen et al. |
| 2002/0065543 A1 | 5/2002 | Gomperz et al. |
| 2002/0068960 A1 | 6/2002 | Saberski et al. |
| 2002/0099419 A1 | 7/2002 | Cohen et al. |
| 2002/0115945 A1 | 8/2002 | Herman et al. |
| 2002/0147485 A1 | 10/2002 | Mamo et al. |
| 2002/0156513 A1 | 10/2002 | Borkan |
| 2002/0161415 A1 | 10/2002 | Cohen et al. |
| 2002/0183765 A1 | 12/2002 | Adams |
| 2003/0100933 A1 | 5/2003 | Ayal et al. |
| 2003/0120323 A1 | 6/2003 | Meadows et al. |
| 2003/0120328 A1 | 6/2003 | Jenkins et al. |
| 2003/0135120 A1 | 7/2003 | Parks et al. |
| 2003/0199938 A1 | 10/2003 | Smits et al. |
| 2003/0204228 A1 * | 10/2003 | Cross, Jr. ............ A61N 1/0553 607/116 |
| 2004/0030360 A1 | 2/2004 | Eini et al. |
| 2004/0097986 A1 | 5/2004 | Adams |
| 2004/0111118 A1 | 6/2004 | Hill et al. |
| 2004/0122482 A1 | 6/2004 | Tung et al. |
| 2004/0147969 A1 | 7/2004 | Mann et al. |
| 2004/0167580 A1 | 8/2004 | Mann et al. |
| 2004/0214790 A1 | 10/2004 | Borgens |
| 2004/0230281 A1 | 11/2004 | Heil et al. |
| 2004/0236383 A1 | 11/2004 | Yelizarov |
| 2005/0070971 A1 | 3/2005 | Fowler et al. |
| 2005/0075701 A1 | 4/2005 | Shafer |
| 2005/0080472 A1 | 4/2005 | Atkinson et al. |
| 2005/0107861 A1 | 5/2005 | Harris et al. |
| 2005/0119713 A1 | 6/2005 | Whitehurst et al. |
| 2005/0137644 A1 | 6/2005 | Boveja et al. |
| 2005/0149154 A1 | 7/2005 | Cohen et al. |
| 2005/0154389 A1 | 7/2005 | Selover et al. |
| 2005/0165456 A1 | 7/2005 | Mann et al. |
| 2005/0177211 A1 | 8/2005 | Leung et al. |
| 2005/0240243 A1 | 10/2005 | Barolat et al. |
| 2005/0246006 A1 | 11/2005 | Daniels |
| 2005/0283204 A1 | 12/2005 | Buhlmann et al. |
| 2005/0288730 A1 | 12/2005 | Deem et al. |
| 2006/0004429 A1 | 1/2006 | Mrva et al. |
| 2006/0009810 A1 | 1/2006 | Mann et al. |
| 2006/0009827 A1 | 1/2006 | Kurth et al. |
| 2006/0032657 A1 | 2/2006 | Zarembo |
| 2006/0052856 A1 | 3/2006 | Kim et al. |
| 2006/0106416 A1 | 5/2006 | Raymond et al. |
| 2006/0111746 A1 | 5/2006 | Foreman et al. |
| 2006/0111754 A1 | 5/2006 | Rezai et al. |
| 2006/0155341 A1 | 7/2006 | Tehrani et al. |
| 2006/0184222 A1 | 8/2006 | Camps et al. |
| 2006/0206166 A1 | 9/2006 | Weiner |
| 2006/0235484 A1 | 10/2006 | Jaax et al. |
| 2006/0241716 A1 | 10/2006 | Finch et al. |
| 2006/0259074 A1 | 11/2006 | Kelleher et al. |
| 2006/0293662 A1 | 12/2006 | Boyer et al. |
| 2007/0027501 A1 | 2/2007 | Jensen et al. |
| 2007/0049980 A1 | 3/2007 | Zielinski et al. |
| 2007/0060967 A1 | 3/2007 | Strother et al. |
| 2007/0073357 A1 | 3/2007 | Rooney et al. |
| 2007/0100377 A1 | 5/2007 | Armstrong et al. |
| 2007/0100391 A1 | 5/2007 | Armstrong |
| 2007/0100408 A1 | 5/2007 | Gerber |
| 2007/0100411 A1 | 5/2007 | Bonde |
| 2007/0123954 A1 | 5/2007 | Gielen et al. |
| 2007/0129780 A1 | 6/2007 | Whitehurst et al. |
| 2007/0135768 A1 | 6/2007 | Carlsen |
| 2007/0179557 A1 | 8/2007 | Maschino et al. |
| 2007/0208392 A1 | 9/2007 | Kuschner et al. |
| 2007/0232936 A1 | 10/2007 | Mann et al. |
| 2007/0239224 A1 | 10/2007 | Bennett et al. |
| 2007/0276453 A1 | 11/2007 | Hill et al. |
| 2008/0026981 A1 | 1/2008 | Muhrer et al. |
| 2008/0027505 A1 | 1/2008 | Levin et al. |
| 2008/0103570 A1 | 5/2008 | Gerber |
| 2008/0103573 A1 | 5/2008 | Gerber |
| 2008/0103574 A1 | 5/2008 | Gerber |
| 2008/0103579 A1 | 5/2008 | Gerber |
| 2008/0132961 A1 | 6/2008 | Jaax et al. |
| 2008/0132969 A1 | 6/2008 | Bennett et al. |
| 2008/0147156 A1 | 6/2008 | Imran |

(56) References Cited

U.S. PATENT DOCUMENTS

| | | |
|---|---|---|
| 2008/0167698 A1 | 7/2008 | Kim et al. |
| 2008/0177351 A1 | 7/2008 | Fang et al. |
| 2008/0183221 A1 | 7/2008 | Burdulis |
| 2008/0183257 A1 | 7/2008 | Imran et al. |
| 2008/0200972 A1 | 8/2008 | Rittman et al. |
| 2008/0228241 A1 | 9/2008 | Sachs |
| 2008/0234791 A1 | 9/2008 | Arle et al. |
| 2008/0269716 A1 | 10/2008 | Bonde et al. |
| 2008/0269812 A1 | 10/2008 | Gerber et al. |
| 2009/0005833 A1 | 1/2009 | Cameron et al. |
| 2009/0018576 A1 | 1/2009 | Binmoeller |
| 2009/0020764 A1 | 1/2009 | Anderson et al. |
| 2009/0105700 A1 | 4/2009 | Anderson |
| 2009/0112263 A1 | 4/2009 | Pool et al. |
| 2009/0192567 A1 | 7/2009 | Armstrong et al. |
| 2009/0210041 A1 | 8/2009 | Kim et al. |
| 2009/0248095 A1 | 10/2009 | Schleicher et al. |
| 2009/0254095 A1 | 10/2009 | Levine et al. |
| 2009/0259280 A1 | 10/2009 | Wilkin et al. |
| 2009/0299201 A1 | 12/2009 | Gunderson |
| 2009/0299444 A1 | 12/2009 | Boling |
| 2009/0326613 A1 | 12/2009 | Knoblich |
| 2010/0030227 A1 | 2/2010 | Kast et al. |
| 2010/0036280 A1 | 2/2010 | Ballegaard et al. |
| 2010/0036454 A1 | 2/2010 | Bennett et al. |
| 2010/0082086 A1 | 4/2010 | Zhu |
| 2010/0114206 A1 | 5/2010 | Kaemmerer et al. |
| 2010/0137938 A1 | 6/2010 | Kishawi et al. |
| 2010/0152808 A1 | 6/2010 | Boggs, II |
| 2010/0152809 A1 | 6/2010 | Boggs, II |
| 2010/0174240 A1 | 7/2010 | Wells et al. |
| 2010/0174326 A1 | 7/2010 | Selover et al. |
| 2010/0179562 A1 | 7/2010 | Linker et al. |
| 2010/0185161 A1 | 7/2010 | Pellegrino et al. |
| 2010/0211149 A1 | 8/2010 | Morgan et al. |
| 2010/0249875 A1 | 9/2010 | Kishawi et al. |
| 2010/0280576 A1 | 11/2010 | Gerber et al. |
| 2010/0292769 A1 | 11/2010 | Brounstein et al. |
| 2010/0331883 A1 | 12/2010 | Schmitz et al. |
| 2011/0004269 A1 | 1/2011 | Strother et al. |
| 2011/0021943 A1 | 1/2011 | Lacour et al. |
| 2011/0022114 A1 | 1/2011 | Navarro |
| 2011/0022123 A1 | 1/2011 | Stancer et al. |
| 2011/0054565 A1 | 3/2011 | Wacnik et al. |
| 2011/0106207 A1 | 5/2011 | Cauller et al. |
| 2011/0160538 A1 | 6/2011 | Ravikumar et al. |
| 2011/0190786 A1 | 8/2011 | Gerber et al. |
| 2011/0202112 A1 | 8/2011 | Ruais |
| 2011/0224665 A1 | 9/2011 | Crosby et al. |
| 2011/0224682 A1 | 9/2011 | Westlund et al. |
| 2011/0251662 A1 | 10/2011 | Griswold et al. |
| 2011/0257660 A1 | 10/2011 | Jones et al. |
| 2011/0270340 A1 | 11/2011 | Pellegrini et al. |
| 2012/0035953 A1 | 2/2012 | Armstrong |
| 2012/0089153 A1 | 4/2012 | Christopherson et al. |
| 2012/0116477 A1 | 5/2012 | Crowe et al. |
| 2012/0192874 A1 | 8/2012 | Bolea et al. |
| 2012/0209285 A1 | 8/2012 | Barker et al. |
| 2012/0215218 A1 | 8/2012 | Lipani |
| 2012/0283800 A1 | 11/2012 | Perryman et al. |
| 2012/0290055 A1 | 11/2012 | Boggs, II |
| 2012/0310140 A1 | 12/2012 | Kramer et al. |
| 2012/0310301 A1 | 12/2012 | Bennett et al. |
| 2012/0310302 A1 | 12/2012 | Bennett et al. |
| 2012/0310314 A1 | 12/2012 | Bennett et al. |
| 2012/0323253 A1 | 12/2012 | Garai et al. |
| 2013/0023974 A1 | 1/2013 | Amrani |
| 2013/0053926 A1 | 2/2013 | Hincapie Ordonez et al. |
| 2013/0096641 A1 | 4/2013 | Strother et al. |
| 2013/0106347 A1 | 5/2013 | Kallmyer et al. |
| 2013/0131766 A1 | 5/2013 | Crosby et al. |
| 2013/0155117 A1 | 6/2013 | Bang |
| 2013/0197607 A1 | 8/2013 | Wilder et al. |
| 2013/0197615 A1 | 8/2013 | Rundle et al. |
| 2013/0211487 A1 | 8/2013 | Fang et al. |
| 2013/0218247 A1 | 8/2013 | Sachs |
| 2013/0238066 A1 | 9/2013 | Boggs, II et al. |
| 2013/0245715 A1 | 9/2013 | Peterson |
| 2013/0253605 A1 | 9/2013 | Bennett et al. |
| 2013/0261696 A1 | 10/2013 | Thacker et al. |
| 2013/0296966 A1 | 11/2013 | Wongsarnpigoon et al. |
| 2013/0310901 A1 | 11/2013 | Perryman et al. |
| 2013/0338730 A1 | 12/2013 | Shiroff et al. |
| 2014/0029695 A1 | 1/2014 | Liu et al. |
| 2014/0031837 A1 | 1/2014 | Perryman et al. |
| 2014/0039574 A1 | 2/2014 | Bradley |
| 2014/0046398 A1 | 2/2014 | Sachs et al. |
| 2014/0058476 A1 | 2/2014 | Crosby et al. |
| 2014/0114385 A1 | 4/2014 | Nijhuis et al. |
| 2014/0288616 A1 | 9/2014 | Rawat et al. |
| 2014/0350653 A1 | 11/2014 | Shiroff et al. |
| 2015/0101188 A1 | 4/2015 | Klardie et al. |
| 2015/0105840 A1 | 4/2015 | Boggs, II |
| 2015/0306405 A1 | 10/2015 | Sachs et al. |
| 2015/0374992 A1 | 12/2015 | Crosby et al. |
| 2016/0045746 A1 | 2/2016 | Jiang et al. |
| 2016/0045747 A1 | 2/2016 | Jiang et al. |
| 2016/0067476 A1 | 3/2016 | Rawat et al. |
| 2016/0106994 A1 | 4/2016 | Crosby et al. |
| 2016/0213927 A1 | 7/2016 | McGee et al. |
| 2016/0310732 A1 | 10/2016 | Beck et al. |
| 2017/0100408 A1 | 4/2017 | Bertolini |
| 2018/0008311 A1 | 1/2018 | Shiroff et al. |
| 2018/0133461 A1 | 5/2018 | Crosby et al. |
| 2018/0256906 A1 | 9/2018 | Pivonka et al. |
| 2018/0353757 A1 | 12/2018 | Sachs et al. |
| 2019/0167995 A1 | 6/2019 | Sachs et al. |
| 2019/0328423 A1 | 10/2019 | Shiroff et al. |
| 2020/0203858 A1 | 6/2020 | Youtsey |

FOREIGN PATENT DOCUMENTS

| | | |
|---|---|---|
| CN | 101678203 A | 3/2010 |
| EP | 0587269 A2 | 3/1994 |
| EP | 0587269 B1 | 12/1998 |
| EP | 1053762 A2 | 11/2000 |
| EP | 1255583 A1 | 11/2002 |
| EP | 1053762 B1 | 8/2005 |
| EP | 1255583 B1 | 12/2007 |
| EP | 2125100 A1 | 12/2009 |
| EP | 2273931 A2 | 1/2011 |
| WO | WO-0158520 A1 | 8/2001 |
| WO | WO-2004066820 A2 | 8/2004 |
| WO | WO-2006091611 A1 | 8/2006 |
| WO | WO-2006133445 A2 | 12/2006 |
| WO | WO-2006135791 A2 | 12/2006 |
| WO | WO-2007047954 A2 | 4/2007 |
| WO | WO-2007051146 A1 | 5/2007 |
| WO | WO-2007138598 A2 | 12/2007 |
| WO | WO-2008048471 A2 | 4/2008 |
| WO | WO-2008070807 A2 | 6/2008 |
| WO | WO-2008094952 A2 | 8/2008 |
| WO | WO-2008112178 A1 | 9/2008 |
| WO | WO-2009020764 A1 | 2/2009 |
| WO | WO-2009134475 A1 | 11/2009 |
| WO | WO-2010062600 A1 | 6/2010 |
| WO | WO-2010062622 A2 | 6/2010 |
| WO | WO-2011079866 A1 | 7/2011 |
| WO | WO-2011112773 A2 | 9/2011 |
| WO | WO-2012057916 A1 | 5/2012 |
| WO | WO-2012091747 A1 | 7/2012 |
| WO | WO-2013016268 A1 | 1/2013 |
| WO | WO-2013019853 A1 | 2/2013 |
| WO | WO-2013036630 A1 | 3/2013 |
| WO | WO-2013096260 A1 | 6/2013 |
| WO | WO-2013138786 A1 | 9/2013 |
| WO | WO-2013155117 A1 | 10/2013 |
| WO | WO-2014099423 A1 | 6/2014 |
| WO | WO-2015059570 A1 | 4/2015 |
| WO | WO-2015187426 A1 | 12/2015 |
| WO | WO-2017044904 A1 | 3/2017 |
| WO | WO-2017062508 A1 | 4/2017 |
| WO | WO-2018007914 A1 | 1/2018 |

(56) References Cited

FOREIGN PATENT DOCUMENTS

OTHER PUBLICATIONS

Baker, et al., Clinical Uses of Neuromuscular Electrical Stimulation, NeuroMuscular Electrical Stimulation—A Practical Guide, 4th ed., Rancho Los Amigos Research and Education Institute Inc (pp. 47-66) (2000).
Bhadra, et al., Peripheral nerve stimulation for restoration of motor function, Journal of Clinical Neurophysiology: Official Publication of the American Electroencephalographic Society, 14(5):378-33 (Sep. 1997).
Bogie, et al., Effects of Regular Use of Neuromuscular Electrical Stimulation on Tissue Health, Journal of Rehabilitation Research and Development, 40(6):469-475 (2003) available at: http://www.ncbi.nlm.nih.gov/pubmed/15077659 (Accessed Jan. 18, 2011).
Bowman, et al., Effects of Waveform Parameters on Comfort during Transcutaneous Neuromuscular Electrical Stimulation, Annals of Biomedical Engineering, 13:59-74 (1985).
Bradford, et al., Surface Electrical Stimulation in the Treatment of Idiopathic Scoliosis: Preliminary Results in 30 Patients, Spine, 8(7):757-764 (1983).
Brazier, et al., A Comparison of the EQ-5D and SF-6D Across Seven Patient Groups, Health Economics, 13:873-884 (2004).
Chou et al., "Interventional Therapies, Surgery, and Interdisciplinary Rehabilitation for Low Back Pain: An Evidence-Based Clinical Practice Guideline From the American Pain Society." Spine, 34(10):1066-1077 (2009).
Coghlan, et al., Electrical Muscle Stimulation for Deep Stabilizing Muscles in Abdominal Wall, Conference proceedings: Annual International Conference of the IEEE Engineering in Medicine and Biology Society, IEEE Engineering in Medicine and Biology Society, Conference, 2008 (pp. 2756-2759)available at: http://www.ncbi.nlm.nih.gov/pubmed/19163276.
Coghlan, et al., Neuromuscular Electrical Stimulation Training Results in Enhanced Activation of Spinal Stabilizing Muscles During Spinal Loading and Improvements in Pain Ratings, Conference proceedings: Annual International Conference of the IEEE Engineering in Medicine and Biology Society, IEEE Engineering in Medicine and Biology Society, Conference, 2011 (pp. 7622-7625) available at: http://www.ncbi.nlm.nih.gov/pubmed/22256103.
Costa et al., Motor Control Exercise for Chronic Low Back Pain: A Randomized Placebo-Controlled Trial, Physical Therapy, 89(12):1275-1286 (2009).
Crago, et al., The Choice of Pulse Duration for Chronic Electrical Stimulation Via Surface, Nerve, and Intramuscular Electrodes, Annals of Biomedical Engineering, 2(3):252-264 (1974).
Criterion Inc., NMES Treatment Protocols, 3 pages (accessed Jun. 7, 2012) available at http://www.criterionmed.com/PDF/NMES%20Treatment%20Protocols.pdf.
Deckers, et al., Chronic Low Back Pain: Restoration of Dynamic Stability, Neuromodulation, 18:478-486 (2015).
Durham, et al., Surface Electrical Stimulation Versus Brace in Treatment of Idiopathic Scoliosis, Spine, 15(9):888-891 (1990).
Dworkin et al., Interpreting the Clinical Importance of Treatment Outcomes in Chronic Pain Clinical Trials: IMMPACT Recommendations, The Journal of Pain, 9(2):105-121 (2008).
Eldabe et al., "Complications of Spinal Cord Stimulation and Peripheral Nerve Stimulation Techniques: A Review of the Literature." Pain Medicine, 17:325-336 (2016).
EMPI, Low Back Syndrome/Chronic Low Back Pain, NMES Guidelines for Treatment, 2 pages (2003).
Extended European Search Report dated Jan. 7, 2013 in EP Patent Appl. Serial No. 12176863 (0231).
Extended European Search Report dated Feb. 24, 2020 in EP Patent Appl. Serial No. 08726632.6 (0230).
Extended European Search Report dated Mar. 5, 2015 in EP Patent Appl. Serial No. 14189412.1 (0830).
Extended European Search Report dated Sep. 30, 2019 in EP Patent Appl. Serial No. 19173003.5 (0840).
Farrar et al., "Use of the Cumulative Proportion of Responders Analysis Graph to Present Pain Data Over Range of Cut-Off Points: Making Clinical Trial Data More Understandable." J Pain Symptom Manage, 31(4):369-377 (2006).
Federov et al., "Consequences of dichotomization." Pharmaceut. Statist., 8:50-61 (2009).
Ferreira, et al., Comparison of general exercise, motor control exercise and spinal manipulative therapy for chronic low back pain: A randomized trial, Pain, 131(1-2):31-37 (2007) available at: http://www.ncbi.nlm.nih.gov/pubmed/17250965.
Follett, et al., Prevention and Management of Intrathecal Drug Delivery and Spinal Cord Stimulation System Infections, Anesthesiology, 100:1582-94 (2004).
Freeman, et al., The Role of the Lumbar Multifidus in Chronic Low Back Pain: A Review, American Academy of Physical Medicine and Rehabilitation, 2:142-146 (2010).
Friedman, et al., Electrical stimulation for scoliosis, American Family Physician, 25(4):155-160 (1982) available at: http://www.ncbi.nlm.nih.gov/pubmed/6978055 (Accessed Oct. 19, 2011).
Garmirian, et al., Discriminating Neurogenic from Myopathic Disease via Measurement of Muscle Anisotrophy, Muscle Nerve, 39(1):16-24 (2009) (abstract).
Gazelle, et al., Tumor Ablation with Radio-frequency Energy, Radiology, 217(3):633-646 (2000).
Ghamkhar, et al., *Application of rehabilitative ultrasound in the assessment of low back pain: a literature review*, Journal of Bodywork & Movement Therapies, 15(4):465-477 (2011).
Gilmore, et al., A Review of Peripheral Nerve Stimulation Techniques Targeting the Medial Branches of the Lumbar Dorsal Rami in the Treatment of Chronic Low Back Pain, Pain Medicine, 21(S1):S41-S46 (2020).
Glaser, et al., Electrical Muscle Stimulation as an Adjunct to Exercise Therapy in the Treatment of Nonacute Low Back Pain: A Randomized Trial, The Journal of Pain, 2(5), pp. 295-300 (2001).
Gondin, et al., "Electromyostimulation Training Effects on Neural Drive and Muscle Architecture." Med. Sci. Sports Exerc., 37(8):1291-1299, (2005).
Gondin, et al., Electromyostimulation Training Effects on Neural Drive and Muscle Architecture, Medicine & Science in Sports & Exercise, 37(8):1291-1299 (Aug. 2005).
Gorman, et al., The Effect of Stimulus Parameters on the Recruitment Characteristics of Direct Nerve Stimulation, IEEE Transactions on Bio-medical Engineering, 30 (7): 407-414 (1983).
Haemmerich, et al., Thermal Tumour Ablation: Devices, Clinical Applications and Future Directions, Int. J. Hyperthermia, 21(8):755-760 (2005) (abstract).
Hagg, et al., The Clinical Importance of Changes in Outcome Scores After Treatment for Chronic Low Back Pain, Eur. Spine. J., 12:12-20 (2003).
Hauggaard et al., "Specific spinal stabilisation exercises in patients with low back pain—a systematic review." Physical Therapy Reviews, 12(3):233-248 (2007).
Hayek et al., "Treatment-Limiting Complications of Percutaneous Spinal Cord Stimulator Implants: A Review of Eight Years of Experience from an Academic Center Database." Neuromodulation, 18:603-609 (2015).
Hebert et al., *The Relationship of Transversus Abdominis and Lumbar Multifidus Activation and Prognostic Factors for Clinical Success With a Stabilization Exercise Program: A Cross-Sectional Study*, Arch. Phys. Med. Rehabil., 91:78-85 (2010).
Herbert, et al., Scoliosis Treatment in Children Using a Programmable, Totally Implantable Muscle Stimulator (ESI), IEEE Transactions on Biomedical Engineering, 36(7): 801-802(Jul. 1989).
Hides et al., *Long-Term Effects of Specific Stabilizing Exercises for First-Episode Low Back Pain*, Spine, 26(11):E243-248 (2001).
Hodges, et al., Intervertebral Stiffness of the Spine is Increased by Evoked Contraction of Transversus Abdominis and the Diaphragm: in Vivo Porcine Studies, Spine 28(23):2594-2601 (Dec. 1, 2003) (abstract).
Hodges, et al., Response of the Deep Paraspinal Muscles to Cortical but not Transmastoid Stimulation is Increased at a Single Lumbar Level Following Interverebral Disc Lesion, Progress in Motor Control Vi--Brazil., 36:2-3 (2007).

(56) References Cited

OTHER PUBLICATIONS

Hodges., Is there a Role for Transversus Abdominis in Lumbo-Pelvis Stability?, Manual Therapy, 4(2):74-86, (1999).
Holm, et al, Sensorimotor Control of the Spine, J. Electromyogr. Kinesiol., 12(3):219-234 (2002), (Abstract).
Hortobagyi, et al., Neural adaptations to Electrical Stimulation Strength Training, European Journal of Applied Physiology, 2011 (pp. 2439-2449) available at: http://www.ncbi.nlm.nih.gov/pubmed/21643920 (Accessed Jul. 19, 2011).
Informal Response to Written Opinion dated Jan. 17, 2012 in Int'l PCT Patent Appl. Serial No. PCT/US2011/027834 (0410).
International Search Report & Written Opinion dated Apr. 5, 2013 in Int'l PCT Patent Application Serial No. PCT/US2012/070259 (0610).
International Search Report & Written Opinion dated Jan. 19, 2016 in Int'l PCT Patent Appl. Serial No. PCT/IB2015/055926 (0910).
International Search Report & Written Opinion dated Jun. 25, 2008 in Int'l PCT Patent Appl. No. PCT/US08/03126 (0210).
International Search Report & Written Opinion dated Oct. 20, 2017 in Int'l PCT Patent Appl. Serial No. PCT/IB2017/053946 (1310).
International Search Report & Written Opinion dated Sep. 28, 2017 in Int'l PCT Patent Appl. Serial No. PCT/IB2017/053945 (1210).
International Search Report & Written Opinion dated Mar. 19, 2015 in Int'l PCT Patent Appl. Serial No. PCT/IB2014/002920 (0810).
International Search Report & Written Opinion dated Sep. 3, 2013 in Int'l PCT Application No. PCT/US2013/045223 (0710).
International Search Report & Written Opinion dated Oct. 17, 2012 in Int'l PCT Patent Appl. No. PCT/US12/49148 (0510).
International Search Report & Written Opinion dated Oct. 19, 2011 in Int'l PCT Patent Appl. No. PCT/US11/27834, 12 pages (0410).
International Search Report and Written Opinion dated Jan. 26, 2016 in Int'l PCT Patent Appl. Serial No. PCT/IB2015/057838 (1010).
International Search Report and Written Opinion dated Oct. 16, 2015 in Int'l PCT Patent Appl. Serial No. PCT/US2015/032732 (1110).
Jinkins, Randy, The Anatomic and Physiologic Basis of Local, Referred and Radiating Lumbosacral Pain Syndromes Related to Disease of the Spine, J. Neuroradiol., 31:163-80 (2004).
Keller, et al., Muscular Contributions to Dynamic Dorsoventral Lumber Spine Stiffness, Eur. Spine J. 16(2): 245-254 (Apr. 29, 2006).
Kiesel, et al., Measurement of Lumbar Multifidus Muscle Contraction with Rehabilitative Ultrasound Imaging, Manual Therapy, 12(2):161-166 (2007) available at: http://www.ncbi.nlm.nih.gov/pubmed/16973400.
Lauridsen, et al., Responsiveness and Minimal Clinically Important Difference for Pain and Disability Instruments in Low Back Pain Patients, BMC Musculoskeletal Disorders, 7(82):16 pages (2006).
Lieber, Richard., Comparison between Animal and Human Studies of Skeletal Muscle Adaptation to Chronic Stimulation, Clinical Orthopaedics and Related Research, 233:19-24 (1988).
Lieber, Richard L., Skeletal Muscle Adaptability. II: Muscle Properties Following Spinal-Cord Injury, Developmental Medicine and Child Neurology, 28(4):533-542 (Aug. 1986).
Lieber, Richard L., Skeletal Muscle Adaptability. III: Muscle Properties Following Chronic Electrical Stimulation, Developmental medicine and child neurology, 28(5):662-670 (Oct. 1986).
McIntosh, et al., Low back pain (chronic), Clin. Evid., 10:1-28(2008).
Medtronic Extension Passer 3555 Accessory Kit—Technical Instructions, 2 pages (2001).
Medtronic Interstim Therapy 3093 & 3889—Implant Manual, 38 pages (2010).
Medtronic, Kinetra, Soletra, and Itrel II, 8870, Neurostimulators for Deep Brain Stimulation (DBS), Software Application Card, Programming Guide for Software A, Dec. 1, 2003, Published 2005, Retrieved from the Internet: URL: http://www.boala-parkinson.ro/Carti%20tehnice/dbs-prog8870-gd.pdf [retrieved Aug. 23, 2018].

Medtronic Model 3464 Receiver/Extension Internalization Manual, SE-4 for Spinal Cord Stimulation (SCS), 7 pages (1986).
Medtronic Tunneling Rod Accessory Kit 8590-41—Technical Manual, 9 pages (No date available).
MicroProbes for Life Science, Nerve Cuff electrodes,2018, available at https://microprobes.com/products/peripheral-electrodes/nerve-cuff, accessed Mar. 5, 2018.
Miyatani, et al., Validity of Estimating Limb Muscle Volume by Bioelectrical Impedance, J. Appl. Physiol., 91:386-394, (2001).
Mortimer, et al., Intramuscular electrical stimulation: tissue damage, Annals of Biomedical Engineering, 8(3):235-244 (1980).
Mortimer, et al., Peripheral Nerve and Muscle Stimulation. In: Horch KW, Dhillon G, eds, Neuroprosthetics: Theory and Practice (Series on Bioengineering & Biomedical Engineering—vol. (2), 2005, World Scientific Publishing Company, (pp. 1-48).
Nachemson, et al., Effectiveness of Treatment with a Brace in Girls Who Have Adolescent Idiopathic Scoliosis, The Journal of Bone and Joint Surgery, 77-A(6):815-822 (Jun. 1995).
OAAO Bock, ActiGait Implantable Drop Foot Stimulator, Surgeon Manual, 2006 (28 pages).
O'Donnell, et al., Electrical Stimulation in the Treatment of Idiopathic Scoliosis, Clinical Orthopaedics and Related Research, No. 229:107-112 (Apr. 1988).
Ostelo et al., Interpreting Change Scores for Pain and Functional Status in Low Back Pain: Towards International Consensus Regarding Minimal Important Change, Spine, 33(1):90-94 (2008).
Paicius, et al., Peripheral Nerve Field Stimulation for the Treatment of Chronic Low Back Pain: Preliminary Results of Long-Term Follow-up: A Case Series, Neuromodulation, 10(3):279-290 (2007) available at: http://www.blackwell-synergy.com/doi/abs/10.1111/j.1525-1403.2007.00116.x-.
Panjabi, Manohar., A hypothesis of Chronic Back Pain: Ligament Sub-Failure Injuries Lead to Muscle Control Dysfunction, European spine journal: official publication of the European Spine Society, the European Spinal Deformity Society, and the European Section of the Cervical Spine Research Society 15(5): 668-676, (May 2006), http://www.ncbi.nlm.nih.gov/pubmed/16047209.
Panjabi, Manohar., The Stabilizing System of the Spine, Part 1, Function, Dysfunction, Adaptation, and Enhancement, Journal of Spinal Disorders, 5(4)383-389 (Dec. 1992), Discussion 397., http://www.ncbi.nlm.nih.gov/pubmed/1490034.
Panjabi, Manohar., The stabilizing system of the spine, Part II, Neutral zone and instability hypothesis, Journal of Spinal Disorders, 5(4):390-396 (Dec. 1992), Discussion 397. http://www.ncbi.nlm.nih.gov/pubmed/1490035.
Partial International Search Report dated Aug. 4, 2015 in Int'l PCT Patent Application Serial No. PCT/US2015/032732 (1110).
PCT Written Opinion dated Aug. 23, 2013 in Int'l PCT Patent Appl. Serial No. PCT/US2010/049148 (0510).
Peckham, et al., Functional Electrical Stimulation for Neuromuscular Applications, Annual review of Biomedical Engineering, 7:327-360 (2005) available at: http://www.ncbi.nlm.nih.gov/pubmed/16004574.
Peterson, et al., Long-term Intramuscular Electrical Activation of the Phrenic Nerve: Safety and Reliability, IEEE Transactions on Bio-medical Engineering, 41(12):1115-1126 (1994).
Poitras, et al., Evidence-informed Management of Chronic Low Back Pain with Transcutaneous Electrical Nerve Stimulation, Interferential Current, Electrical Muscle Stimulation, Ultrasound, And Thermotherapy, The Spine Journal, 8:226-233 (2008).
Reed B., The Physiology of Neuromuscular Electrical Stimulation, Pediatric Physical Therapy, 9(3):96-102 (1997) available at: http://journals.lww.com/pedpt/pages/articleviewer.aspx?year=1997&issue=00-930&article=00002&type=abstract.
Rosatelli, et al., Three-Dimensional Study of the Musculotendinous Architecture Of Lumber Multifidus and its Functional Implications, Clinical Anatomy, 21(6):539-544 (Sep. 2008).
RS Medical, RS-4M Muscle Stimulator, available at http://www.rsmedical.com/documents/fact_sheet_RS4m.pdf (last visited Jul. 19, 2012).
Russo, et al., Muscle Control and Non-specific Chronic Low Back Pain, Neuromodulation: Technology at the Neural Interface, 21:1-9 (2017).

(56) References Cited

OTHER PUBLICATIONS

Rutkove., Electrical Impedance Myography: Background, Current State, and Future Directions, Muscle Nerve, 40(6):936-946 (2009).
Schwartz, et al., Therapeutic Electrical Stimulation of the Hypoglossal Nerve in Obstructive Sleep Apnea, Arch Otolaryngal Head Neck Surg., 127:1216-1223 (2001).
Senn et al., "Measurement in clinical trials: A neglected issue for statisticians?" Statist. Med., 28:3189-3209 (2009).
Sheffler et al., Neuromuscular Electrical Stimulation in Neurorehabilitation, Muscle Nerve, 35:562-590 (2007).
Sippl, Charles J., Computer Dictionary: Third Edition, pp. 2257 and 2340 (1984).
Sluijter, Radiofrequency Ablation in the Management of Spinal Pain, C212, IV(1):10-15, (2006).
Soer et al., *Clinimetric properties of the EuroQol-50 in patients with chronic low backpain,* The Spine Journal, 12:1035-1039 (2012).
Solomonow, et al., The Ligamento-Muscular Stabilizing System of the Spine, Spine, 23(23):2552-2562, (1998).
Spinal Fusion Guidelines, MD Guidelines, 2009. www.mdguidelines.com/spinal-fusion.
Stokes, et al., Surface EMG Electrodes Do Not Accurately Record from Lumbar Multifidus Muscles, Clin. Biomech, 18(1):9-13, (2003), (Abstract Only).
Unit III—The Spine, "Motions of the Spine," available at https://courses.vcu.edu/DANC291-003/unit_3.htm, accessed Mar. 5, 2018.
Van Buyten et al., *Neuromuscular Reactivation—A New Therapy for Patients with Chronic Low Back Pain (CLBP): Results of a European Multicenter Feasibility Study,* Neuromodulation, 16:e176 (2013).
van DIEEN, et al., Trunk Muscle Recruitment Patterns in Patients with Low Back Pain Enhance the Stability of the Lumbar Spine, Spine, (2003), 28(8):834-841 (Abstract Only).
Van, et al., The Use of Real-Time Ultrasound Imaging for Biofeedback of Lumbar Multifidus Muscle Contraction in Healthy Subjects, The Journal of Orthopaedic and Sports Physical Therapy, 36(12):920-925 (2006) available at: http://www.ncbi.nlm.nih.gov/pubmed/17193869.
Verrills, et al., Peripheral Nerve Stimulation: A Treatment for Chronic Low Back Pain and Failed Back Surgery Syndrome?, Neuromodulation: Technology at the Neural Interface, 12(1):68-75, (2009).
Vrbova et al., Application of Muscle/Nerve Stimulation in Health and Disease, Springer Verlag (2008) available at: http://books.google.com/books?hl=en&lr=&id=jb8fDGxkbqEC&oi=fn-d&pg=PA1&dq=Application+of+Muscle/Nerve+Stimulation+in+Health+and+-Disease&ots=CMV5rXiDQD&sig=Wg8ulYOC4PgvVDzcjdwBub5U2To (Accessed Jun. 2, 2011).
Wallwork, et al., The Effect of Chronic Low Back Pain on Size and Contraction of the Lumbar Multifidus Muscle, Manual Therapy, 14(5):496-500 (2009) available at: http://www.ncbi.nlm.nih.gov/pubmed/19027343.
Ward, et al., Architectural Analysis and Intraoperative Measurements Demonstrate the Unique Design of the Multifidus for Lumbar Spine Stability, J. Bone Joint Surg. [Am.] 91:176-185, PMC2663324 (2009).
Wikipedia., Anterior superior iliac spine, Updated Feb. 12, 2018, available at https://en.wikipedia.org/wiki/Anterior_superior_iliac_spine.
Wikipedia., Blunt Dissection, Updated Feb. 14, 2018, available at https://en.wikipedia.org/wiki/Blunt_dissection.
Wikipedia, Cavernous Nerves, Updated Feb. 26, 2018, available at https://en.wikipedia.org/wiki/Cavernous_nerves.
Wikipedia, Dorsal Ramus of Spinal Nerve, Updated Feb. 12, 2018, available at https://en.wikipedia.org/wiki/Dorsal_ramus_of_spinal_nerve.
Wikipedia, "Interference Fit," http://en.wikipedia.org/wiki/Interference.sub.--fit, accessed Dec. 4, 2014.
Wikipedia, Time-division Multiplexing, https://en.wikipedia.org/wiki/Time-division.sub.--multiplexing (accessed Nov. 12, 2015).
Wikipedia, Ventral Ramus of Spinal Nerve, Updated Feb. 12, 2018, available at https://en.wikipedia.org/wiki/Ventral_ramus_of_spinal_nerve.
Wright et al., Morphologic and Histochemical Characteristics of Skeletal Muscle after Long-Term Intramuscular Electrical Stimulation, Spine, 17(7):767-770 (1992) available at: http://www.ncbi.nlm.nih.gov/pubmed/1502640 (Accessed Aug. 2, 2011).
Written Opinion dated Nov. 16, 2011 in Int'l PCT Patent Appl. No. PCT/US2011/027934, 7 pages (0410).
Written Opinion of the International Preliminary Examining Authority dated Feb. 3, 2014 in Int'l PCT Patent Appl. Serial No. PCT/US2012/070259 (0610).
Zundert, et al., Radiofrequency Treatment for Chronic Pain Syndromes, CPD Anaesthesia, 6(1):13-17 (2004).
"Ineffective treatments for low back pain might actually make the pain (and treatment worse," The Mighty, Military News, https://www.wearethemight.com/sponsored-content/ineffective-treatments-for-low-back-pain-might-actually-make-the-pain-and-treatment-worse/, accessed Oct. 10, 2023.
Jensen, et al., Mechanisms of spinal cord stimulation for the treatment of pain: Still in the dark after 50 years, Eur. J. Pain, 23:652-659 (2019).

* cited by examiner

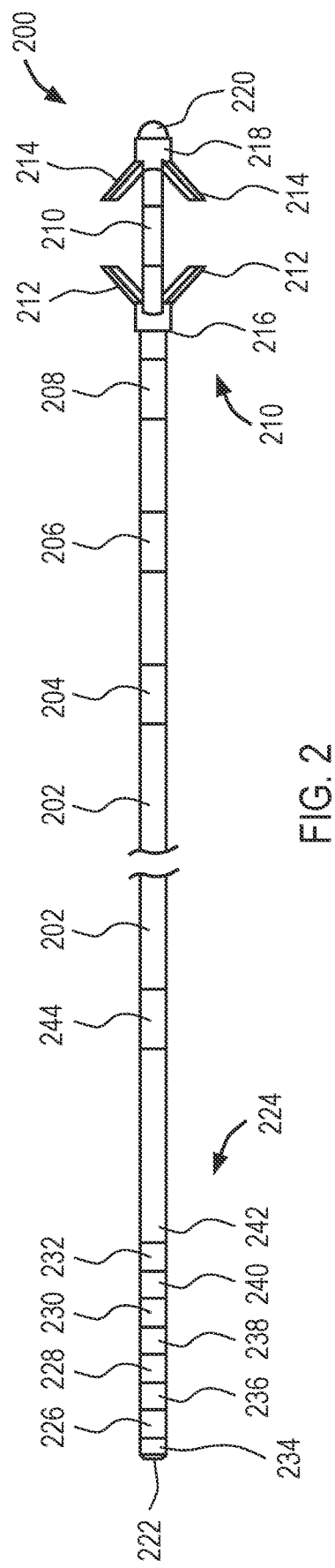
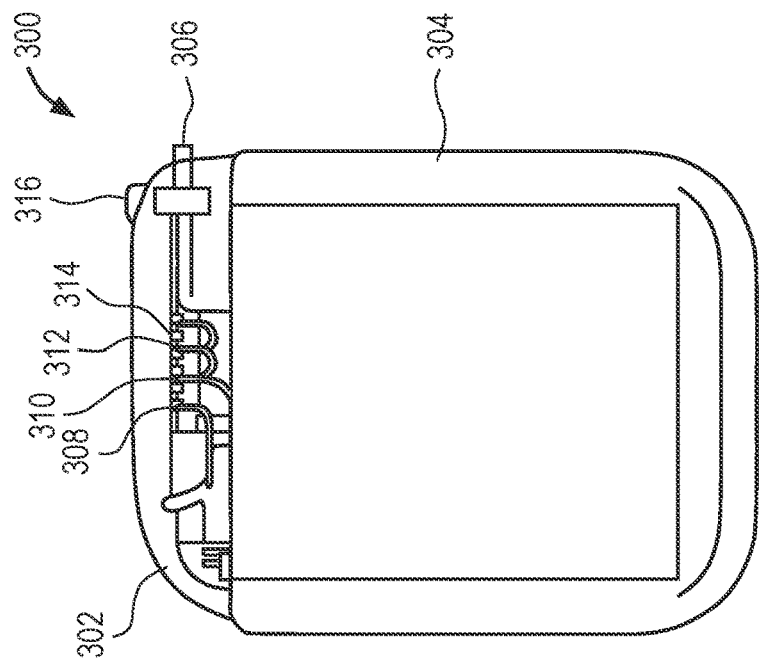
FIG. 2
FIG. 3A

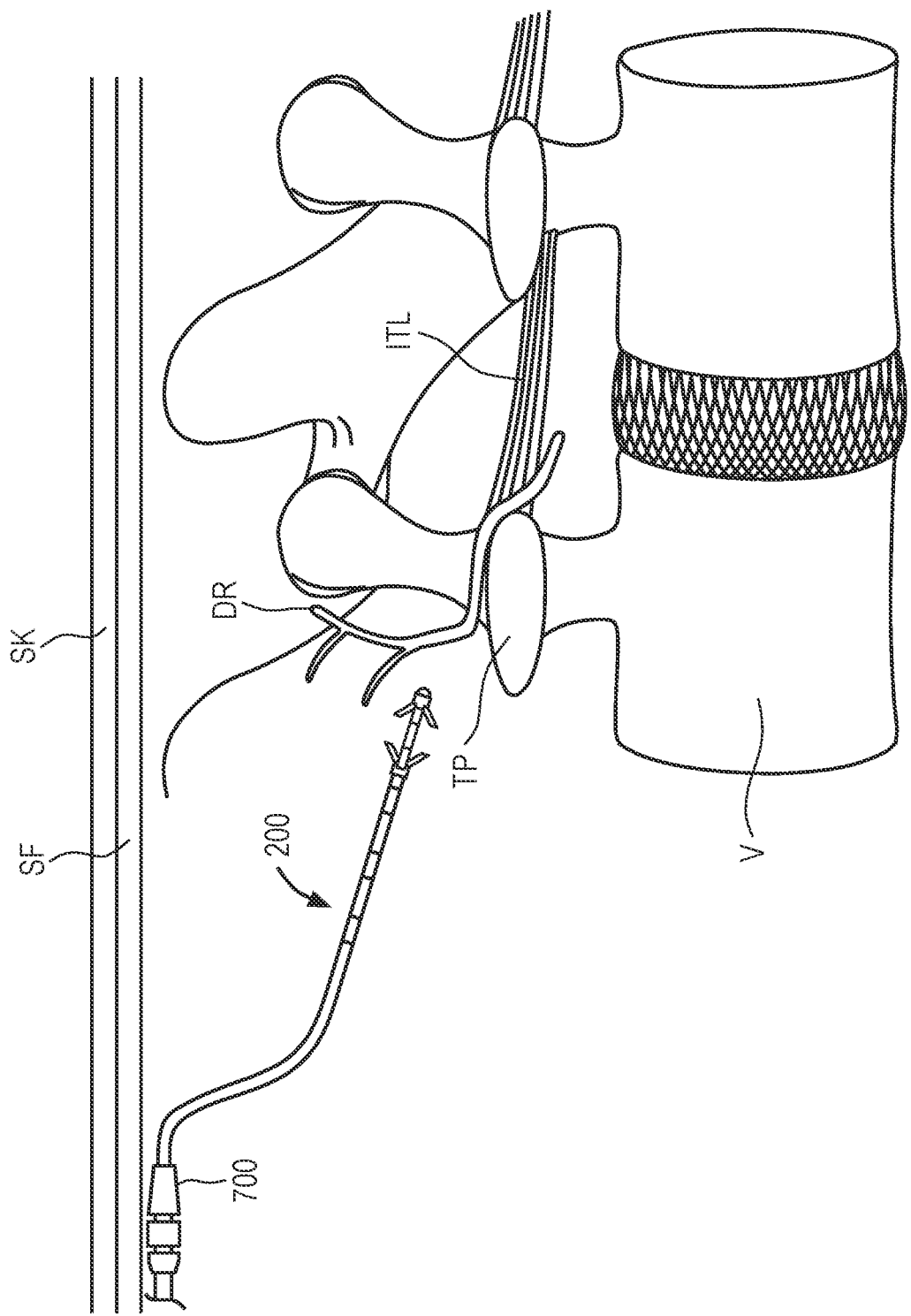

SYSTEMS AND METHODS FOR RESTORING MUSCLE FUNCTION TO THE LUMBAR SPINE

I. CROSS-REFERENCE TO RELATED APPLICATIONS

This application is a continuation of U.S. patent application Ser. No. 17/812,989, filed Jul. 15, 2022, now U.S. Pat. No. 11,679,262, which is a continuation of U.S. patent application Ser. No. 17/092,073, filed Nov. 6, 2020, which is a continuation of U.S. patent application Ser. No. 15/944,730, filed Apr. 3, 2018, now U.S. Pat. No. 10,828,490, which is a continuation of U.S. patent application Ser. No. 15/299,399, filed Oct. 20, 2016, now U.S. Pat. No. 10,016,603, which is a continuation of U.S. patent application Ser. No. 14/792,430, filed Jul. 6, 2015, now U.S. Pat. No. 9,474,906, which is a continuation of U.S. patent application Ser. No. 14/061,614, filed Oct. 23, 2013, now U.S. Pat. No. 9,072,897, which is a continuation-in-part application of U.S. patent application Ser. No. 13/858,809, filed Apr. 8, 2013, now U.S. Pat. No. 8,606,358, which is a continuation of U.S. patent application Ser. No. 12/075,174, filed Mar. 10, 2008, now U.S. Pat. No. 8,428,728, which claims the benefit of priority of U.S. Provisional Application Ser. No. 60/905,979, filed Mar. 9, 2007, the entire contents of each of which are incorporated herein by reference.

U.S. patent application Ser. No. 17/092,073, filed Nov. 6, 2020, is also a continuation-in-part of U.S. patent application Ser. No. 16/817,574, filed Mar. 12, 2020, now U.S. Pat. No. 10,926,083, which is a continuation application of U.S. patent application Ser. No. 15/853,543, filed Dec. 22, 2017, now U.S. Pat. No. 10,661,078, which is a continuation application of U.S. patent application Ser. No. 14/849,478, filed Sep. 9, 2015, now U.S. Pat. No. 9,861,811, which is a continuation application of U.S. patent application Ser. No. 13/045,421, filed Mar. 10, 2011, now U.S. Pat. No. 9,248,278, which claims the benefit of priority of U.S. Provisional Application Ser. No. 61/339,957, filed Mar. 11, 2010, the entire contents of each of which are incorporated herein by reference.

II. FIELD OF THE INVENTION

This application generally relates to systems and methods for neuromuscular electrical stimulation, including stimulation of tissue associated with control of the lumbar spine for treatment of back pain.

III. BACKGROUND OF THE INVENTION

The human back is a complicated structure including bones, muscles, ligaments, tendons, nerves and other structures. The spinal column has interleaved vertebral bodies and intervertebral discs, and permits motion in several planes including flexion-extension, lateral bending, axial rotation, longitudinal axial distraction-compression, anterior-posterior sagittal translation, and left-right horizontal translation. The spine provides connection points for a complex collection of muscles that are subject to both voluntary and involuntary control.

Back pain in the lower or lumbar region of the back is common. In many cases, the cause of back pain is unknown. It is believed that some cases of back pain are caused by abnormal mechanics of the spinal column. Degenerative changes, injury of the ligaments, acute trauma, or repetitive microtrauma may lead to back pain via inflammation, biochemical and nutritional changes, immunological factors, changes in the structure or material of the endplates or discs, and pathology of neural structures.

The spinal stabilization system may be conceptualized to include three subsystems: 1) the spinal column, which provides intrinsic mechanical stability; 2) the spinal muscles, which surround the spinal column and provide dynamic stability; and 3) the neuromotor control unit, which evaluates and determines requirements for stability via a coordinated muscle response. In patients with a functional stabilization system, these three subsystems work together to provide mechanical stability. It is applicant's realization that low back pain results from dysfunction of these subsystems.

The spinal column consists of vertebrae and ligaments, e.g. spinal ligaments, disc annulus, and facet capsules. There has been an abundance of in-vitro work in explanted cadaver spines and models evaluating the relative contribution of various spinal column structures to stability, and how compromise of a specific column structure will lead to changes in the range of motion of spinal motion segments.

The spinal column also has a transducer function, to generate signals describing spinal posture, motions, and loads via mechanoreceptors present in the ligaments, facet capsules, disc annulus, and other connective tissues. These mechanoreceptors provide information to the neuromuscular control unit, which generates muscle response patterns to activate and coordinate the spinal muscles to provide muscle mechanical stability. Ligament injury, fatigue, and viscoelastic creep may corrupt signal transduction. If spinal column structure is compromised, due to injury, degeneration, or viscoelastic creep, then muscular stability must be increased to compensate and maintain stability.

Muscles provide mechanical stability to the spinal column. This is apparent by viewing cross section images of the spine, as the total area of the cross sections of the muscles surrounding the spinal column is larger than the spinal column itself. Additionally, the muscles have much larger lever arms than those of the intervertebral disc and ligaments.

Under normal circumstances, the mechanoreceptors exchange signals with the neuromuscular control unit for interpretation and action. The neuromuscular control unit produces a muscle response pattern based upon several factors, including the need for spinal stability, postural control, balance, and stress reduction on various spinal components.

It is believed that in some patients with back pain, the spinal stabilization system is dysfunctional. With soft tissue injury, mechanoreceptors may produce corrupted signals about vertebral position, motion, or loads, leading to an inappropriate muscle response. In addition, muscles themselves may be injured, fatigued, atrophied, or lose their strength, thus aggravating dysfunction of the spinal stabilization system. Conversely, muscles can disrupt the spinal stabilization system by going into spasm, contracting when they should remain inactive, or contracting out of sequence with other muscles. As muscles participate in the feedback loop via mechanoreceptors in the form of muscle spindles and golgi tendon organs, muscle dysfunction may further compromise normal muscle activation patterns via the feedback loops.

Trunk muscles may be categorized into local and global muscles. The local muscle system includes deep muscles, and portions of some muscles that have their origin or insertion on the vertebrae. These local muscles control the stiffness and intervertebral relationship of the spinal segments. They provide an efficient mechanism to fine-tune the control of intervertebral motion. The lumbar multifidus, with its vertebra-to-vertebra attachments is an example of a muscle of the local system. Another example is the transverse abdominus, with its direct attachments to the lumbar vertebrae through the thoracolumbar fascia.

The multifidus is the largest and most medial of the lumbar back muscles. It has a repeating series of fascicles which stem from the laminae and spinous processes of the vertebrae, and exhibit a constant pattern of attachments caudally. These fascicles are arranged in five overlapping groups such that each of the five lumbar vertebrae gives rise to one of these groups. At each segmental level, a fascicle arises from the base and caudolateral edge of the spinous process, and several fascicles arise, by way of a common tendon, from the caudal tip of the spinous process. Although confluent with one another at their origin, the fascicles in each group diverge caudally to assume separate attachments to the mamillary processes, the iliac crest, and the sacrum. Some of the deep fibers of the fascicles that attach to the mamillary processes attach to the capsules of the facet joints next to the mamillary processes. The fasicles arriving from the spinous process of a given vertebra are innervated by the medial branch of the dorsal ramus that issues from below that vertebra.

The global muscle system encompasses the large, superficial muscles of the trunk that cross multiple motion segments, and do not have direct attachment to the vertebrae. These muscles are the torque generators for spinal motion, and control spinal orientation, balance the external loads applied to the trunk, and transfer load from the thorax to the pelvis. Global muscles include the oblique internus abdominus, the obliquus externus abdmonimus, the rectus abdominus, the lateral fibers of the quadratus lumborum, and portions of the erector spinae.

Normally, load transmission is painless. Over time, dysfunction of the spinal stabilization system is believed to lead to instability, resulting in overloading of structures when the spine moves beyond its neutral zone. The neutral zone is a range of intervertebral motion, measured from a neutral position, within which the spinal motion is produced with a minimal internal resistance. High loads can lead to inflammation, disc degeneration, facet joint degeneration, and muscle fatigue. Since the endplates and annulus have a rich nerve supply, it is believed that abnormally high loads may be a cause of pain. Load transmission to the facets also may change with degenerative disc disease, leading to facet arthritis and facet pain.

For patients believed to have back pain due to instability, clinicians offer treatments intended to reduce intervertebral motion. Common methods of attempting to improve muscle strength and control include core abdominal exercises, use of a stability ball, and Pilates. Spinal fusion is the standard surgical treatment for chronic back pain. Following fusion, motion is reduced across the vertebral motion segment. Dynamic stabilization implants are intended to reduce abnormal motion and load transmission of a spinal motion segment, without fusion. Categories of dynamic stabilizers include interspinous process devices, interspinous ligament devices, and pedicle screw-based structures. Total disc replacement and artificial nucleus prostheses also aim to improve spine stability and load transmission while preserving motion.

There are a number of problems associated with current implants that aim to restore spine stabilization. First, it is difficult to achieve uniform load sharing during the entire range of motion if the location of the optimum instant axis of rotation is not close to that of the motion segment during the entire range of motion. Second, cyclic loading of dynamic stabilization implants may cause fatigue failure of the implant, or the implant-bone junction, e.g. screw loosening. Third, implantation of these systems requires surgery, which may cause new pain from adhesions, or neuroma formation. Moreover, surgery typically involves cutting or stripping ligaments, capsules, muscles, and nerve loops, which may interfere with the spinal stabilization system.

Functional electrical stimulation (FES) is the application of electrical stimulation to cause muscle contraction to re-animate limbs following damage to the nervous system such as with stroke or spine injury. FES has been the subject of much prior art and scientific publications. In FES, the goal generally is to bypass the damaged nervous system and provide electrical stimulation to nerves or muscles directly which simulates the action of the nervous system. One lofty goal of FES is to enable paralyzed people to walk again, and that requires the coordinated action of several muscles activating several joints. The challenges of FES relate to graduation of force generated by the stimulated muscles, and the control system for each muscle as well as the system as a whole to produce the desired action such as standing and walking.

With normal physiology, sensors in the muscle, ligaments, tendons and other anatomical structures provide information such as the force a muscle is exerting or the position of a joint, and that information may be used in the normal physiological control system for limb position and muscle force. This sense is referred to as proprioception. In patients with spinal cord injury, the sensory nervous system is usually damaged as well as the motor system, and thus the afflicted person loses proprioception of what the muscle and limbs are doing. FES systems often seek to reproduce or simulate the damaged proprioceptive system with other sensors attached to a joint or muscle.

For example, in U.S. Pat. No. 6,839,594 to Cohen, a plurality of electrodes are used to activate selected groups of axons in a motor nerve supplying a skeletal muscle in a spinal cord patient (thereby achieving graduated control of muscle force) and one or more sensors such as an accelerometer are used to sense the position of limbs along with electrodes attached to muscles to generate an electromyogram (EMG) signal indicative of muscle activity. In another example, U.S. Pat. No. 6,119,516 to Hock, describes a biofeedback system, optionally including a piezoelectric element, which measures the motions of joints in the body. Similarly a piezoelectric crystal may be used as a muscle activity sensor as described by U.S. Pat. No. 5,069,680 to Grandjean.

FES has also been used to treat spasticity, characterized by continuous increased muscle tone, involuntary muscle contractions, and altered spinal reflexes which leads to muscle tightness, awkward movements, and is often accompanied by muscle weakness. Spasticity results from many causes including cerebral palsy, spinal cord injury, trauma, and neurodegenerative diseases. U.S. Pat. No. 7,324,853 to Ayal describes apparatus and method for electrically stimulating nerves that supply muscles to modify the muscle contractions that lead to spasticity. The apparatus includes a control system configured to analyze electrical activity of one or more muscles, limb motion and position, and mechanical strain in an anatomical structure.

Neuromuscular Electrical Stimulation (NMES) is a subset of the general field of electrical stimulation for muscle contraction, as it is generally applied to nerves and muscles which are anatomically intact, but malfunctioning is a different way. NMES may be delivered via an external system or, in some applications, via an implanted system.

NMES via externally applied skin electrodes has been used to rehabilitate skeletal muscles after injury or surgery in the associated joint. This approach is commonly used to aid in the rehabilitation of the quadriceps muscle of the leg after knee surgery. Electrical stimulation is known to not only improve the strength and endurance of the muscle, but also to restore malfunctioning motor control to a muscle. See, e.g., Gondin et al., "Electromyostimulation Training Effects on Neural Drive and Muscle Architecture", Medicine & Science in Sports & Exercise 37, No. 8, pp. 1291-99 (August 2005).

An implanted NMES system has been used to treat incontinence by stimulating nerves that supply the urinary or anal sphincter muscles. For example, U.S. Pat. No. 5,199,430 to Fang describes implantable electronic apparatus for assisting the urinary sphincter to relax.

The goals and challenges of rehabilitation of anatomically intact (i.e., non-pathological) neuromuscular systems are fundamentally different from the goals and challenges of FES for treating spinal injury patients or people suffering from spasticity. In muscle rehabilitation, the primary goal is to restore normal functioning of the anatomically intact neuromuscular system, whereas in spinal injury and spasticity, the primary goal is to simulate normal activity of a pathologically damaged neuromuscular system.

It would therefore be desirable to provide an apparatus and method to rehabilitate muscle associated with control of the lumbar spine to treat back pain.

It further would be desirable to provide an apparatus and method to restore muscle function of local segmental muscles associated with the lumbar spine stabilization system.

IV. SUMMARY OF THE INVENTION

The present invention overcomes the drawbacks of previously-known systems by providing systems and methods for restoring muscle function to the lumbar spine to treat, for example, low back pain. The system may include one or more electrodes coupled to an implantable pulse generator (IPG), a handheld activator configured to be wirelessly coupled to the IPG, and an external programmer configured to be wirelessly coupled to the IPG. The one or more electrodes are configured to be implanted in or adjacent to tissue associated with control of the lumbar spine. The IPG is coupled to the one or more electrodes, and preferably includes a programmable controller and a first communications circuit. The handheld activator includes a second communications circuit and is configured to transfer a stimulation command to the IPG via the first and second communications circuits. The external programmer has a third communications circuit and is configured to transfer programming data to the IPG via the first and third communications circuits. The stimulation command may direct the programmable controller to stimulate the tissue in accordance with the programming data.

The external programmer may be coupled to a computer, e.g., a physician's computer, configured to run software. The software preferably causes the programming data to be displayed, e.g., on the computer's display, and permits selection and adjustment of such programming data based on user input.

The programming data transferred between the external programmer and the IPG preferably includes at least one of: pulse amplitude, pulse width, stimulation rate, stimulation frequency, ramp timing, cycle timing, session timing, or electrode configuration. For example, a physician may adjust a stimulation rate or cause a treatment session to be started on the external programmer or on the programming system software via the computer and programming data will be sent to the IPG to execute such commands.

The stimulation commands transferred between the activator and the IPG preferably include at least one of: a command to start a treatment session or stop the treatment session; a command to provide a status of the implantable pulse generator; or a request to conduct an impedance assessment. For example, a user, e.g., physician, patient, caretaker, may cause a treatment session to be started on the activator and a command will be sent to the IPG to execute such command. The activator may have a user interface configured to receive user input to cause a stimulation command to be generated.

The one or more electrodes are configured to be implanted in or adjacent to at least one of nervous tissue, a muscle, a ligament, or a joint capsule. The system may include a lead coupled to the IPG and having the electrode(s) disposed thereon. The lead may be coupled to a first fixation element configured to anchor the lead to an anchor site, e.g., muscle, bone, nervous tissue, a ligament, and/or a joint capsule. The lead may be further coupled to a second fixation element, distal to the first fixation element. In one embodiment, the first fixation element is angled distally relative to the lead and the second fixation element is angled proximally relative to the lead such that the first and second fixation elements are configured to sandwich the anchor site therebetween.

The programmable controller of the IPG may be programmed with, for example, stimulation parameters and configured to adjust stimulation parameters based on receipt of programming data from the external programmer. In one embodiment, the programmable controller is programmed to direct the one or more electrodes to stimulate the tissue at a pulse amplitude between about 0.1-7 mA or about 2-5 mA, a pulse width between about 20-500 µs or about 100-400 µs, and a stimulation rate between about 1-20 Hz or about 15-20 Hz. In addition, the programmable controller may be programmed to direct the one or more electrodes to stimulate the tissue in a charge-balanced manner. Further, the programmable controller may be programmed to direct the one or more electrodes to stimulate the tissue with increasing pulse amplitudes to a peak pulse amplitude and then stimulate with decreasing pulse amplitudes. In one embodiment, the programmable controller is programmed to direct the one or more electrodes to stimulate the dorsal ramus nerve that innervates the multifidus muscle. The programmable controller also may be programmed to direct the one or more electrodes to stimulate the fascicles of the dorsal ramus nerve that innervates the multifidus muscle.

The first, second, and/or third communication circuits may be inductive and/or employ RF transceivers.

In one embodiment, the handheld activator includes a pad coupled to a handheld housing by a cable. Preferably, the cable has a sufficient length to enable a user to place the pad in extracorporeal proximity to the IPG while viewing the handheld housing.

In accordance with another aspect of the present invention, a method for restoring muscle function of the lumbar spine to reduce back pain is provided. The method includes providing one or more electrodes, an implantable pulse generator, an external programmer, and a handheld activator; implanting the one or more electrodes in or adjacent to tissue associated with control of the lumbar spine; implanting the implantable pulse generator in communication with the one or more electrodes; transferring programming data to the implantable pulse generator from the external programmer; and operating the handheld activator to command the implantable pulse generator to stimulate the tissue with the one or more electrodes responsive to the programming data.

V. BRIEF DESCRIPTION OF THE DRAWINGS

FIG. 2 shows an exemplary electrode lead of the stimulator system of FIG. 1A.

FIG. 3A shows an exemplary implantable pulse generator (IPG) of the stimulator system of FIG. 1A.

FIGS. 7A through 7D show an exemplary method for implanting an electrode lead and IPG in accordance with the principles of the present invention.

VI. DETAILED DESCRIPTION OF THE INVENTION

The neuromuscular stimulation system of the present invention comprises implantable devices for facilitating electrical stimulation to tissue within a patient's back and external devices for wirelessly communicating programming data and stimulation commands to the implantable devices. The devices disclosed herein may be utilized to stimulate tissue associated with local segmental control of the lumbar spine in accordance with the programming data to rehabilitate the tissue over time. In accordance with the principles of the present invention, the stimulator system may be optimized for use in treating back pain of the lumbar spine.

Figure 1A:
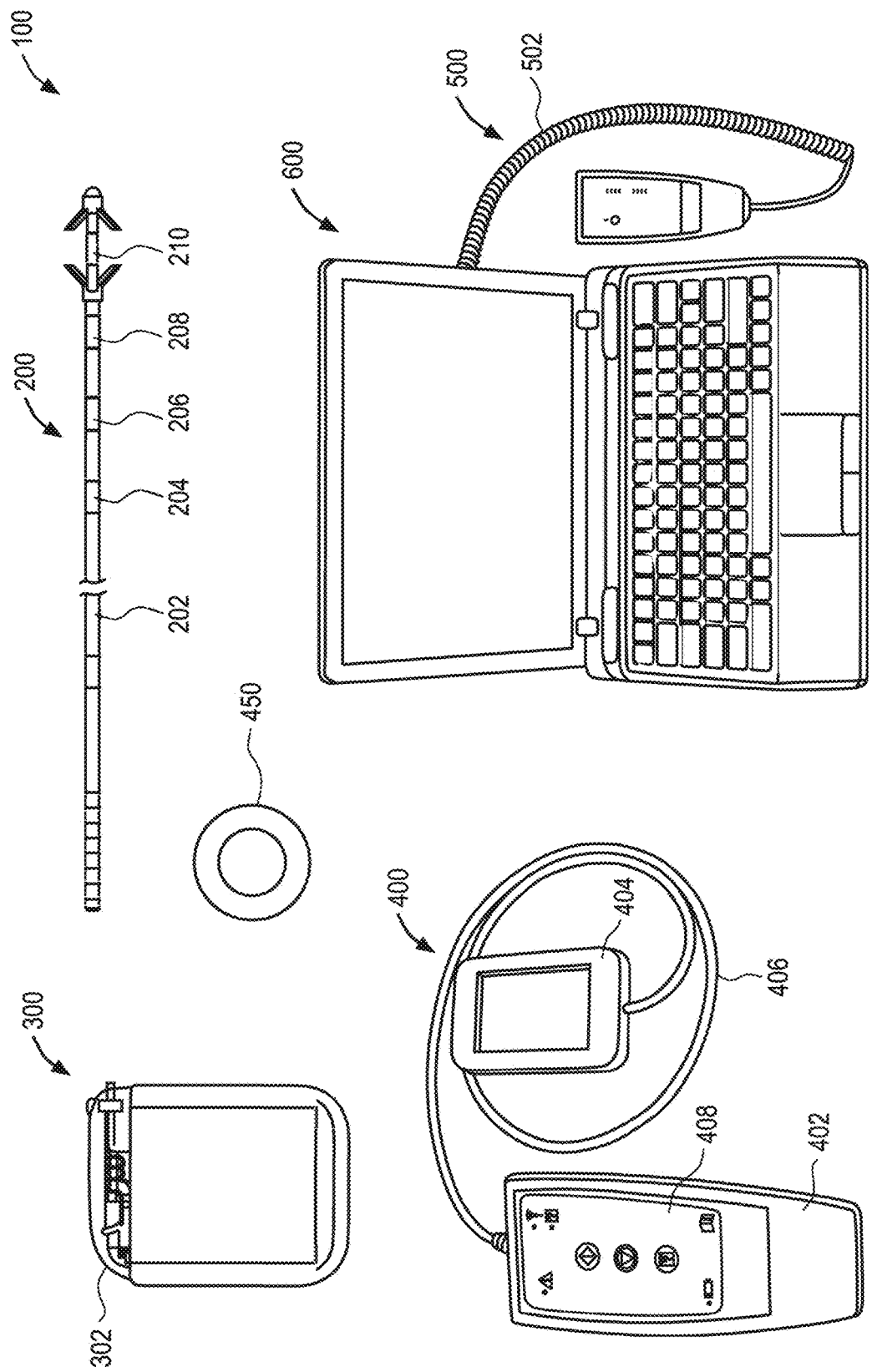
FIG. 1A is a schematic view of an exemplary embodiment of a stimulator system constructed in accordance with the principles of the present invention.

Referring to FIG. 1A, an overview of an exemplary stimulator system constructed in accordance with the principles of the present invention is provided. In FIG. 1A, components of the system are not depicted to scale on either a relative or absolute basis. Stimulator system 100 includes electrode lead 200, implantable pulse generator (IPG) 300, activator 400, optional magnet 450, external programmer 500, and software-based programming system 600.

Electrode lead 200 includes lead body 202 having a plurality of electrodes, illustratively, electrodes 204, 206, 208, and 210. Electrode lead 200 is configured for implantation in or adjacent to tissue, e.g., nervous tissue, muscle, a ligament, and/or a joint capsule including tissue associated with local segmental control of the lumbar spine. Electrode lead 200 is coupled to IPG 300, for example, via connector block 302. IPG 300 is configured to generate pulses such that electrodes 204, 206, 208, and/or 210 deliver neuromuscular electrical stimulation ("NMES") to target tissue. In one embodiment, the electrodes are positioned to stimulate a peripheral nerve where the nerve enters skeletal muscle, which may be one or more of the multifidus, transverse abdominus, quadratus lumborum, psoas major, internus abdominus, obliquus externus abdominus, and erector spinae muscles. Such stimulation may induce contraction of the muscle to restore neural control and rehabilitate the muscle, thereby improving muscle function of local segmental muscles of the lumbar spine, improving lumbar spine stability, and reducing back pain.

IPG 300 is controlled by, and optionally powered by, activator 400, which includes control module 402 coupled to pad 404, e.g., via cable 406. Control module 402 has user interface 408 that permits a user, e.g., patient, physician, caregiver, to adjust a limited number of operational parameters of IPG 300 including starting and stopping a treatment session. Control module 402 communicates with IPG 300 via pad 404, which may comprise an inductive coil or RF transceiver configured to communicate information in a bidirectional manner across a patient's skin to IPG 300 and, optionally, to transmit power to IPG 300.

Stimulator system 100 also may include optional magnet 450 configured to transmit a magnetic field across a patient's skin to IPG 300 such that a magnetic sensor of IPG 300 senses the magnetic field and IPG 300 starts or stops a treatment session responsive to the sensed magnetic field.

In FIG. 1A, software-based programming system 600 is installed and runs on a conventional laptop computer, "smart phone", tablet, or similar device with computing power, and is used by the patient's physician together with external programmer 500 to provide programming to IPG 300. During patient visits, external programmer 500 may be coupled, either wirelessly or using a cable such as cable 502, to the physician's computer such that software-based programming system 600 may download for review data stored on IPG 300 via external programmer 500. Software-based programming system 600 also may transfer programming data to IPG 300 via external programmer 500 to reprogram stimulation parameters programmed into IPG 300. For example, programming system 600 may be used to program and adjust parameters such as pulse amplitude (voltage or current), pulse width, stimulation rate, stimulation frequency, ramp timing, cycle timing, session timing, and electrode configuration. Programming system 600 also may be configured to upload and store data retrieved from IPG 300 to a remote server for later access by the physician.

Figure 1B:
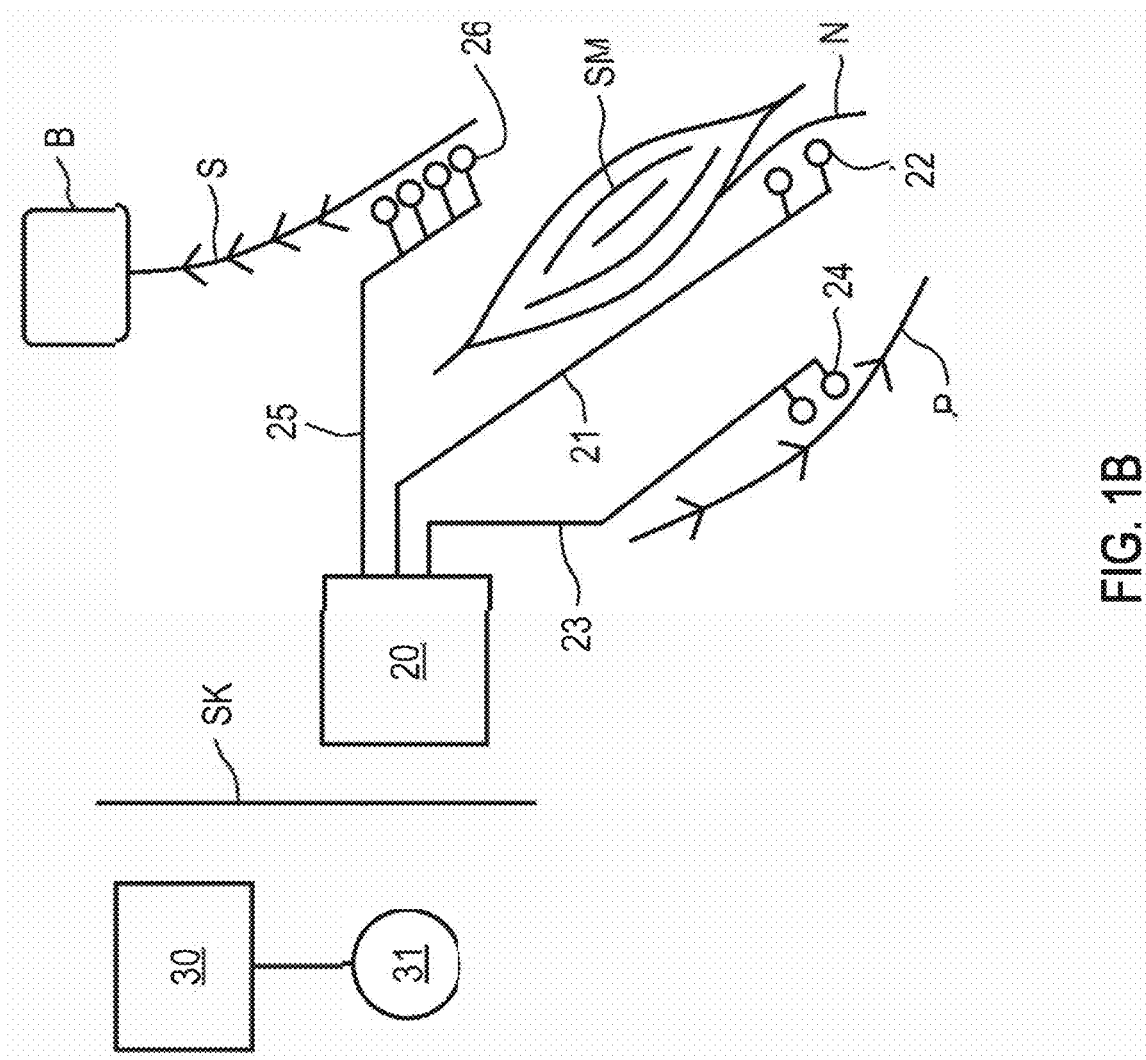
FIG. 1B is a schematic view of an exemplary embodiment of a stimulator system constructed in accordance with the principles of the present invention.

In FIG. 1B implantable stimulator 20 is connected to a plurality of electrode leads. Illustratively, electrode lead 21 is connected to electrode pair 22, which is situated close to or around a peripheral nerve N where the nerve enters skeletal muscle SM, which may be a multifidus muscle. Electrode pair 22 may deliver neuromuscular electrical stimulation ("NMES") pulses to nerve N that induce contraction of muscle SM to effect contraction of the muscle, and restoration of neural control and rehabilitation of the muscle, as described in the aforementioned U.S. Patent Application Publication No. US2008/0228241 to Sachs. Electrode lead 23 is illustratively disposed with electrode pair 24 adjacent or near to peripheral nerve P, such that electrical stimulation may be applied to achieve pain control in the region served by the peripheral nerves. Electrode lead 25 illustratively includes quadripolar electrode array 26, which is placed near spinal cord S in a manner well known to one skilled in the art to deliver Spinal Cord Stimulation therapy that reduces or blocks the transmission of pain signals to the patient's brain B.

Implantable stimulator 20 is controlled by, and optionally powered by, external control system 30, which communicates with stimulator 20 via antenna 31, which may comprise an inductive coil configured to transmit power and communicate information in a bidirectional manner across skin SK. The technology for antenna 31 is well known to one skilled in the art and may include a magnet, a coil of wire, a longer range telemetry system (such as using MICS), or technology similar to a pacemaker programmer. Alternatively, coil 30 may be used to transmit power only, and separate radio frequency transmitters may be provided in external control system 30 and stimulator 20 for establishing directional data communication.

Some patients receiving stimulator 20 may experience back pain due to previous injury and/or loss of muscle tone, while other patients may find the contractions induced by operation of the NMES circuitry to be unpleasant. Accordingly, stimulator 20 further includes an analgesic stimulation circuitry module to block or reduce pain associated with the previous injury or muscle contractions induced by the NMES therapy. As depicted in FIG. 1B, in one preferred application of stimulator 20, electrode pair 22 is situated on the medial branch of the dorsal ramus to deliver NMES pulses that cause muscle contraction to effect restoration of neural drive to and rehabilitation of the multifidus muscle. Analgesic stimulation circuitry module may simultaneously be coupled to electrode pair 24, via electrode lead 23, and quad electrode 26, via electrode lead 25, to block or reduce pain signals generated in spinal cord S or peripheral nerve P. In addition, electrode pair 22 also may be used, e.g., by a controller switching electrode switching array to couple electrode pair 22 to the analgesic stimulation circuitry module, to deliver higher frequency stimulation to block afferent pain signals. In this manner, it is expected that NMES therapy may be provided while reducing patient discomfort and pain associated with any pre-existing injury.

Stimulator 20 and the electrodes also may be configured such that one set of electrodes is used to simulate the tissues on one side of the body, and another set of electrodes is used to simulate tissues on the other side of the body. In this manner, the stimulator and electrode system can be configured to deliver unilateral or bilateral stimulation, or a combination of electrodes stimulating tissues in no particular geometric arrangement.

Referring now to FIG. 2, an exemplary embodiment of electrode lead 200 is described. Electrode lead 200 contains a plurality of electrodes 204, 206, 208, and 210, disposed at distal end 210 of lead body 202, that are configured to be implanted in or adjacent to tissue, such as nervous tissue, muscle, ligament, and/or joint capsule. Lead body 202 is a suitable length for positioning the electrodes in or adjacent to target tissue while IPG is implanted in a suitable location, e.g., the lower back. For example, lead body 202 may be between about 30 and 80 cm in length, and preferably about 45 or about 65 cm in length. Lead body 202 is also of a suitable diameter for placement, for example, between about 1 and 2 mm in diameter and preferably about 1.3 mm. Electrodes 204, 206, 208, and 210 may be configured to stimulate the tissue at a stimulation frequency and at a level and duration sufficient to cause muscle to contract and may be ring electrodes, partial electrodes, segmented electrodes, nerve cuff electrodes placed around the nerve innervating the target muscle, or the like. Electrodes 204, 206, 208, 210 are a suitable length(s) and spaced apart a suitable distance along lead body 202. For example, electrodes 204, 206, 208, 210 may be about 2-5 mm in length, and preferably about 3 mm, and may be spaced apart about 2-6 mm, and preferably about 4 mm. As will also be understood by one of skill in the art, an electrode lead may contain more or fewer than four electrodes.

Also at distal end 210, first and second fixation elements 212 and 214 are coupled to lead body 202 via first and second fixation rings 216 and 218, respectively. First and second fixation elements 212 and 214 are configured to sandwich an anchor site, e.g., muscle, therebetween to secure electrode lead 200 at a target site without damaging the anchor site. First fixation elements 212 are angled distally relative to lead body 202, and resist motion in the first direction and prevent, in the case illustrated, insertion of the lead too far, as well as migration distally. Second fixation elements 214 are angled proximally relative to lead body 202 and penetrate through a tissue plane and deploy on the distal side of the tissue immediately adjacent to the target of stimulation. First fixation elements 212 are configured to resist motion in the opposite direction relative to second fixation elements 214. This combination prevents migration both proximally and distally, and also in rotation. In the illustrated embodiment, first fixation elements 212 are positioned between electrode 208 and distal most electrode 210 and second fixation element 214 is positioned between distal most electrode 210 and end cap 220. The length of and spacing between the fixation elements is defined by the structure around which they are to be placed. In one embodiment, the length of each fixation element is between about 1.5-4 mm and preferably about 2.5 mm and the spacing is between about 2 mm and 10 mm and preferably about 6 mm. First and second fixation elements 212 and 214 are configured to collapse inward toward lead body 202 in a delivery state and to expand, e.g., due to retraction of a sheath, in a deployed state. While FIG. 2 illustrates fixation elements 212 and 214 on lead body 202, it should be understood that other fixation elements may be used to anchor electrode lead 200 at a suitable location including the fixation elements described in U.S. Patent Application Pub. No. 2013/0131766 to Crosby and U.S. patent application Ser. No. 13/797,100, both assigned to the assignee of the present invention, the entire contents of each of which is incorporated herein by reference.

Lead body 202 further includes stylet lumen 222 extending therethrough. Stylet lumen 222 is shaped and sized to permit a stylet to be inserted therein, for example, during delivery of electrode lead 200. In one embodiment, end cap 220 is used to prevent the stylet from extending distally out of stylet lumen 222 beyond end cap 220.

At proximal end 224, electrode lead 200 includes contacts 226, 228, 230, and 232 separated along lead body 202 by spacers 234, 236, 238, 240, and 242. Contacts 226, 228, 230, and 232 may comprise an isodiametric terminal and are electrically coupled to electrodes 204, 206, 208, and 210, respectively, via, for example, individually coated spiral wound wires. A portion of proximal end 224 is configured to be inserted in IPG 300 and set-screw retainer 244 is configured to receive a screw from IPG 300 to secure the portion of electrode lead 200 within IPG 300.

As would be apparent to one of ordinary skill in the art, various electrode locations and configurations would be acceptable, including the possibility of skin surface electrodes. The electrode(s) may be an array of a plurality of electrodes, or may be a simple single electrode where the electrical circuit is completed with an electrode placed elsewhere (not shown) such as a skin surface patch or by the can of an implanted pulse generator. In addition, electrode lead 200 may comprise a wirelessly activated or leadless electrode, such as described in U.S. Pat. No. 8,321,021 to Kisker, such that no lead need be coupled to IPG 300.

Referring to FIG. 3A, IPG 300 is configured to generate pulses for electrical transmission to electrode lead 200. As is common with other active implantable medical devices, the IPG electronics are housed in a hermetically sealed metal housing 304. Housing 304 may comprise titanium or other biocompatible material, and includes connector block 302 that permits electrode lead 200 to be electrically coupled to the electronics within housing 304 via channel 306. Channel 306 is coupled to conductors 308, 310, 312, and 314 which are coupled to the IPG electronics. When proximal end 224 of electrode lead 200 is inserted within channel 306, conductors 308, 310, 312, and 314 are electrically coupled to contacts 226, 228, 230, and 232, respectively, and, in turn, electrically coupled to electrodes 204, 206, 208, and 210, respectively. Set-screw 316 is configured to be tightened down on set-screw retainer 244 to secure a portion of electrode lead 200 within channel 306. IPG 300 further includes a second channel (not shown) with four additional conductors. The two separate channels facilitate bilateral stimulation and the electrode configuration, e.g., combination of positive and negative electrodes, may be programmed independently for each channel.

As will be appreciated by one of ordinary skill in the art, while IPG 300 is illustratively implantable, a stimulator may be disposed external to a body of a patient on a temporary or permanent basis without departing from the scope of the present invention. For example, an external stimulator may be coupled to the electrodes wirelessly.

Figure 3B:
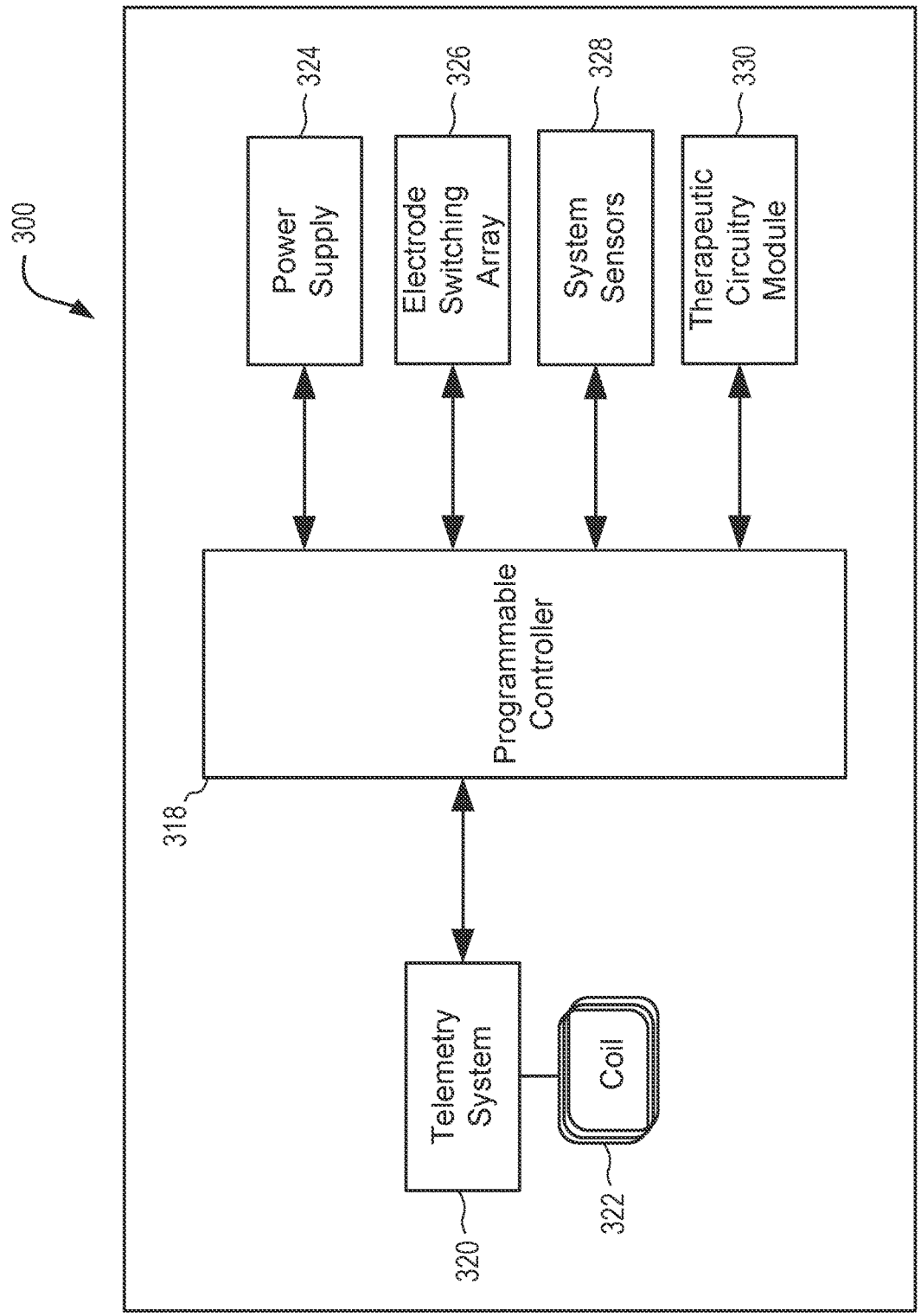
FIGS. 3B through 3D show alternative generalized block diagrams of the IPG of FIG. 3A, wherein the IPG of FIG. 3B has an inductive communications circuit, the IPG of FIG. 3C has a RF transceiver communications circuit, and the IPG of FIG. 3D has an inductive communications circuit and a RF transceiver communications circuit.

With respect to FIG. 3B, a generalized schematic diagram of the internal functional components of IPG 300 is now described. IPG 300 may include programmable controller 318, telemetry system 320 coupled to coil 322, power supply 324, electrode switching array 326, system sensors 328, and optional therapeutic circuitry module 330.

Controller 318 is electrically coupled to, and configured to control, the internal functional components of IPG 300. Controller 318 may comprise a commercially available microcontroller unit including a programmable microprocessor, volatile memory, nonvolatile memory such as EEPROM for storing programming, and nonvolatile storage, e.g., Flash memory, for storing firmware and a log of system operational parameters and patient data. The memory of controller 318 stores program instructions that, when executed by the processor of controller 318, cause the processor and the functional components of IPG 300 to provide the functionality ascribed to them herein. Controller 318 is configured to be programmable such that programming data is stored in the memory of controller 318 and may be adjusted using external programmer 500 as described below. Programming data may include pulse amplitude (voltage or current), pulse width, stimulation rate, stimulation frequency, ramp timing, cycle timing, session timing, and electrode configuration. In accordance with one embodiment, programmable parameters, their ranges, and nominal values are:

| Parameter | Min | Max | Nominal |
|---|---|---|---|
| Amplitude | 0 mA | 7.0 mA | 1 mA |
| Pulse Width | 25 µs | 500 µs | 200 µs |
| Rate | 1 Hz | 40 Hz | 20 Hz |
| On Ramp | 0 s | 5 s | 2 s |
| Off Ramp | | | |
| Cycle-On | 2 s | 20 s | 10 s |
| Cycle-Off | 20 s | 120 s | 20 s |
| Session | 1 min | 60 min | 30 min |

Controller 318 may be programmable to allow electrical stimulation between any chosen combination of electrodes on the lead, thus providing a simple bipolar configuration. In addition, controller 318 may be programmed to deliver stimulation pulses in a guarded bipolar configuration (more than 1 anode surrounding a central cathode) or IPG housing 304 may be programmed as the anode, enabling unipolar stimulation from any of the electrodes.

Controller 318 further may be programmed with a routine to calculate the impedance at electrode lead 200. For example, controller 318 may direct power supply 324 to send an electrical signal to one or more electrodes which emit electrical power. One or more other electrodes receive the emitted electrical power and send a received signal to controller 318 that runs the routine to calculate impedance based on the sent signal and the received signal.

Controller 318 is coupled to communications circuitry including telemetry system 320, which is electrically coupled to coil 322, that permits transmission of stimulation commands, and optionally power, between IPG 300 and activator 400 such that IPG 300 may be powered, programmed, and/or controlled by activator 400. For example, controller 318 may start or stop a treatment session responsive to stimulation commands received from a corresponding telemetry system and coil of activator 400 via coil 322 and telemetry system 320. Telemetry system 320 and coil 322 further permit transmission of programming data, and optionally power, between IPG 300 and external programmer 500 such that IPG 300 may be powered, programmed, and/or controlled by software-based programming system 600 via external programmer 500. For example, controller 318 may direct changes to at least one of pulse amplitude (voltage or current), pulse width, stimulation rate, stimulation frequency, ramp timing, cycle timing, session timing, and electrode configuration responsive to programming data received from a corresponding telemetry system and coil of external programmer 500 via coil 322 and telemetry system 320.

The technology for telemetry system 320 and coil 322 is well known to one skilled in the art and may include a magnet, a short range telemetry system, a longer range telemetry system (such as using MICS RF Telemetry available from Zarlink Semiconductor of Ottawa, Canada), or technology similar to a pacemaker programmer. Alternatively, coil 322 may be used to transmit power only, and separate radio frequency transmitters may be provided in IPG 300 activator 400, and/or external programmer 500 for establishing bidirectional or unidirectional data communication.

Power supply 324 powers the electrical components of IPG 300, and may comprise a primary cell or battery, a secondary (rechargeable) cell or battery or a combination of both. Alternatively, power supply 324 may not include a cell or battery, but instead comprise a capacitor that stores energy transmitted through the skin via a Transcutaneous Energy Transmission System (TETs), e.g., by inductive coupling. In a preferred embodiment, power supply 324 comprises a lithium ion battery.

Controller 318 further may be coupled to electrode switching array 326 so that any subset of electrodes of the electrode leads may be selectably coupled to therapeutic circuitry module 330, described in detail below. In this way, an appropriate electrode set may be chosen from the entire selection of electrodes implanted in the patient's body to achieve a desired therapeutic effect. Electrode switching array 326 preferably operates at high speed, thereby allowing successive stimulation pulses to be applied to different electrode combinations.

System sensors 328 may comprise one or more sensors that monitor operation of the systems of IPG 300, and log data relating to system operation as well as system faults, which may be stored in a log for later readout using software-based programming system 600. In one embodiment, system sensors 328 include a magnetic sensor configured to sense a magnetic field and to transmit a signal to controller 318 based on the sensed magnetic field such that the controller starts or stops a treatment session. In another embodiment, system sensors 328 include one or more sensors configured to sense muscle contraction and to generate a sensor signal based on the muscle contraction. Controller 318 is configured to receive the sensor signal from system sensors 328 and to adjust the stimulation parameters based on the sensor signal. In one embodiment, system sensors 328 sense an increase or decrease in muscle movement and controller 318 increases or decreases the stimulation frequency to maintain smooth and continuous muscle contraction.

In one embodiment, sensors 328 may include an accelerometer that senses acceleration of a muscle caused by muscle contraction. The accelerometer may be a 1-, 2- or 3-axis analog or digital accelerometer that determines whether the patient is active or asleep or senses overall activity of the patient, which may be a surrogate measure for clinical parameters (e.g., more activity implies less pain), and/or a heart rate or breathing rate (minute ventilation) monitor, e.g., which may be obtained using one or more of the electrodes disposed on the electrode leads. The accelerometer may be used to determine the orientation of IPG 300, and by inference the orientation of the patient, at any time. For example, after implantation, software-based programming system 600 may be used to take a reading from the implant, e.g., when the patient is lying prone, to calibrate the orientation of the accelerometer. If the patient is instructed to lie prone during therapy delivery, then the accelerometer may be programmed to record the orientation of the patient during stimulation, thus providing information on patient compliance. In other embodiments, system sensors 328 may include a pressure sensor, a movement sensor, and/or a strain gauge configured to sense muscle contraction and to generate a sensor signal based on the muscle contraction, and in a further embodiment, various combinations of at least one of an accelerometer, a pressure sensor, a movement sensor, and/or a strain gauge are included.

Sensors 328 may also include, for example, a humidity sensor to measure moisture within housing 304, which may provide information relating to the state of the electronic components, or a temperature sensor, e.g., for measuring battery temperature during charging to ensure safe operation of the battery. Data from the system sensors may be logged by controller 318 and stored in nonvolatile memory for later transmission to software-based programming system 600 via external programmer 500.

As will be appreciated by one of ordinary skill in the art, system sensors 328 may be placed in a variety of locations including within housing 302, within or adjacent to the tissue that is stimulated, and/or in proximity to the muscle to be contracted and connected via a separate lead to IPG 300. In other embodiments, sensors 324 may be integrated into one or more of the leads used for stimulation or may be an independent sensor(s) operatively coupled to IPG 300 using, for example, radio frequency (RF) signals for transmitting and receiving data.

Controller 318 also may be coupled to optional therapeutic circuitry module 330 that provides any of a number of complimentary therapeutic stimulation, analgesic, feedback or ablation treatment modalities as described in detail below. IPG 300 illustratively includes one therapeutic circuitry module 330, although additional circuitry modules may be employed in a particular embodiment depending upon its intended application, as described in U.S. Patent Application Publication No. 2011/0224665 to Crosby, assigned to the assignee of the present invention, the entire contents of which is incorporated herein by reference. Therapeutic circuitry module 330 may be configured to provide different types of stimulation, either to induce muscle contractions or to block pain signals in afferent nerve fibers; to monitor muscle contractions induced by stimulation and adjust the applied stimulation regime as needed to obtain a desired result; or to selectively and intermittently ablate nerve fibers to control pain and thereby facilitate muscle rehabilitation.

Figure 3C:
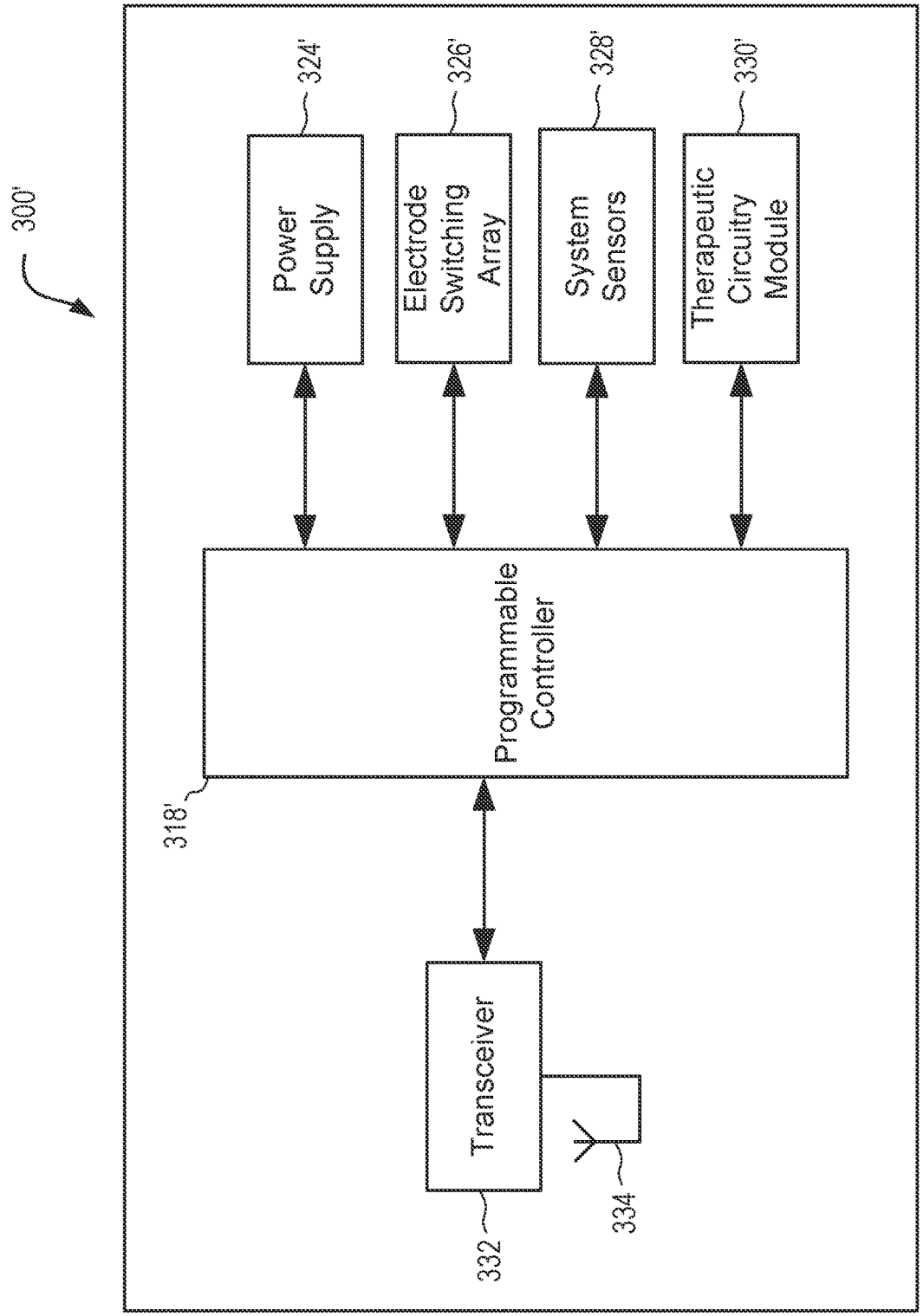

Referring to FIG. 3C, IPG 300' is constructed similarly to IPG 300 of FIG. 3B, wherein like components are identified by like-primed reference numbers. Thus, for example, power supply 324' in FIG. 3C corresponds to power supply 324 of FIG. 3B, etc. As will be observed by comparing FIGS. 3B and 3C, IPG 300' includes a communications circuit employing transceiver 332 coupled to antenna 334 (which may be inside or external to the hermetic housing) rather than telemetry system 320 and coil 322 of IPG 300.

Transceiver 332 preferably comprises a radio frequency (RF) transceiver and is configured for bi-directional communications via antenna 334 with a similar transceiver circuit disposed in activator 400 and/or external programmer 500. For example, transceiver 332 may receive stimulation commands from activator 400 and programming data from software-based programming system 600 via external programmer 500. Controller 318 may direct changes to at least one of pulse amplitude (voltage or current), pulse width, stimulation rate, stimulation frequency, ramp timing, cycle timing, session timing, and electrode configuration, including commands to start or stop a treatment session, responsive to programming data and/or stimulation commands received from a corresponding transceiver and antenna of activator 400 and/or external programmer 500 via antenna 334 and transceiver 332. Transceiver 332 also may include a low power mode of operation, such that it periodically awakens to listen for incoming messages and responds only to those messages including the unique device identifier assigned to that IPG. In addition, transceiver 332 may employ an encryption routine to ensure that messages sent from, or received by, IPG 300 cannot be intercepted or forged.

Figure 3D:
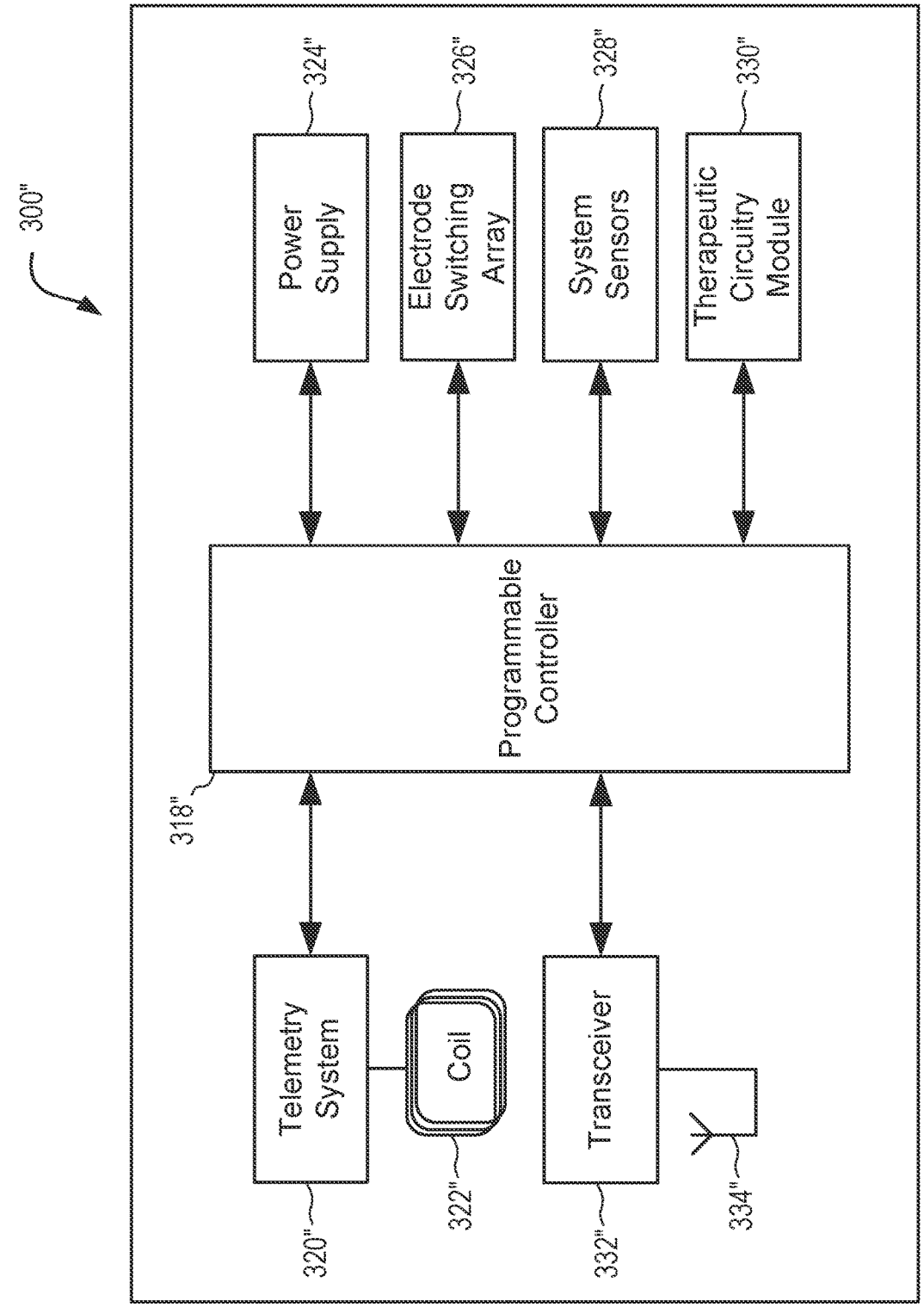

Referring to FIG. 3D, IPG 300" is constructed similarly to IPG 300 of FIG. 3B and IPG 300' of FIG. 3C except that IPG 300" includes a communications circuit employing telemetry system 320" and coil 322" and a communications circuit employing transceiver 332" and antenna 334". IPG 300" is preferably in an embodiment where IPG 300" communicates inductively and using RF. In one embodiment, telemetry system 320" and coil 322" are configured to transfer stimulation commands, and optionally power, between IPG 300" and activator 400 from a corresponding telemetry system and coil of activator 400. In such an embodiment, transceiver 332" and antenna 334" are configured to transfer programming data between IPG 300" and external programmer 500' from a corresponding transceiver and antenna of external programmer 500'. In an alternative embodiment, telemetry system 320" and coil 322" permit transfer of programming data, and optionally power, between IPG 300" and external programmer 500 from a corresponding telemetry system and coil of external programmer 500. In such an embodiment, transceiver 332" and antenna 334" are configured for transfer of stimulation commands between IPG 300" and activator 400' from a corresponding transceiver and antenna of activator 400'.

Figure 4A:
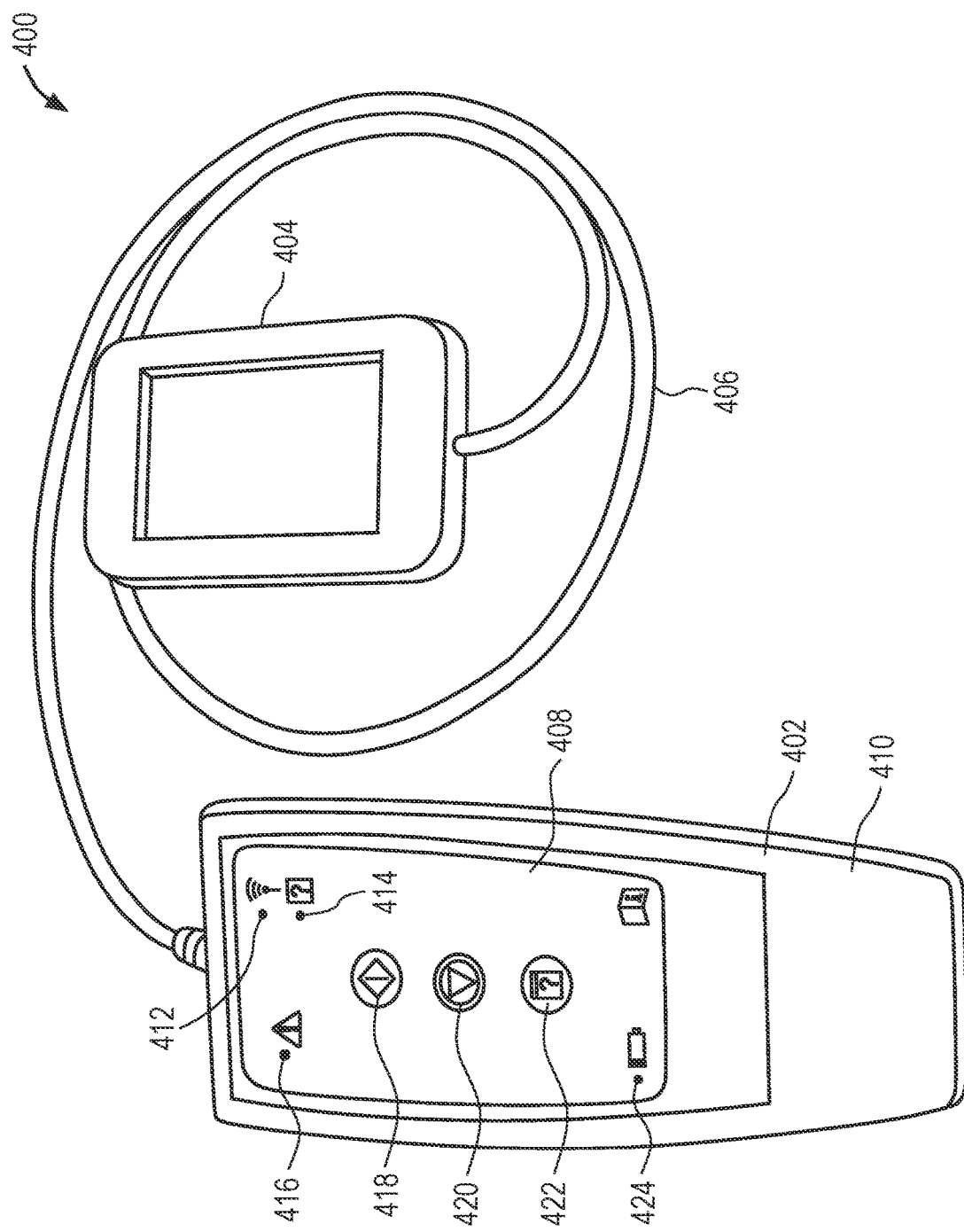
FIG. 4A shows an exemplary activator of the stimulator system of FIG. 1A.

Referring now to FIG. 4A, exemplary activator 400, including control module 402 and pad 404, is described. Control module 402 includes housing 410 sized for handheld use and user interface 408. User interface 408 permits a user, e.g., patient, physician, caregiver, to adjust a limited number of operational parameters of IPG 300 including starting and stopping a treatment session. Illustratively, user interface 408 includes signal LED 412, status LED 414, warning LED 416, start button 418, stop button 420, status button 422, and battery LED 424. Signal LED 412 preferably contains multiple diodes, each of which emit light of a different preselected color. Signal LED 412 is configured to illuminate when the communications circuit within pad 404 detects a suitable connection with a the corresponding communications circuit in IPG 300 suitable for power transmission and/or data communication between IPG 300 and activator 400. In one embodiment, signal LED 412 illuminates a red diode when there is not a suitable connection, a yellow diode when the connection is suitable but weak, and a green diode when the connection is suitable and strong. Status LED 414 also may include multiple diodes that illuminate in a pattern of flashes and/or colors to indicate to the user the status of IPG 300. Such patterns are stored in the memory of the controller of control module 402 and may indicate whether the IPG is directing stimulation to occur or awaiting commands. A user may refer to a user manual to decode a pattern shown on status LED 414. Warning LED 416 is configured to illuminate when the controller of control module 402 detects an error and indicates that a user should contact their physician or clinic. When start button 418 is pressed, the controller of control module 402 directs a signal to be sent to IPG 300 via pad 404 and cable 406 to begin a treatment session. When stop button 420 is pressed, the controller of control module 402 directs a signal to be sent to IPG 300 via pad 404 and cable 406 to end a treatment session. Alternatively, the treatment session may have a predetermined length and the controller de-energizes the electrodes when the session time expires. Battery LED 424 is configured to illuminate when the controller in control module 402 detects that the battery levels are below a predetermined threshold.

Pad 404 is configured to communicate information and, optionally, transfer power from control module 402 to IPG 300 in a bidirectional manner across a patient's skin. In one embodiment, pad 404 includes an inductive coil within its housing. Cable 406 is a suitable length so that a patient may comfortably place pad 404 in extracorporeal proximity to IPG 300 implanted in the patient's lower back while viewing control module 402 to confirm correct placement using signal LED 412.

Figure 4B:
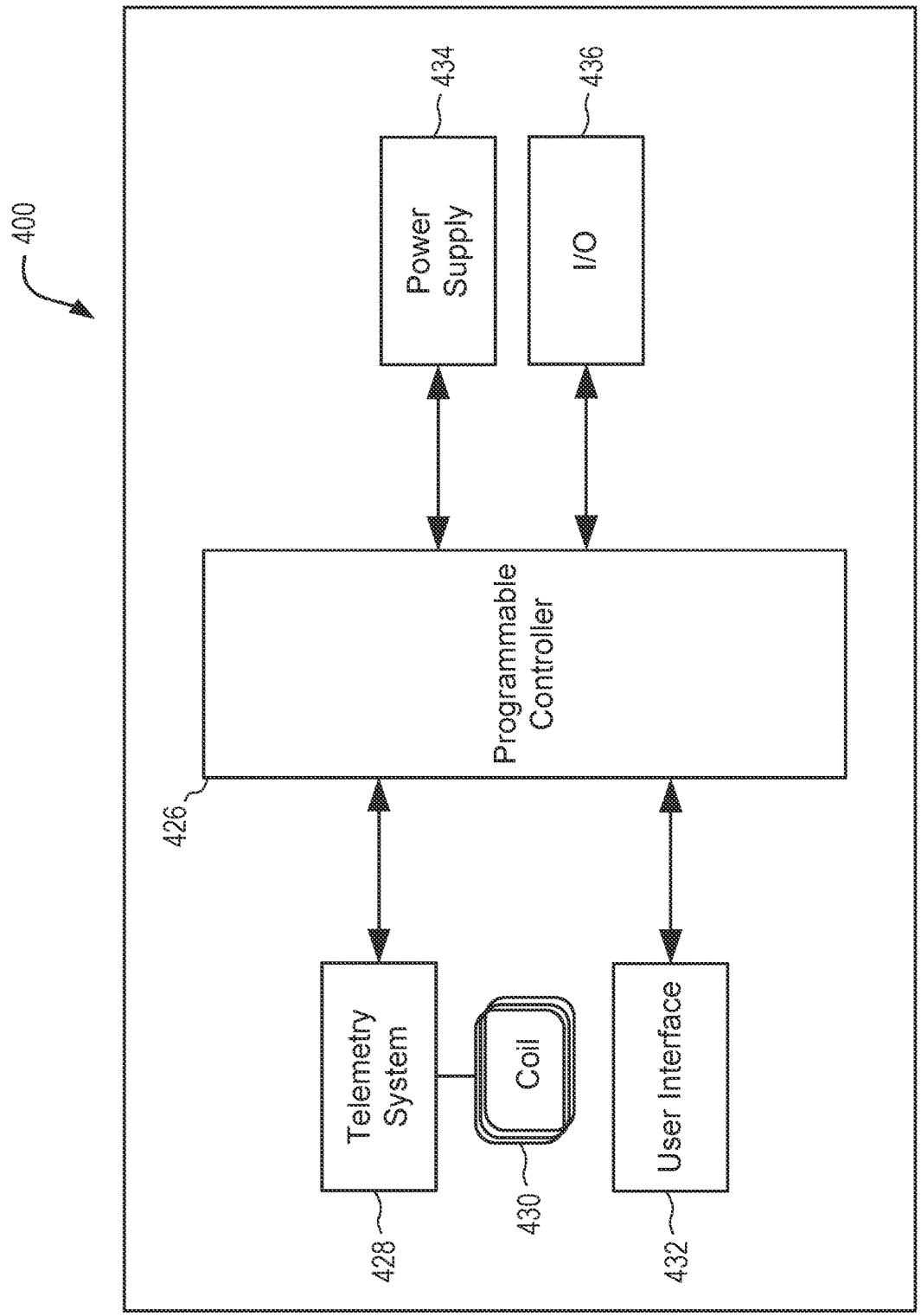
FIGS. 4B and 4C show alternative generalized block diagrams of the activator of FIG. 4A, wherein the activator of FIG. 4B has an inductive communications circuit and the activator of FIG. 4C has a RF transceiver communications circuit.

With respect to FIG. 4B, a generalized schematic diagram of the internal functional components of activator 400 is now described. Activator 400 may include programmable controller 426, telemetry system 428 coupled to coil 430, user interface 432, power supply 434, and input and output circuitry (I/O) 436. In a preferred embodiment, programmable controller 426, telemetry system 428, user interface 432, power supply 434, and input and output circuitry (I/O) 436 are housed within control module housing 410 and coil 430 is housed within the housing for pad 404.

Controller 426 is electrically coupled to, and configured to control, the internal functional components of activator 400. Controller 426 may comprise a commercially available microcontroller unit including a programmable microprocessor, volatile memory, nonvolatile memory such as EEPROM for storing programming, and nonvolatile storage, e.g., Flash memory, for storing firmware and a log of system operational parameters and patient data. The memory of controller 426 may store program instructions that, when executed by the processor of controller 426, cause the processor and the functional components of activator 400 to provide the functionality ascribed to them herein. Controller 426 is configured to be programmable. For example, controller 426 may send stimulation commands responsive to user input received at user interface 432 to controller 318 of IPG 300 via the telemetry (or RF) systems to start or stop a treatment session. In a preferred embodiment, a limited number of stimulation parameters may be adjusted at user interface 432 to minimize the chance of injury caused by adjustments made by non-physician users. In an alternative embodiment, controller 426 also may send adjustments to stimulation parameters, e.g., pulse amplitude (voltage or current), pulse width, stimulation rate, stimulation frequency, ramp timing, cycle timing, session timing, and electrode configuration to IPG 300 responsive to user input received at user interface 432.

Controller 426 is coupled to telemetry system 428, which is electrically coupled to coil 430 (e.g., via cable 406), that permits transmission of energy and stimulation commands between activator 400 and IPG 300 (or IPG 300") such that IPG 300 may be powered, programmed, and/or controlled by activator 400 responsive to user input received at user interface 432. For example, controller 426 may direct telemetry system 428 and coil 430 to send adjustments to stimulation parameter(s), including commands to start or stop a treatment session or provide status of the IPG, responsive to user input received at user interface 432 to coil 322 and telemetry system 320 of IPG 300. The technology for telemetry system 428 and coil 430 is well known to one skilled in the art and may be similar to telemetry system 320 and coil 322 described above. Alternatively, coil 430 may be used to transmit power only, and separate radio frequency transmitters may be provided in activator 400 and IPG 300 for establishing bidirectional or unidirectional data communication.

User interface 432 is configured to receive user input and to display information to the user. As described above, user interface 432 may include buttons for receiving user input and LEDs for displaying information to the user. As will be readily apparent to one skilled in the art, user interface 432 is not limited thereto and may use a display, a touch screen, a keypad, a microphone, a speaker, a trackball, or the like.

Power supply 434 powers the electrical components of activator 400, and may comprise a primary cell or battery, a secondary (rechargeable) cell or battery or a combination of both. Alternatively, power supply 434 may be a port to allow activator 400 to be plugged into a conventional wall socket for powering components.

Input and output circuitry (I/O) 436 may include ports for data communication such as wired communication with a computer and/or ports for receiving removable memory, e.g., SD card, upon which program instructions or data related to activator 400 use may be stored.

Figure 4C:
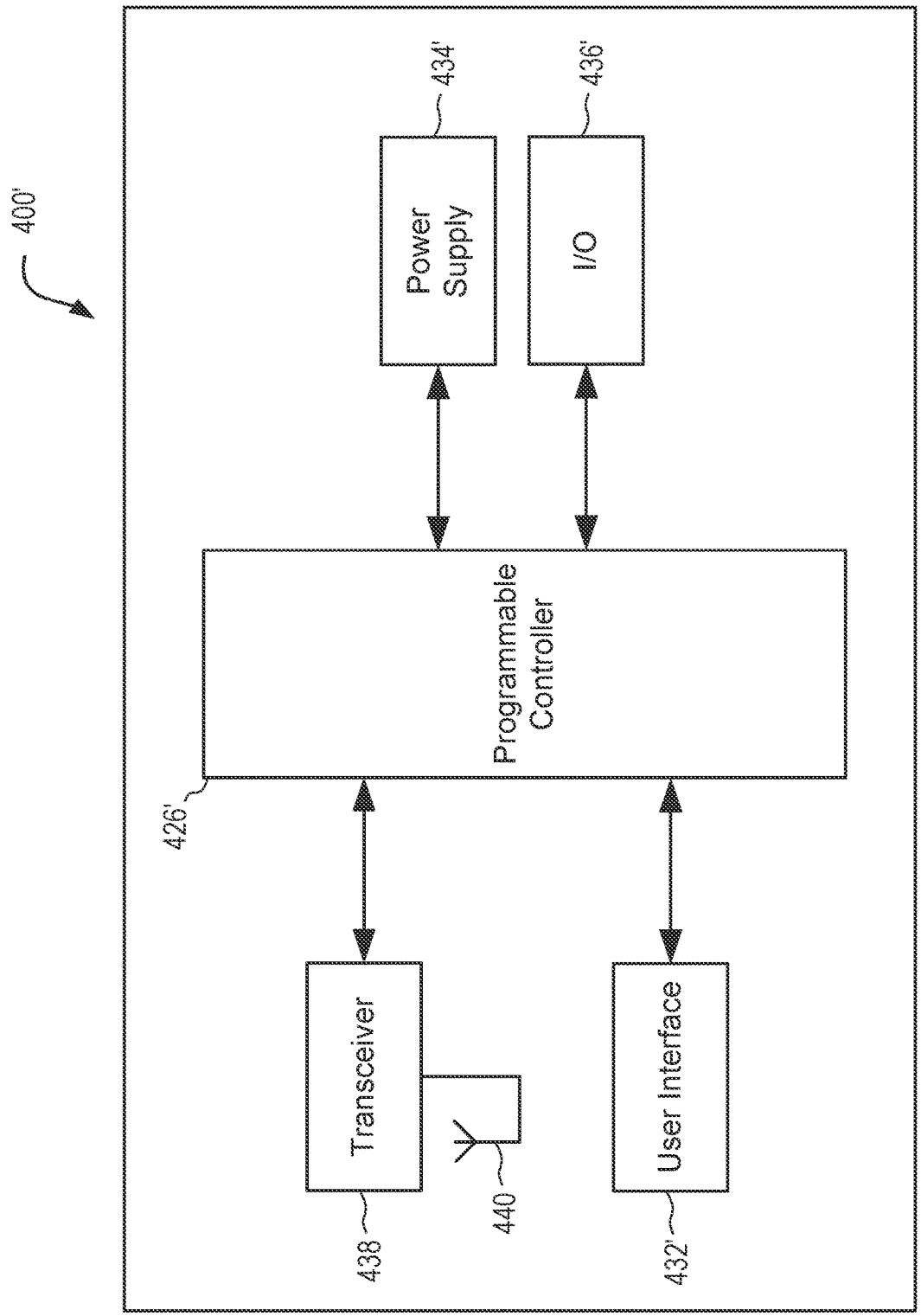

Referring to FIG. 4C, activator 400' is constructed similarly to activator 400 of FIG. 4B except that activator 400' includes a communications circuit employing transceiver 438 and antenna 440 rather than a communications circuit employing telemetry system 428 and coil 430. Transceiver 438 preferably comprises a radio frequency (RF) transceiver and is configured for bi-directional communications via antenna 440 with transceiver 332 via antenna 334 of IPG 300'. Transceiver 438 may transmit stimulation commands from activator 400' to IPG 300' (or IPG 300"). For example, controller 426' may direct transceiver 438 to transmit commands to start or stop a treatment session to IPG 300' responsive to user input received at user interface 432'. In one embodiment, controller 426' may direct transceiver 438 to transmit a command to provide status of IPG 300' or commands to adjust stimulation parameter(s) to IPG 300' responsive to user input received at user interface 432'.

Transceiver 438 also may include a low power mode of operation, such that it periodically awakens to listen for incoming messages and responds only to those messages including the unique device identifier assigned to that activator. In addition, transceiver 438 may employ an encryption routine to ensure that messages sent from, or received by, activator 400' cannot be intercepted or forged.

Figure 5A:
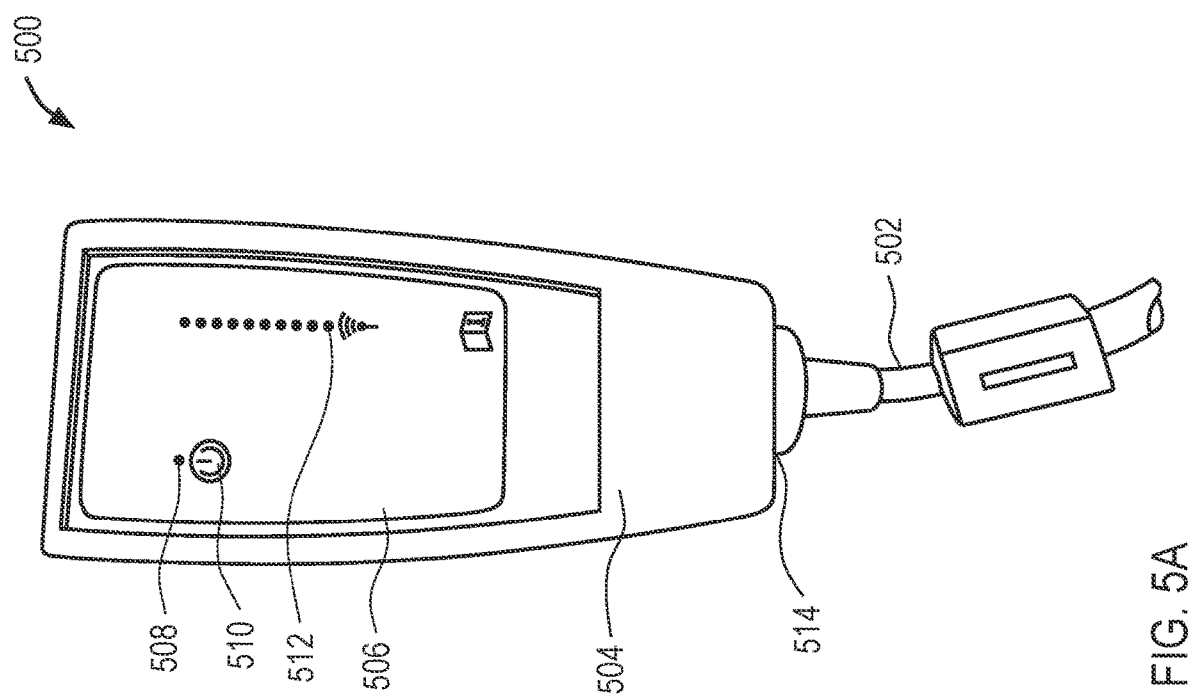
FIG. 5A shows an exemplary external programmer of the stimulator system of FIG. 1A.

Referring now to FIG. 5A, exemplary external programmer 500 is now described. External programmer 500 includes housing 504 sized for handheld use and user interface 506. User interface 506 permits a user, e.g., patient, physician, caregiver, to send programming data to IPG 300 including commands to adjust stimulation parameters. Illustratively, user interface 506 includes status LED 508, status button 510, and signal LEDs 512. Status LED 508 is configured to illuminate when status button 510 is pressed to indicate a successful communication has been sent to IPG 300, e.g., command to stop a treatment session. Signal LEDs 512 are configured to illuminate based on the strength of the signal between IPG 300 and external programmer 500. The controller of external programmer 500 may direct appropriate signal LEDs 512 to illuminate based on the strength of the signals between the respective telemetry systems and coils or transceivers and antennas of external programmer 500 and IPG 300. Signal LEDs 512 may include diodes with different colors. For example, signal LEDs 512 may include red diodes configured to illuminate when the signal strength between external programmer 500 and IPG 300 is weak or non-existent, yellow diodes configured to illuminate when the signal strength between external programmer 500 and IPG 300 is medium, and green diodes configured to illuminate when the signal strength between external programmer 500 and IPG 300 is strong. External programmer 500 further includes port 514 configured to receive cable 502 such that external programmer 500 is electrically coupled and may communicate programming data with software-based programming system 600 run on a computer.

Figure 5B:
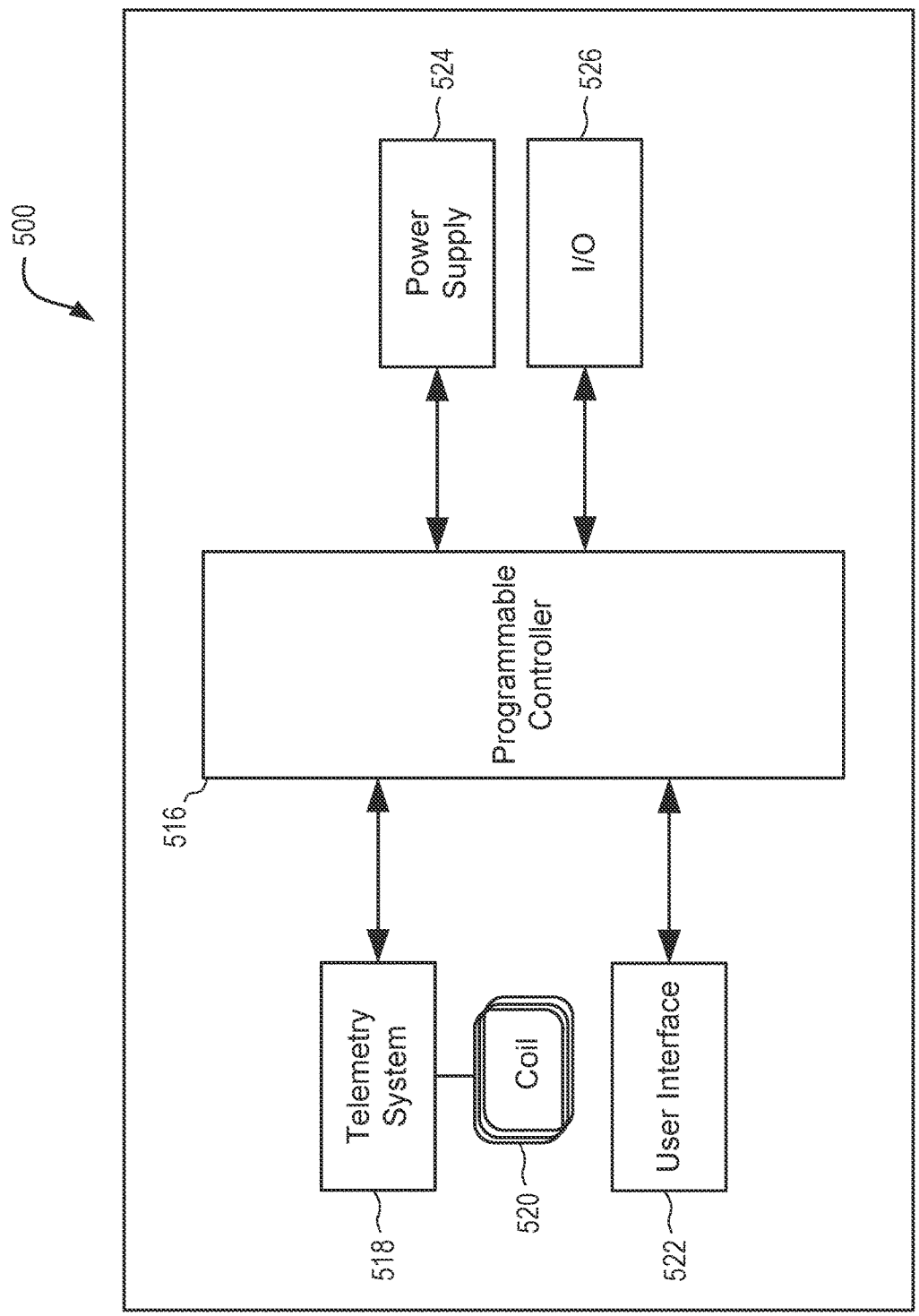
FIGS. 5B and 5C show alternative generalized block diagrams of the external programmer of FIG. 5A, wherein the external programmer of FIG. 5B has an inductive communications circuit and the external programmer of FIG. 5C has a RF transceiver communications circuit.

With respect to FIG. 5B, a generalized schematic diagram of the internal functional components of external programmer 500 is now described. External programmer 500 may include programmable controller 516, telemetry system 518 coupled to coil 520, user interface 522, power supply 524, and input and output circuitry (I/O) 526.

Controller 516 is electrically coupled to, and configured to control, the internal functional components of external programmer 500. Controller 516 may comprise a commercially available microcontroller unit including a programmable microprocessor, volatile memory, nonvolatile memory such as EEPROM for storing programming, and nonvolatile storage, e.g., Flash memory, for storing firmware and a log of system operational parameters and patient data. The memory of controller 516 may store program instructions that, when executed by the processor of controller 516, cause the processor and the functional components of external programmer 500 to provide the functionality ascribed to them herein. Controller 516 is configured to be programmable such that stimulation parameters, e.g., pulse amplitude (voltage or current), pulse width, stimulation rate, stimulation frequency, ramp timing, cycle timing, session timing, and electrode configuration may be adjusted responsive to user input received at user interface 522. For example, controller 516 may send programming data responsive to user input received at user interface 522 to controller 318 of IPG 300 via the respective telemetry (or RF) systems to adjust stimulation parameters or to start or stop a treatment session. In a preferred embodiment, only a physician has access to external programmer 500 to minimize the chance of injury caused by adjustments made by non-physician users.

Controller 516 is coupled to telemetry system 518, which is electrically coupled to coil 520, that permits transmission of programming data, and optionally power, between software-based programming system 600 and IPG 300 (or IPG 300") via external programmer 500. In this manner, IPG 300 may be powered, programmed, and/or controlled by software-based programming system 600 and external programmer 500 responsive to user input received at user interface 522. For example, controller 516 may direct telemetry system 518 to transmit stimulation parameter(s) such as pulse amplitude (voltage or current), pulse width, stimulation rate, stimulation frequency, ramp timing, cycle timing, session timing, and electrode configuration, including commands to start or stop a treatment session, to IPG 300 responsive to user input received at user interface 522 and/or software-based programming system 600. As another example, controller 516 may direct telemetry system 518 to transmit interrogation commands such as requests for the actual value of stimulation parameter(s), battery voltage, data logged at IPG 300, and IPG 300 status data, to IPG 300 responsive to user input received at user interface 522 and/or software-based programming system 600, and to receive responses to the interrogation commands from IPG 300. As yet another example, controller 516 may direct telemetry system 518 to transmit commands to IPG 300 to calculate the impedance of electrode lead 200 using a routine stored on controller 318 of IPG 300 and to receive the calculated lead impedance from the telemetry system of IPG 300. The technology for telemetry system 518 and coil 520 is well known to one skilled in the art and may be similar to telemetry system 320 and coil 322 described above. Alternatively, coil 520 may be used to transmit power only, and separate radio frequency transmitters may be provided in external programmer 500 and IPG 300 for establishing directional data communication.

User interface 522 is configured to receive user input and to display information to the user. As described above, user interface 522 may include buttons for receiving user input and LEDs for displaying information to the user. As will be readily apparent to one skilled in the art, user interface 522 is not limited thereto and may use a display, a touch screen, a keypad, a microphone, a speaker, a trackball, or the like.

Power supply 524 powers the electrical components of external programmer 500, and may comprise a primary cell or battery, a secondary (rechargeable) cell or battery or a combination of both. Alternatively, power supply 524 may be a port to allow external programmer 524 to be plugged into a conventional wall socket for powering components. In one preferred embodiment, power supply 524 comprises a USB port and cable that enables external programmer 500 to be powered from a computer, e.g., via cable 502, running software-based programming system 600.

Input and output circuitry (I/O) 526 may include ports for data communication such as wired communication with a computer and/or ports for receiving removable memory, e.g., SD card, upon which program instructions or data related to external programmer 500 use may be stored. In one embodiment, I/O 526 comprises port 514, and corresponding circuitry, for accepting cable 502 such that external programmer 500 is electrically coupled to a computer running software-based programming system 600.

Figure 5C:
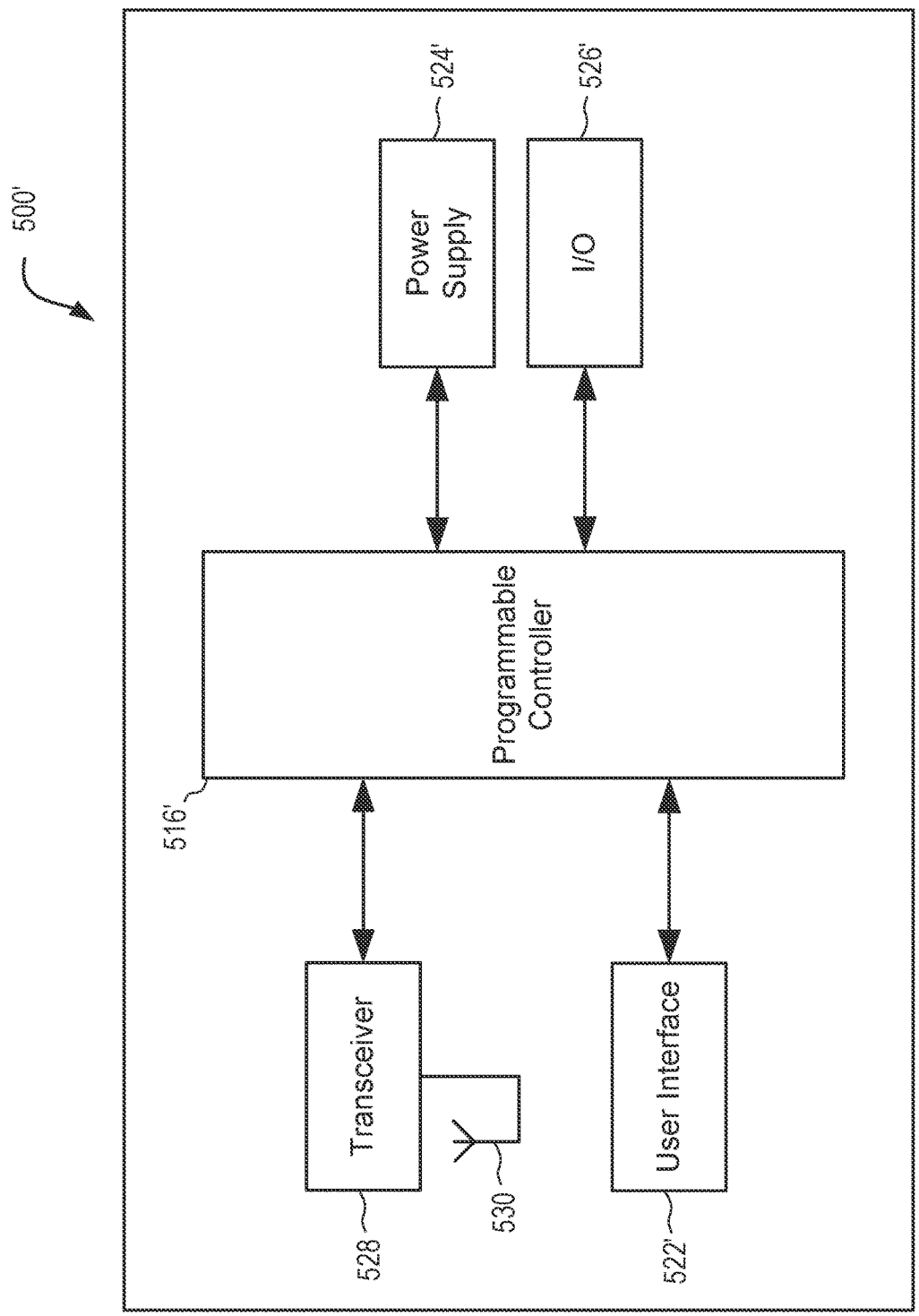

Referring to FIG. 5C, external programmer 500' is constructed similarly to external programmer 500 of FIG. 5B except that external programmer 500' includes a communications circuit employing transceiver 528 and antenna 530 rather than a communications circuit employing telemetry system 518 and coil 520. Transceiver 528 preferably comprises a radio frequency (RF) transceiver and is configured for bi-directional communications via antenna 530 with transceiver 332 via antenna 334 of IPG 300'. Transceiver 528 may transmit programming data from external programmer 500' to IPG 300' (or IPG 300"). For example, controller 516' may direct transceiver 528 to transmit stimulation parameter(s) such as pulse amplitude (voltage or current), pulse width, stimulation rate, stimulation frequency, ramp timing, cycle timing, session timing, and electrode configuration, including commands to start or stop a treatment session, to IPG 300' responsive to user input received at user interface 522' and/or software-based programming system 600. As another example, controller 516' may direct transceiver 528 to transmit interrogation commands such as requests for the actual value of stimulation parameter(s), battery voltage, data logged at IPG 300', and IPG 300' status data, to IPG 300' responsive to user input received at user interface 522' and/or software-based programming system 600, and to receive responses to the interrogation commands from IPG 300'. As yet another example, controller 516' may direct transceiver 528 to transmit commands to IPG 300' to calculate the impedance of electrode lead 200 using a routine stored on controller 318' of IPG 300' and to receive the calculated lead impedance from transceiver 332 of IPG 300'.

Transceiver 528 also may include a low power mode of operation, such that it periodically awakens to listen for incoming messages and responds only to those messages including the unique device identifier assigned to that external programmer. In addition, transceiver 528 may employ an encryption routine to ensure that messages sent from, or received by, external programmer 500' cannot be intercepted or forged.

Figure 6:
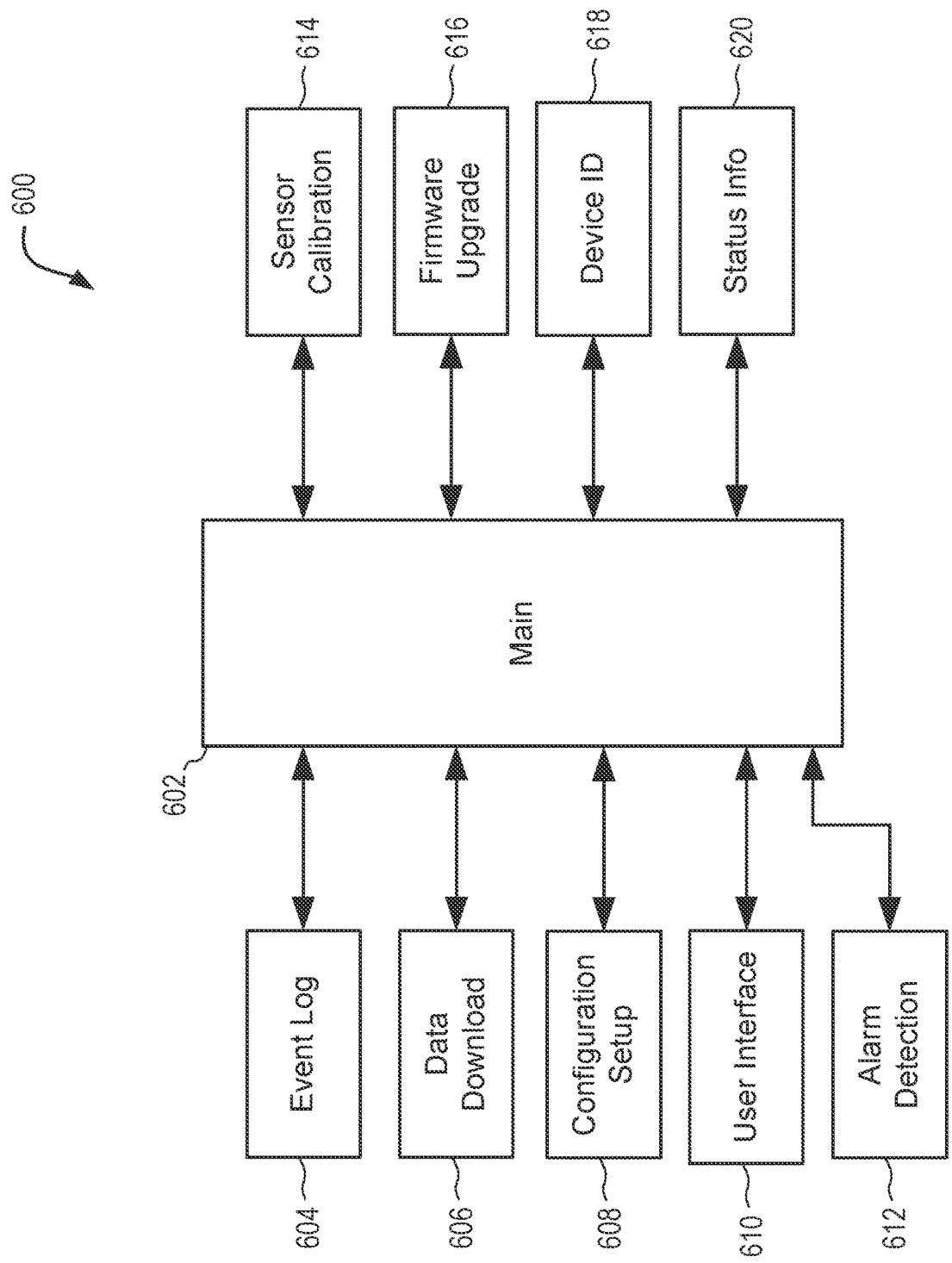
FIG. 6 is a block diagram of the functional components of an exemplary software-based programming system of the stimulator system of FIG. 1A.

Referring now to FIG. 6, the software implementing programming system 600 is now described. The software of programming system 600 comprises a number of functional blocks, schematically depicted in FIG. 6, including main block 602, event logging block 604, data download block 606, configuration setup block 608, user interface block 610, alarm detection block 612, sensor calibration block 614, firmware upgrade block 616, device identifier block 618, and status information block 620. The software preferably is written in C++ and employs an object oriented format. In one preferred embodiment, the software is configured to run on top of a Microsoft Windows™ (a registered trademark of Microsoft Corporation, Redmond, Wash.) or Unix-based operating system, such as are conventionally employed on desktop and laptop computers. The computer running programming system 600 preferably includes a data port, e.g., USB port or comparable wireless connection, that permits external programmer 500 and/or activator 400 to be coupled thereto. Alternatively, as discussed above, the computer may include a wireless card, e.g., conforming to the IEEE 802.11 standard, thereby enabling IPG 300, activator 400, and/or external programmer 500 to communicate wirelessly with the computer running programming system 600. As a further alternative, IPG 300, activator 400, and/or external programmer 500 may include a communications circuit(s) having telephony circuitry, e.g., GSM, CDMA, LTE circuitry, or the like, that automatically dials and uploads data, such as alarm data, from IPG 300 to a secure website accessible by the patient's physician.

Main block 602 preferably includes a main software routine that executes on the physician's computer, and controls overall operation of the other functional blocks. Main block 602 enables the physician to download event data and alarm information stored on IPG 300, via external programmer 500, to his office computer, and also permits programming system 600 to directly control operation of IPG 300, via external programmer 500. Main block also enables the physician to upload firmware updates and configuration data to IPG 300 via external programmer 500.

Event Log block 604 is a record of operational data downloaded from IPG 300, using external programmer 500, and may include, for example, treatment session start and stop times, current stimulation parameters, stimulation parameters from previous treatment sessions, sensor data, lead impedance, battery current, battery voltage, battery status, and the like. The event log also may include the occurrence of events, such as alarms or other abnormal conditions.

Data Download block 606 is a routine that commands IPG 300, using external programmer 500, to transfer data to programming system 600 for download after IPG 300 is coupled to the computer programming system 600 via external programmer 500. Data Download block 606 may initiate, either automatically or at the instigation of the physician via user interface block 610, downloading of data stored in the event log.

Configuration Setup block 608 is a routine that configures the parameters stored within IPG 300, using external programmer 500, that control operation of IPG 300. The interval timing parameters may determine, e.g., how long the processor remains in sleep mode prior to being awakened to listen for radio communications or to control IPG 300 operation. The interval timing parameters may control, for example, the duration of a treatment session. Interval timing settings transmitted to IPG 300 from programming system 600 also may determine when and how often event data is written to the memory in controller 318. In an embodiment in which external programmer 500 is also configured to transfer data to activator 400, programming system 600 also may be used to configure timing parameters used by the firmware executed by controller 426 of activator 400. Block 608 also may be used by the physician to configure parameters stored within the memory of controller 318 relating to limit values on operation of controller 318. These values may include times when IPG 300 may and may not operate, etc. Block 608 also may configure parameters store within the memory of controller 318 relating to control of operation of IPG 300. These values may include target numbers of treatment sessions and stimulation parameters.

User interface block 610 handles display of information retrieved from the programming system 600 and IPG 300, via external programmer 500, and data download block 606, and presents that information in an intuitive, easily understood format for physician review. Such information may include status of IPG 300, treatment session start and stop times, current stimulation parameters, stimulation parameters from previous treatment sessions, sensor data, lead impedance, battery status, and the like. User interface block 610 also generates user interface screens that permit the physician to input information to configure the session timing, stimulation parameters, requests to calculate lead impedance, etc.

Alarm detection block 612 may include a routine for evaluating the data retrieved from IPG 300, using external programmer 500, and flagging abnormal conditions for the physician's attention. For example, alarm detection block 612 may flag when a parameter measured by system sensors 328 is above or below a predetermined threshold.

Sensor calibration block 614 may include a routines for testing or measuring drift, of system sensors 328 employed in IPG 300, e.g., due to aging or change in humidity. Block 614 may then compute offset values for correcting measured data from the sensors, and transmit that information to IPG 300 for storage in the nonvolatile memory of controller 318.

Firmware upgrade block 616 may comprise a routine for checking the version numbers of the controller firmware installed on IPG 300, using external programmer 500, and identify whether upgraded firmware exists. If so, the routine may notify the physician and permit the physician to download revised firmware to IPG 300, in nonvolatile memory.

Device identifier block 618 consists of a unique identifier for IPG 300 that is stored in the nonvolatile memory of controller 318 and a routine for reading that data when programming system 600 is coupled to IPG 300 via external programmer 500. The device identifier also may be used by IPG 300 to confirm that wireless communications received from activator 400 and/or external programmer 500 are intended for that specific IPG. Likewise, this information is employed by activator 400 and/or external programmer 500 to determine whether a received message was generated by the IPG associated with that system. Finally, the device identifier information may be employed by programming system 600 to confirm that activator 400 and IPG constitute a matched set.

Status information block 620 comprises a routine for interrogating IPG 300, when connected via activator 400, or external programmer 500 and programming system 600, to retrieve current status data from IPG 300, using external programmer 500. Such information may include, for example, battery status, stimulation parameters, lead impedance, the date and time on the internal clocks of treatment sessions, version control information for the firmware and hardware currently in use, and sensor data.

Figure 7A:
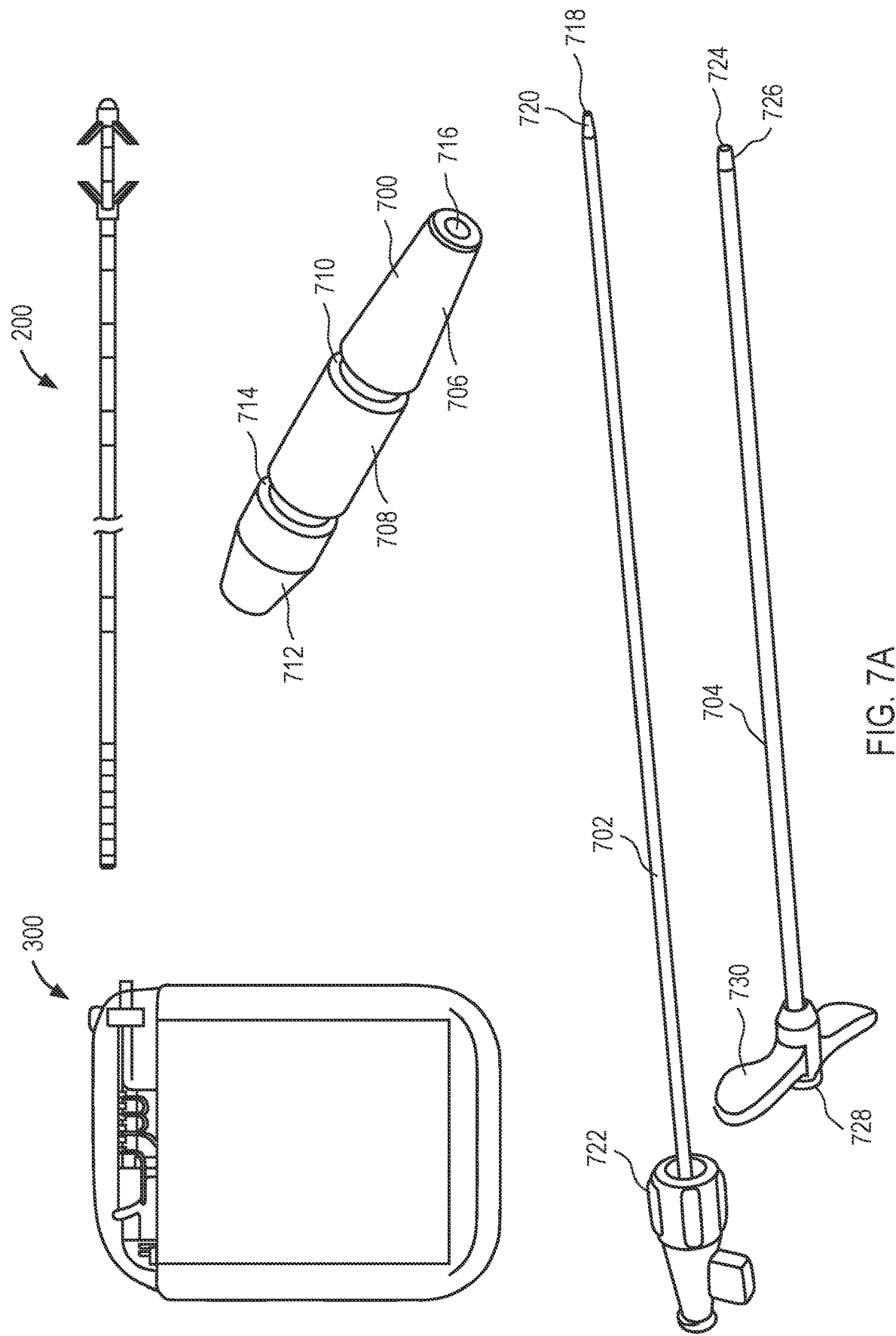

Referring now to FIGS. 7A to 7D, an exemplary method for implanting an electrode lead and IPG is described. First, electrode lead 200, IPG 300, stylet (now shown), suture sleeve 700, introducer 702, and dilator 704 are provided, as shown in FIG. 7A. In FIG. 7A, components of the system are not depicted to scale on either a relative or absolute basis. Suture sleeve 700 illustratively includes first end section 706, middle section 708 separated from first end section by first groove 710, second end section 712 separated from middle section 708 by second groove 714, and sleeve lumen 716. First and second end sections 706 and 712 may have truncated conical portions as shown. First and second grooves 710 and 714 are sized and shaped to accept sutures such that suture sleeve 700 may be secured to tissue, e.g., superficial fascia, using the sutures. Sleeve lumen 716 is sized such that electrode lead 200 may be inserted therethrough.

Introducer 702 may include introducer lumen 718, distal tip 720, and coupling portion 722. Introducer lumen 718 extends through introducer 702 and is shaped and sized to permit electrode lead 200 to slide therethrough. Distal tip 720 is beveled to ease introduction through tissue. Coupling portion 722, illustratively a female end with threads, is configured to be coupled to a portion of dilator 704. In one embodiment, introducer 702 comprises a commercially available 7 French (Fr) introducer.

Dilator 704 may include dilator lumen 724, distal tip 726, coupling portion 728, and handle 730. Dilator lumen 724 extends through dilator 704 and is shaped and sized to permit introducer 702 to slide therethrough. Distal tip 726 is beveled to ease introduction through tissue. Coupling portion 728, illustratively a male end with threads, is configured to be coupled to a portion of introducer 702, e.g., coupling portion 722. Handle 730 is sized and shaped to permit a physician to comfortably hold dilator 704.

Next, a stylet is inserted within the stylet lumen of electrode lead 200 to provide additional stiffness to electrode lead 200 to ease passage of electrode lead 200 through introducer 702. The stylet may be a commercially available stylet such as a locking stylet available from Cook Group Incorporated of Bloomington, Indiana. Electrode lead 200 then is inserted within introducer lumen 718 of introducer 702.

Using fluoroscopy, acoustic, anatomic, or CT guidance, dilator 704 is delivered transcutaneously and transmuscularly to a target site, e.g., in or adjacent to tissue associated with control of the lumbar spine. Such tissue may include nervous tissue, muscle, ligament, and/or joint capsule. In one embodiment, muscle includes skeletal muscle such as the multifidus, transverse abdominus, quadratus lumborum, psoas major, internus abdominus, obliquus externus abdominus, and erector spinae muscles and nervous tissue includes a peripheral nerve that innervates skeletal muscle. In a preferred embodiment, nervous tissue comprises the dorsal ramus nerve, or fascicles thereof, that innervate the multifidus muscle.

Next, introducer 702 (having a portion of the electrode lead disposed therein) is inserted through dilator lumen 724 to the target site. Introducer 702 may then be coupled to dilator 704, e.g., by screwing coupling portion 722 onto coupling portion 728.

Figure 7B:
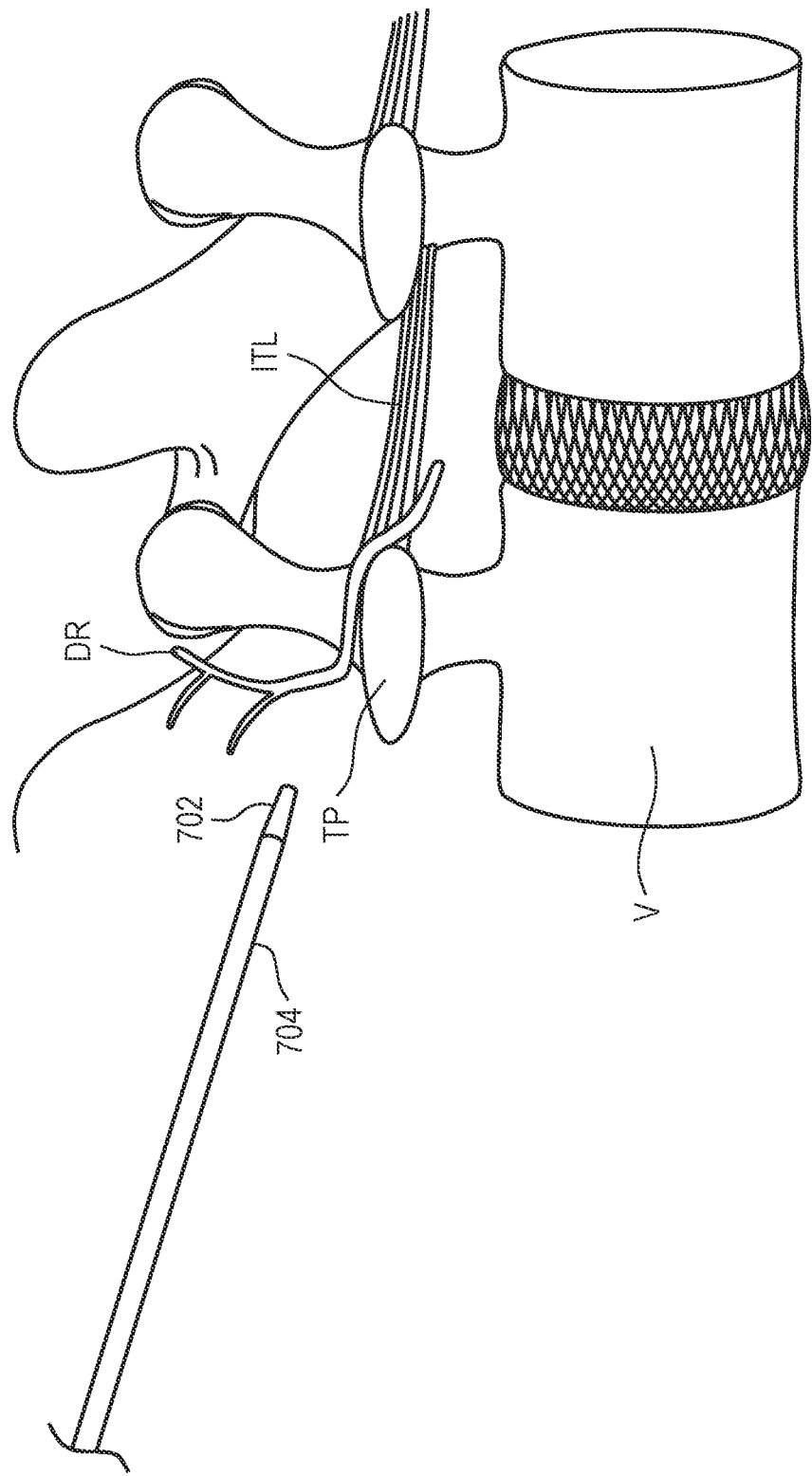
Figure 7C:
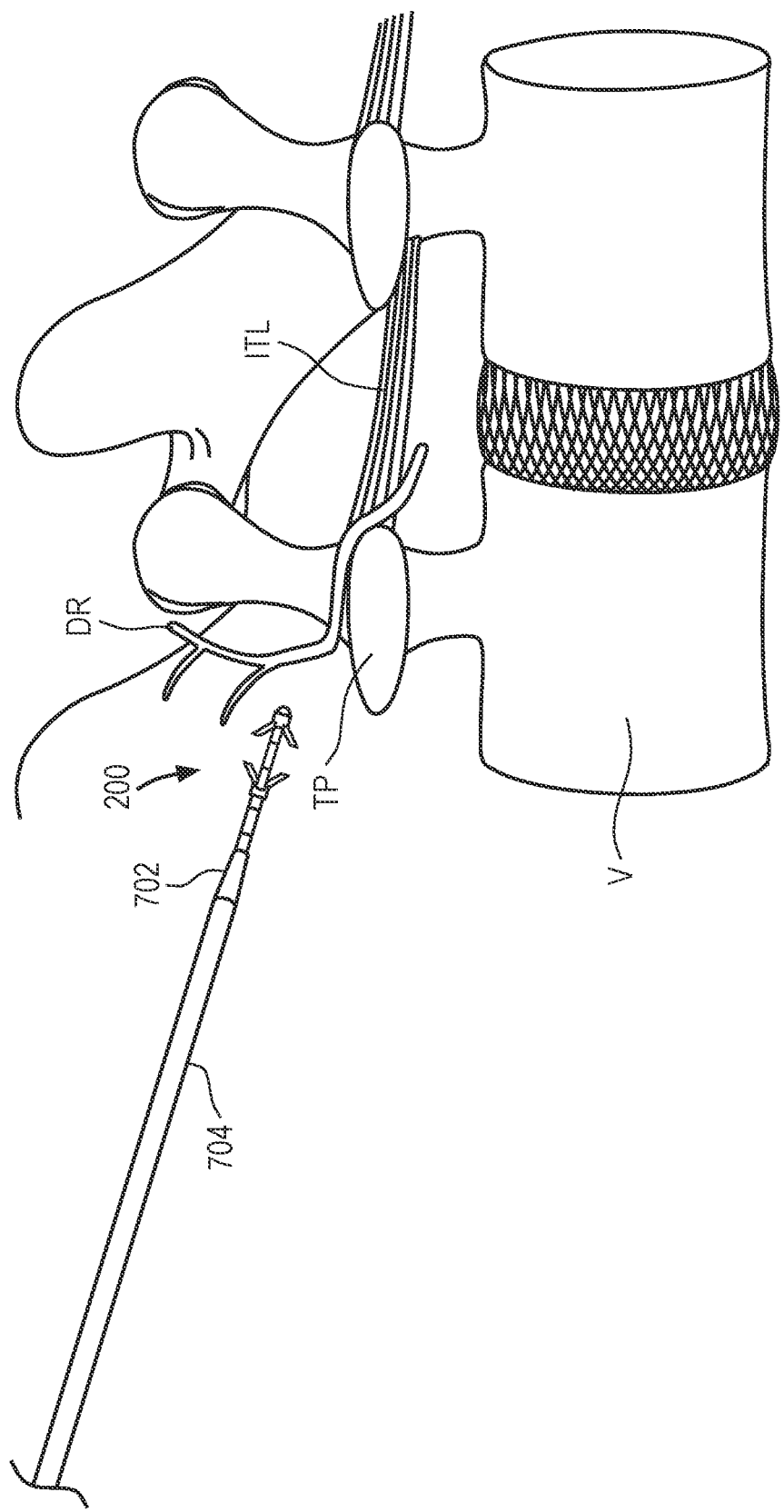

FIGS. 7B-7D depict a lateral projection of a segment of a typical human lumbar spine shown having a vertebral body V, transverse process TP, inter-transverse ligament ITL, and a dorsal ramus DR. In FIG. 7B, dilator 704 having introducer 702 disposed therethrough, which has a portion of the electrode lead disposed therein, are positioned adjacent to the target site, illustratively, the medial branch of the dorsal ramus DR nerve that innervates the multifidus muscle. In one embodiment, electrodes of the electrode lead are positioned to stimulate the medial branch of the dorsal ramus that exits between the L2 and L3 lumbar segments and passes over the transverse process of the L3 vertebra, thereby eliciting contraction of fascicles of the lumbar multifidus at the L3, L4, L5 and S1 segments and in some patients also at the L2 segment.

Introducer 702 and dilator 704 are moved proximally, e.g., using handle 730, while maintaining the position of electrode lead 200 at the target site, as shown in FIG. 7C. The first and second fixation elements of electrode lead 200 individually transition from a collapsed state within introducer 702 to an expanded state, shown in FIG. 7C, as introducer 702 passes over the respective fixation element. The first and second fixation elements sandwich an anchor site, e.g., muscle, therebetween without damaging the anchor site in the expanded state to fix electrode lead 200 at the target site.

Introducer 702 and dilator 704 are moved proximally off the proximal end of electrode lead 200 and suture sleeve 700 is placed over the proximal end of electrode lead 200 and moved distally, as illustrated in FIG. 7D. When suture sleeve 700 is positioned adjacent to the superficial fascia SF beneath skin SK, sutures are sewn into the first and second grooves of suture sleeve 700 so as to secure suture sleeve 700 to the superficial fascia SF.

Finally, the IPG is coupled to the proximal end of electrode lead 200 and implanted within the lower back of the patient.

Exemplary stimulation parameters in accordance with aspects of the present invention are now described. Preferably, such stimulation parameters are selected and programmed to induce contraction of muscle to restore neural control and rehabilitate muscle associated with control of the spine, thereby improving lumbar spine stability and reducing back pain. As used in this specification, "to restore muscle function" means to restore an observable degree of muscle function as recognized by existing measures of patient assessment, such as the Oswestry Disability Index ("ODI") as described in Lauridsen et al., *Responsiveness and minimal clinically important difference for pain and disability instruments in low back pain patients*, BMC Musculoskeletal Disorders, 7: 82-97 (2006), the European Quality of Life Assessment 5D ("EQ-5D") as described in Brazier et al., *A comparison of the EQ-5D and SF-6D across seven patient groups*, Health Econ. 13: 873-884 (2004), or a Visual Analogue Scale ("VAS") as described in Hagg et al., *The clinical importance of changes in outcome scores after treatment for chronic low back pain*, Eur Spine J 12: 12-20 (2003). In accordance with one aspect of the present invention, "to restore muscle function" means to observe at least a 15% improvement in one of the foregoing assessment scores within 30-60 days of initiation of treatment. As described above, the stimulation parameters may be programmed into the IPG, may be adjusted in the IPG responsive to (i) stimulation commands transferred from the activator or (ii) programming data transferred from the external programmer.

The stimulation parameters include, for example, pulse amplitude (voltage or current), pulse width, stimulation rate, stimulation frequency, ramp timing, cycle timing, session timing, and electrode configuration, including commands to start or stop a treatment session. In one embodiment, pulse amplitude is programmed to be adjustable between 0 and 7 mA. In a preferred embodiment, pulse amplitude is programmed to be between about 2-5 mA, 2.5-4.5 mA, or 3-4 mA, and preferably about 3.5 mA. In one embodiment, pulse width is programmed to be adjustable between 25 and 500 µs. In a preferred embodiment, pulse width is programmed to be between about 100-400 µs, 150-350 µs, or 200-300 µs, and preferably about 350 µs. In one embodiment, stimulation rate is programmed to be adjustable between 1 and 40 Hz. In a preferred embodiment, stimulation rate is programmed to be between about 5-35 Hz, 10-30 Hz, or 15-20 Hz, and preferably about 20 Hz. In one embodiment, on ramp timing is programmed to be adjustable between 0 and 5 s. In a preferred embodiment, on ramp timing is programmed to be between about 0.5-4.5 s, 1-4 s, 1.5-3.5 s, or 2-3 s, and preferably about 2.5 s. In one embodiment, off ramp timing is programmed to be adjustable between 0 and 5 s. In a preferred embodiment, off ramp timing is programmed to be between about 0.5-4.5 s, 1-4 s, 1.5-3.5 s, or 2-3 s, and preferably about 2.5 s. In one embodiment, cycle-on timing is programmed to be adjustable between 2 and 20 s. In a preferred embodiment, cycle-on timing is programmed to be between about 4-18 s, 6-16 s, 8-14 s, 9-13 s, or 10-12 s and preferably about 10 s. In one embodiment, cycle-off timing is programmed to be adjustable between 20 and 120 s. In a preferred embodiment, cycle-off timing is programmed to be between about 30-110 s, 40-100 s, 50-90 s, 55-85 s, 60-80 s, or 65-75 s and preferably about 70 s. In one embodiment, session timing is programmed to be adjustable between 1 and 60 min. In a preferred embodiment, session timing is programmed to be between about 5-55 min, 10-50 min, 15-45 min, 20-40 min, or 25-35 min, and preferably about 30 min.

Figure 8:
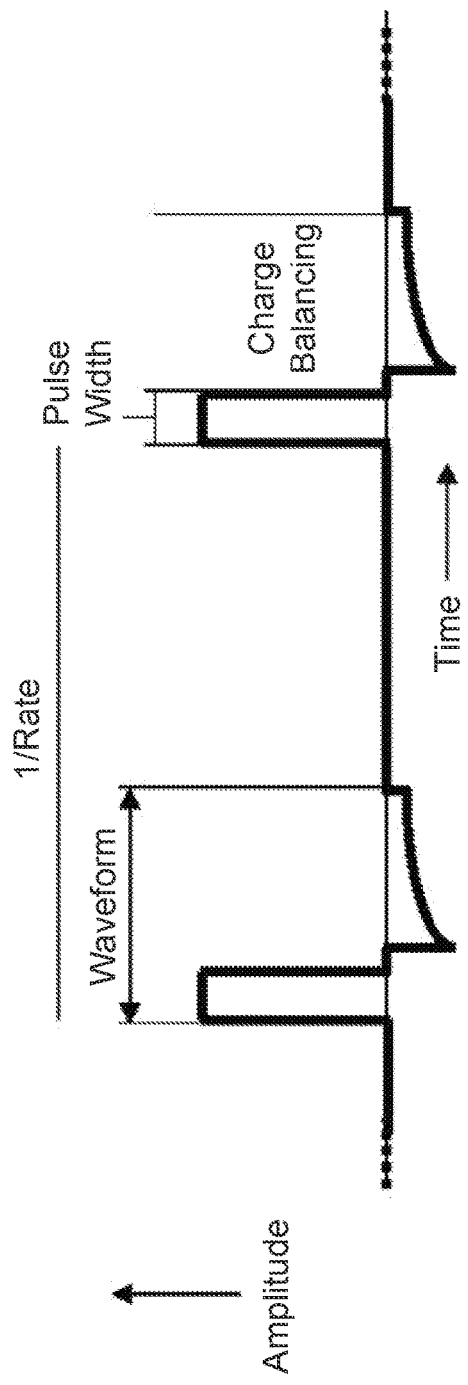
FIG. 8 shows a graph depicting an exemplary charge-balanced electrical stimulation waveform that may be delivered by the electrodes and IPG of the present invention.

FIG. 8 is a graph of an exemplary charge-balanced electrical stimulation waveform that may be delivered by the electrodes and IPG of the present invention. The IPG directs the electrodes, responsive to programming, stimulation commands, and/or received programming data, to stimulate at a pulse amplitude for the time of a pulse width and then balances the charge by dropping to a negative pulse amplitude and then bringing the pulse amplitude back to zero over the time of a waveform. The stimulation may be current-controlled and charge-balanced, or voltage-controlled and charge-balanced.

Figure 9:
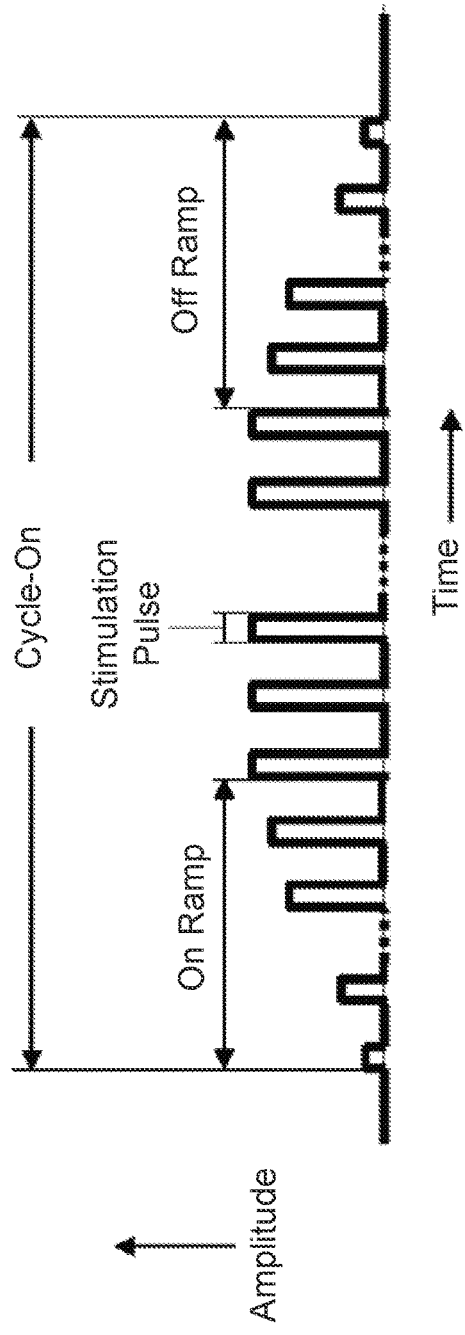
FIG. 9 shows a graph depicting an exemplary stimulation pulse train that may be delivered by the electrodes and IPG of the present invention.

FIG. 9 is a graph showing an exemplary stimulation pulse train that may be delivered by the electrodes and IPG of the present invention. During cycle-on programming, the IPG directs the electrodes, responsive to programming, stimulation commands, and/or received programming data, to deliver a stimulation pulse train in an "on ramp" manner such that the pulse amplitude increases in predetermined increments to reach the programmed peak pulse amplitude. In this way, the number of pulses in the "on ramp" needed to reach the programmed peak pulse amplitude may be determined by the IPG responsive to data supplied by the programming system. After reaching the programmed peak pulse amplitude, the IPG directs the electrodes to deliver at the programmed peak pulse amplitude for a predetermined number of stimulation pulses. After the predetermined number of stimulation pulses is reached, the IPG directs the electrodes, responsive to programming, stimulation commands, and/or received programming data, to deliver a stimulation pulse train in an "off ramp" manner such that the pulse amplitude decreases in predetermined increments from the programmed peak pulse amplitude to zero. As shown in FIG. 9, the pulse amplitude may drop, e.g., to zero, between each stimulation pulse.

Figure 10:
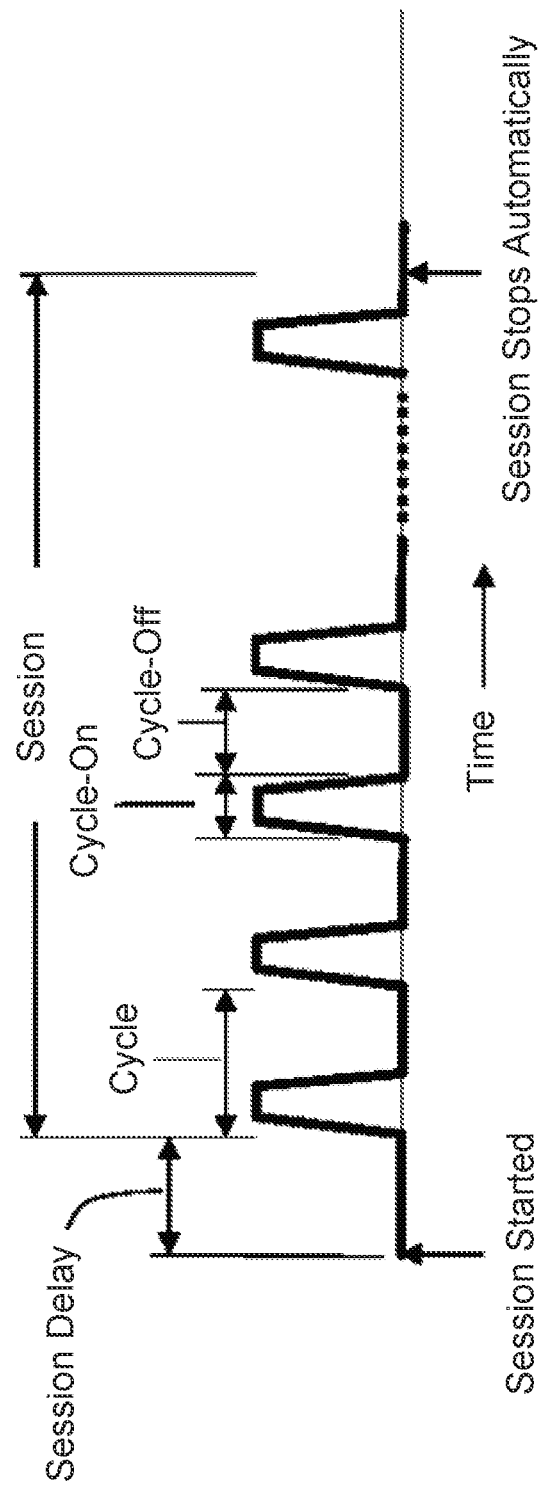
FIG. 10 shows a graph depicting an exemplary session that may be delivered by the electrodes and IPG of the present invention.

FIG. 10 is a graph showing an exemplary session that may be delivered by the electrodes and IPG of the present invention. In this example, during a cycle, the IPG directs the electrodes, responsive to programming, stimulation commands, and/or received programming data, to deliver electrical stimulation for the cycle-on duration, followed by a cycle-off duration of no electrical stimulation. Illustratively, a session is a programmable duration of repetitive cycles and the session delay is the time delay between the receipt of the command by the IPG to start a session to the start of the first cycle. After a session is completed, IPG directs the electrodes, responsive to programming, stimulation commands, and/or received programming data, to stop delivering electrical stimulation until a new session begins.

Figure 11:
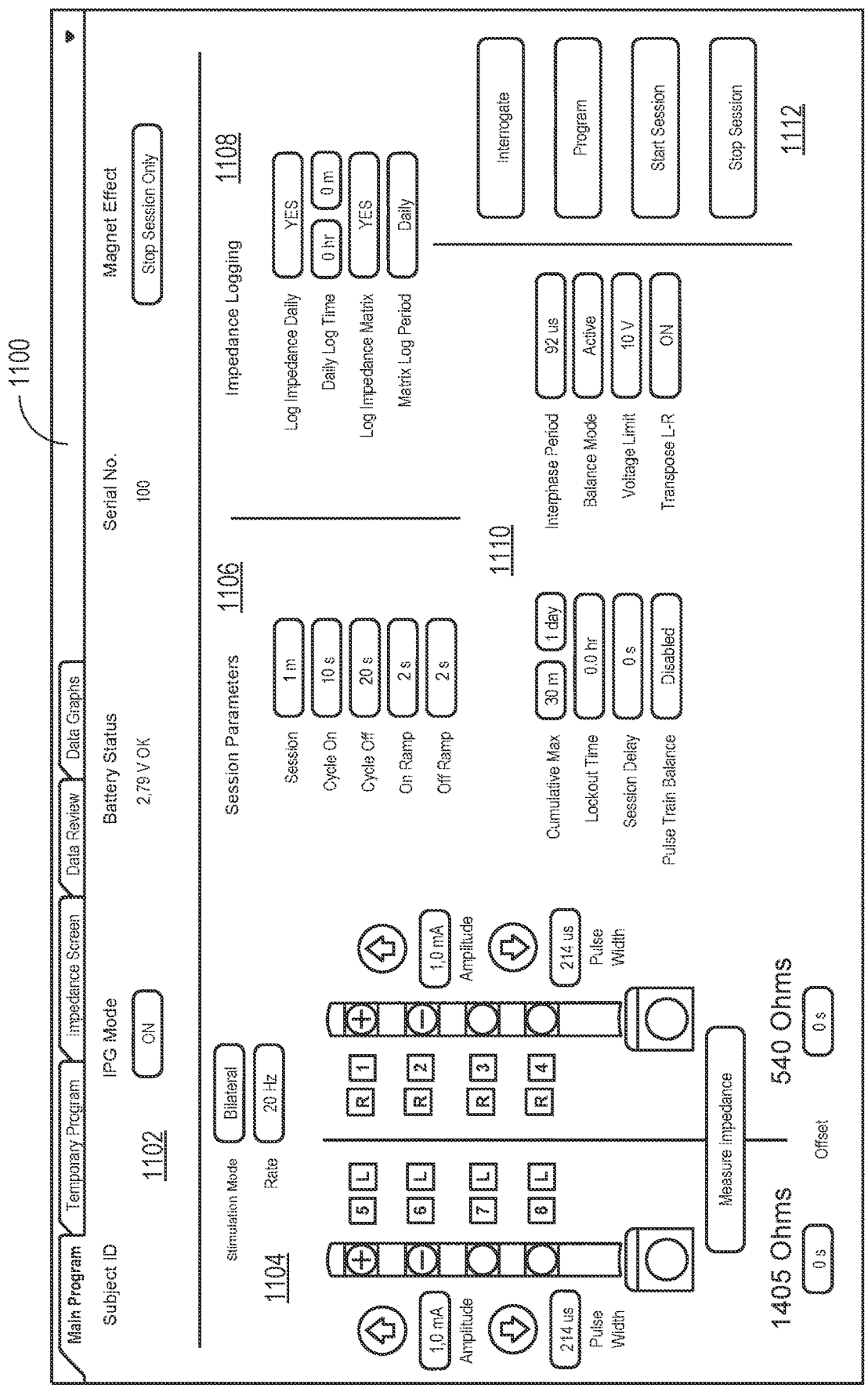
FIGS. 11-15 are exemplary screenshots illustrating various aspects of the user interface of the software-based programming system of the present invention.

Referring now to FIGS. 11-15, exemplary screen shots generated by user interface block 610 of software 600 are described for a stimulator system. FIG. 11 shows main program screen 1100 that is displayed to a physician running software-based programming system 600. Main program screen 1100 includes identification and status area 1102, electrode configuration area 1104, session parameters area 1106, impedance logging area 1108, settings area 1110, and buttons 1112.

In FIG. 11, identification and status area 1102 includes Subject ID, IPG Mode, Battery Status, Serial No., and Magnet Effect. Subject ID permits a user, e.g., a physician, to enter an ID, which is then displayed, for a subject having implanted electrodes and an IPG of the present invention. IPG Mode permits a user to turn the mode "ON", such that the IPG implanted in the subject is activated, and turn the mode "OFF", such that the IPG is deactivated. Battery Status displays the remaining battery power of the power supply in the IPG. Battery Status may be updated after a user interrogates the IPG to request updated battery status information. Serial No. displays the serial number assigned to the IPG implanted in the subject. Magnet Effect permits a user change how the IPG responds to sensing a magnetic field from a magnet, e.g., magnet 450. For example, a user may select "Stop Session Only", such that the IPG will only stop a stimulation session upon sensing the magnet; the user may select "Start Session Only", such that the IPG will only start a stimulation session upon sensing the magnet; the user may select "Start and Stop Session", such that the IPG will interchangeably stop or start a stimulation session each time the magnet is sensed; or the user may select "No Effect", such that the IPG does not respond to sensing the magnet.

Electrode configuration area 1104 includes Stimulation Mode, Rate, right electrode lead display, left electrode lead display, Amplitude, Pulse Width, Impedance area, and Offset. Stimulation Mode permits a user to select a "Bilateral" mode where electrodes on two separate electrode leads stimulate tissue at the same time or a "Unilateral" mode where electrodes on only one electrode lead stimulate tissue. Rate permits a user to select a stimulation rate of any integer between, e.g., 1-40 Hz. Right electrode lead display shows an illustration of four electrodes (numbered 1-4) on the right electrode lead implanted within the subject while left electrode lead display shows the four electrodes (numbered 5-8) on the left electrode lead implanted within the subject. A user may select which electrode(s) stimulate in a session and may change the polarity of each electrode between positive and negative. In the illustrated embodiment, when a session begins, negative electrode 2 on the right lead and negative electrode 6 on the left lead transmit energy to target tissue to stimulate the tissue and positive electrodes 1 and 5, respectively, receive the energy after it has passed through the target tissue. Amplitude permits a user to adjust the pulse amplitude delivered by an electrode on a lead. A user may increase the pulse amplitude by selecting the Amplitude button and then pressing the corresponding up arrow button and decrease by pressing the corresponding down arrow button for the right or the left electrode lead. In one embodiment, the pulse amplitude increases or decreases by 0.1 mA when the corresponding arrow button is pressed by a user. Alternatively, a user may enter in the desired pulse amplitude using, for example, the keyboard on the computer. Pulse Width permits a user to adjust the pulse width delivered by an electrode on a lead. A user may increase the pulse width by selecting the Pulse Width button and then pressing the corresponding up arrow button and decrease by pressing the corresponding down arrow button for the right or the left electrode lead. In one embodiment, the pulse width increases or decreases by 1 µs when the corresponding arrow button is pressed by a user. Alternatively, a user may enter in the desired pulse width using, for example, the keyboard on the computer. Impedance area permits a user to select the Measure Impedance button which causes the programming system, via the external programmer, to command the IPG to run the routine to measure impedances and then transmit the measured impedances back to the programming system, via the external programmer. The measured impedances then are displayed for each electrode. Offset permits a user to offset the stimulation timing between the right and left electrodes.

Session parameters area 1106 includes Session, Cycle On, Cycle Off, On Ramp, and Off Ramp. The corresponding button for each of the parameters permits a user to adjust the timing for each parameter by selecting the button and then pressing the up or down arrows, or, alternatively, by selecting the corresponding button and entering the desired parameter using, for example, the keyboard on the computer.

Impedance logging area 1108 includes Log Impedance Daily, Daily Log Time, Log Impedance Matrix, and Matrix Log Period. Log Impedance Daily includes a button that permits a user to select "YES" or "NO". If a user selects "YES", the IPG will run the impedance test routine every day and store the measured impedance in its memory for transfer to the programming system software. Daily Log Time permits a user to adjust how many hours and minutes per day the IPG will log the measured impedance. Log Impedance Matrix permits a user to select "YES", where the IPG will store the measured impedance in matrix form, and "NO" where the IPG will not store the measured impedance in matrix form. Matrix Log Period permits a user to select "Hourly", "Daily", or "Weekly", whereby the IPG will store the measured impedance in a matrix every hour, every day, or every week, respectively.

Settings area 1110 includes Cumulative Max, Lockout Time, Session Delay, Pulse Train Balance, Interphase Period, Balance Mode, Voltage Limit, and Transpose L-R. Cumulative Max permits a user to select the maximum cumulative stimulation session minutes in an amount of days. Lockout Time permits a user to set a number of hours or minutes that a stimulation session may not be initiated. Session Delay permits a user to select a number of seconds that a session will be delayed after IPG receives a command to start a session. Pulse Train Balance permits a user to cause a pulse train balance mode to be "Enabled" or "Disabled". The pulse train balance mode may be the mode described above with respect to FIG. 9. Interphase Period permits a user to adjust the time between stimulation pulses. Balance Mode permits a user to cause a balance mode to be "Active" or "Inactive". The balance mode may be the mode described above with respect to FIG. 8. Voltage Limit permits a user to adjust the maximum voltage that may be supplied from the power source to the electrodes. In one embodiment, Voltage Limit may be set to "Automatic" such that the controller of the IPG determines the maximum voltage based on predetermined thresholds programmed therein. Transpose L-R permits a user to turn "ON" or "OFF" a mode that, when activated, causes stimulation to be interchanged between the electrodes on the right electrode lead and the electrodes on the left electrode lead.

Buttons 1112 include Interrogate, Program, Start Session, and Stop Session. When pressed, the "Interrogate" button causes the communications circuitry in the external programmer to transmit interrogation commands, such as requests for the (i) actual value of stimulation parameter(s) programmed in the IPG, (ii) battery voltage remaining in the IPG, (iii) data logged in the IPG, and (iv) IPG status data, to the communications circuitry in the IPG for processing by the IPG controller. The responsive data is then sent back to the software, via communications circuitry in the IPG and external programmer, for display on the user interface of the computer, such as main program screen 1100. The "Program" button, when pressed, causes the communications circuitry in the external programmer to transmit programming data to the communications circuitry in the IPG for processing by the IPG controller. Programming data may include, for example, adjustments made by the user to the various input areas in main program screen 1100. The "Start Session" button, when pressed, causes the communications circuitry in the external programmer to transmit a command to begin a treatment session, or optionally programming data that includes such a command, to the communications circuitry in the IPG at the selected stimulation parameters for processing by the IPG controller. The stimulation parameter data may be stored in the IPG controller such that future sessions will cause stimulation at the selected stimulation parameters. The "Stop Session" button, when pressed, causes the communications circuitry in the external programmer to transmit a command to stop a treatment session to the communications circuitry in the IPG for processing by the IPG controller.

Figure 12:
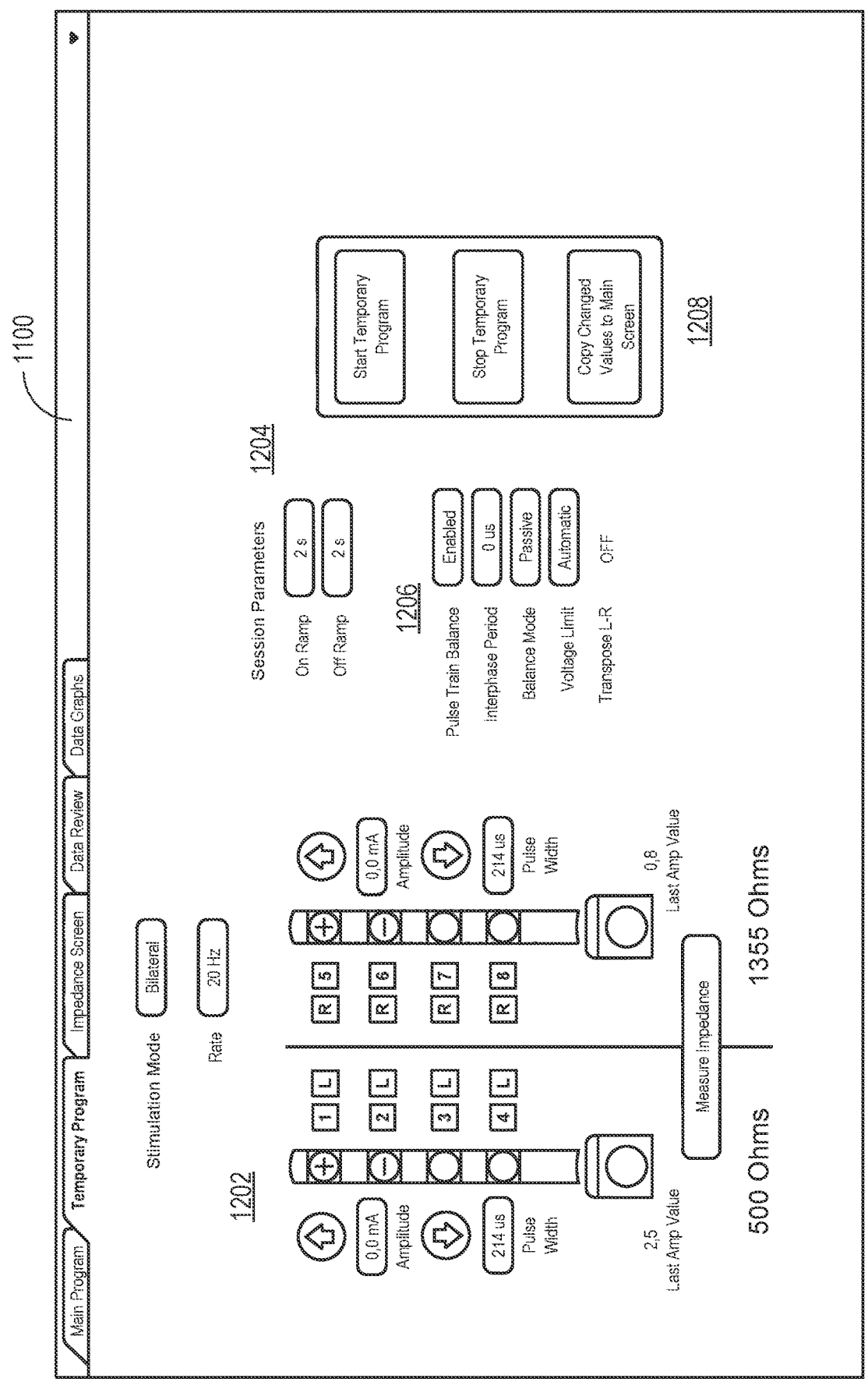

FIG. 12 shows temporary program screen 1200 that is displayed to a physician running software-based programming system 600. Temporary program screen 1200 includes electrode configuration area 1202, session parameters area 1204, settings area 1206, and buttons 1208. Temporary program screen 1200 permits a user to adjust stimulation parameters on a temporary basis, e.g., for one or two sessions.

Electrode configuration area 1202 is similar to electrode configuration area 1104 of FIG. 11 and for conciseness, will not be described again in detail. Session parameters area 1204 is similar to session parameters area 1106 of FIG. 11, although session parameters area 1204 may include fewer parameters for user adjustment. Illustratively, session parameters area 1204 includes On Ramp and Off Ramp.

Settings area 1206 is similar to settings area 1110 of FIG. 11, although settings area 1206 may include fewer settings for user adjustment. Illustratively, settings area 1206 includes Pulse Train Balance, Interphase Period, Balance Mode, Voltage Limit, and Transpose L-R.

Buttons 1208 include Start Temporary Program, Stop Temporary Program, and Copy Changed Values to Main Screen. The "Start Temporary Program" button, when pressed, causes the communications circuitry in the external programmer to transmit a command to begin a treatment session to the communications circuitry in the IPG at the selected temporary stimulation parameters for processing by the IPG controller. The temporary stimulation parameter data may be stored in the IPG controller on a temporary basis such that future sessions will cause stimulation at the stimulation parameters programmed prior to receipt of the temporary stimulation parameters. The "Stop Temporary Program" button, when pressed, causes the communications circuitry in the external programmer to transmit a command to stop a treatment session to the communications circuitry in the IPG for processing by the IPG controller. The "Copy Changed Values to Main Screen" button, when pressed, causes software-based programming system 600 to copy the temporary stimulation parameters entered in screen 1200 into corresponding input areas in main program screen 1100 of FIG. 11.

Figure 13:
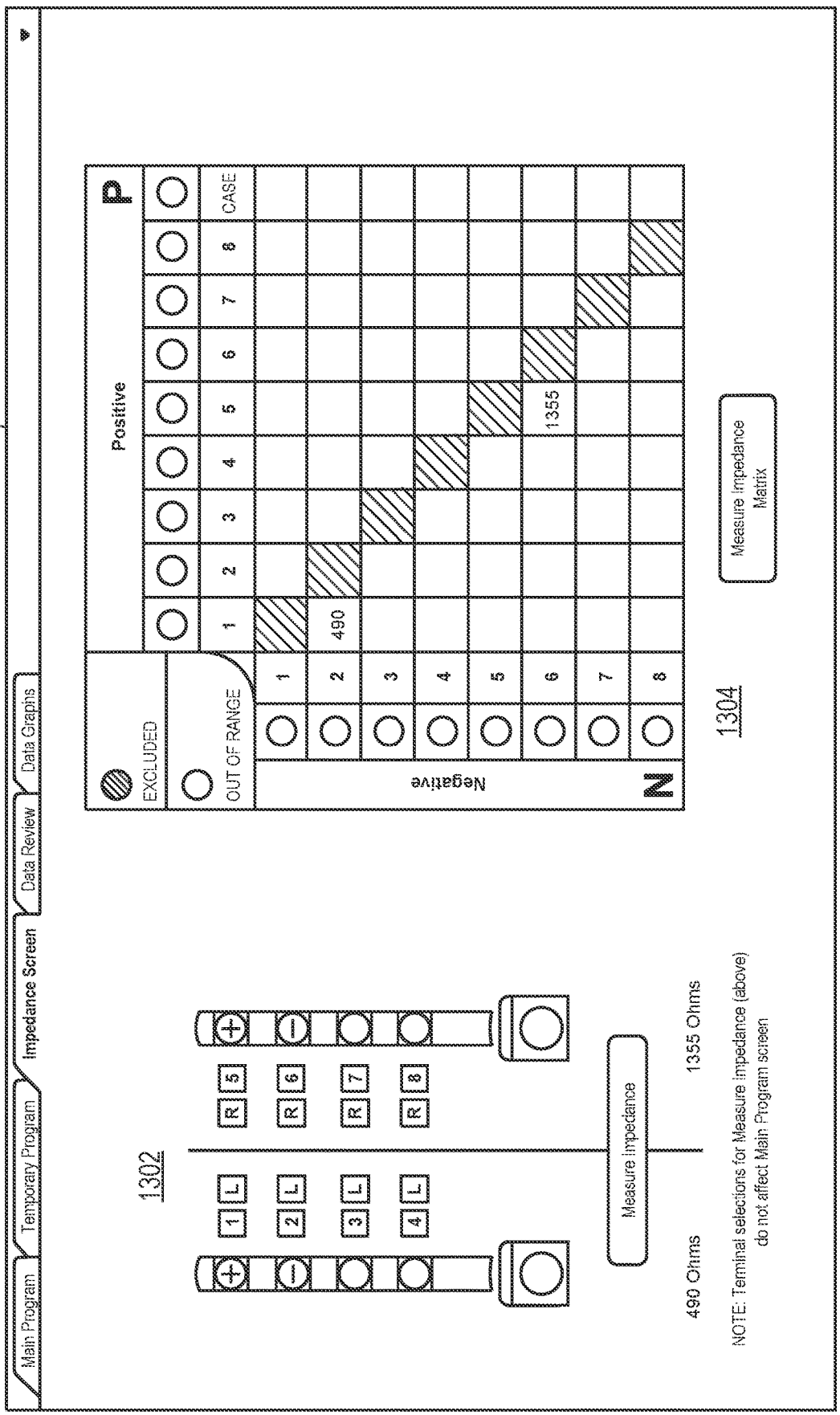

FIG. 13 shows impedance screen 1300 that is displayed to a physician running software-based programming system 600. Impedance screen 1300 includes electrode configuration area 1302 and impedance matrix area 1304.

Electrode configuration area 1302 includes right electrode lead impedance display, left electrode lead impedance display, and Impedance area. Right electrode lead impedance display shows an illustration of four electrodes (numbered 5-8) on the right electrode lead implanted within the subject while left electrode lead impedance display shows the four electrodes (numbered 1-4) on the left electrode lead implanted within the subject. A user may select at which electrode(s) to measure impedance using the respective displays. Impedance area permits a user to select the "Measure Impedance" button which causes the programming system, via the external programmer, to command the IPG to run the routine to measure impedances at the electrodes selected in the lead displays and then transmit the measured impedances back to the programming system, via the external programmer. The measured impedances then is displayed for each electrode. Selection of electrodes on the lead displays for measuring impedance does not affect electrode configuration area 1104 of main program screen 1100 in FIG. 11.

Impedance matrix area 1304 includes an impedance matrix and a Measure Impedance Matrix button. When pressed, the "Measure Impedance Matrix" button causes the impedance matrix to be populated with the measured impedances in accordance with selections made at electrode configuration area 1302. In the illustrated embodiment, impedance between electrode 2 (selected to be negative) and electrode 1 (selected to be positive) on the left lead is measured to be 490 Ohms and impedance between electrode 6 (selected to be negative) and electrode 5 (selected to be positive) on the right electrode lead is measured to be 1355 Ohms. Thus, when the Measure Impedance Matrix button is pressed, the software causes 490 to be populated at the intersection of 2 negative and 1 positive and 1355 to be populated at the intersection of 6 negative and 5 positive in the impedance matrix. The impedance matrix also may display when an electrode is excluded or out of range.

Figure 14:
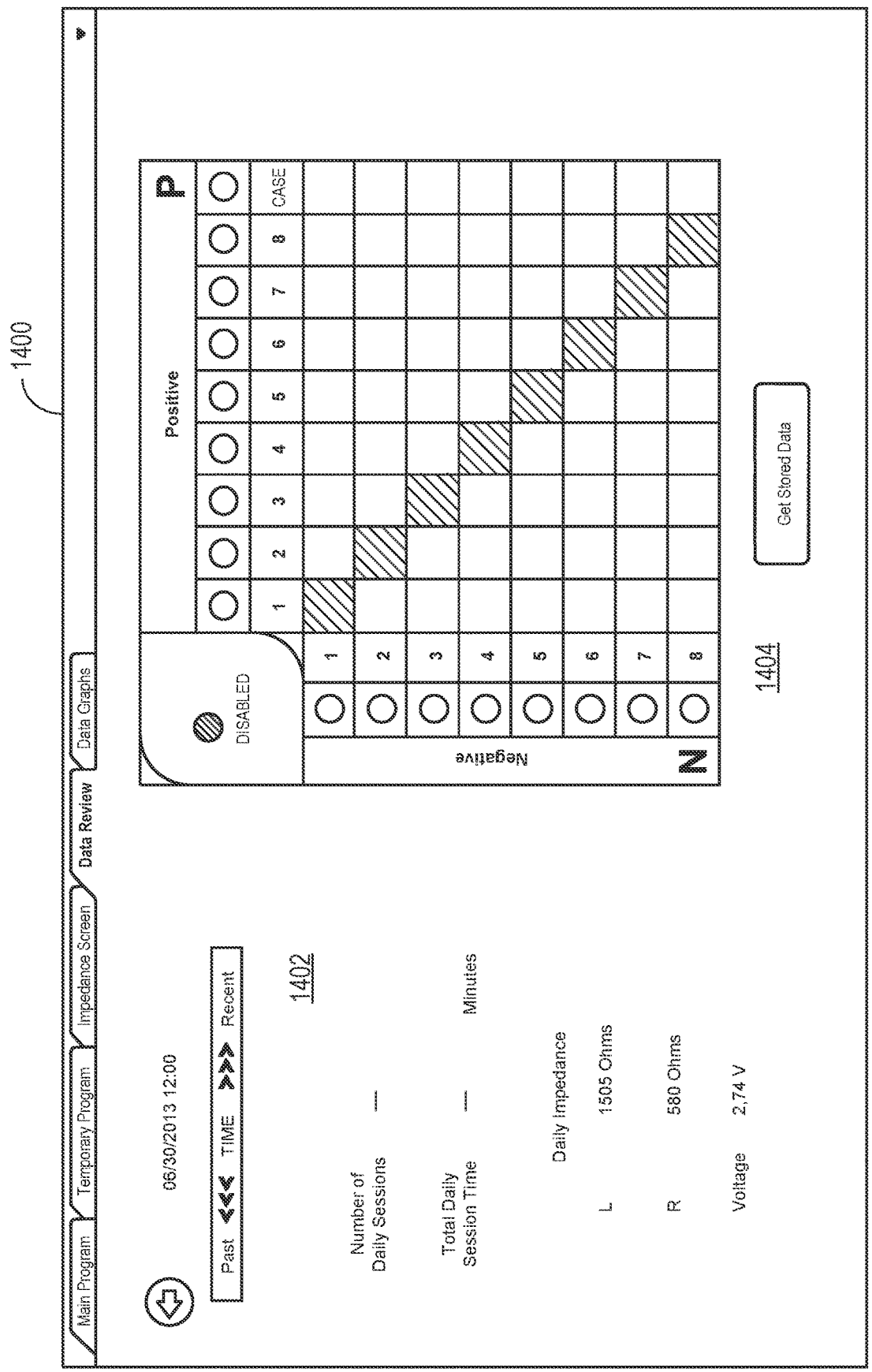

FIG. 14 shows data review screen 1400 that is displayed to a physician running software-based programming system 600. Data review screen 1400 includes daily log area 1402 and data matrix area 1404.

Daily log area 1402 permits a user to view, on a day-by-day basis, Number of Daily Sessions, Total Daily Session Time, Daily Impedance, and Voltage. The date button permits a user to select a day and time such that a user may view stored data from the selected day/time. The "Number of Daily Sessions" area displays the number of treatment sessions that were started for the selected day. The "Total Daily Session Time" area displays the number of minutes of treatment sessions for the selected day. The "Daily Impedance" area displays the measured impedance of the right and left electrode lead for the selected day. The "Voltage" area displays the measured voltage remaining in the IPG power supply at the end of the selected day.

Data matrix area 1404 includes a data matrix and a "Get Stored Data" button. When pressed, the "Get Stored Data" button, causes the communications circuitry in the external programmer to transmit a request for stored data to the communications circuitry in the IPG for processing by the IPG controller. The IPG controller retrieves the stored data from its memory and causes the communications circuitry in the IPG to transmit the stored data to the communications circuitry in the external programmer for display on data review screen 1400. The data matrix is populated with received stored data in the appropriate row and column corresponding to the electrode configuration. The data matrix also may display when an electrode is disabled.

Figure 15:
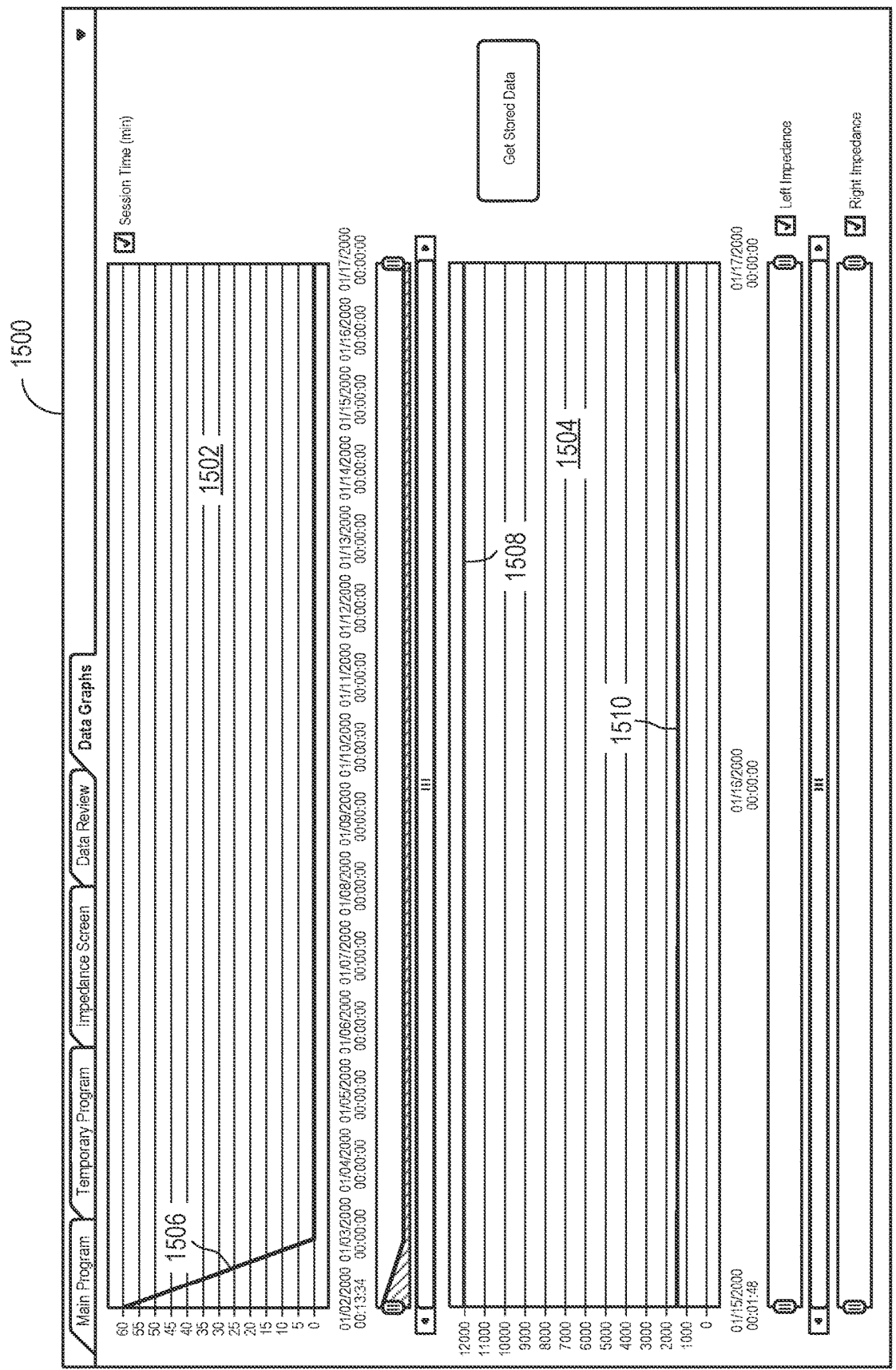

FIG. 15 shows data graphs screen 1500 that is displayed to a physician running software-based programming system 600. Data graphs screen 1500 includes session time graph 1502 and impedance graph 1504. Session time graph 1502 displays the total daily session time on a daily basis, as retrieved from stored data in the IPG. In the illustrated embodiment, session time 1506 shows that the patient used the stimulation system for 60 minutes on the first day and then did not use the stimulation system for the next 15 days. Impedance graph 1504 displays the daily impedance for the right and left electrode lead on a daily basis, as retrieved from stored data in the IPG. In the illustrated embodiment, right impedance 1508 shows that the measured impedance for the electrodes on the right electrode lead was about 12,000 ohms over three days, while left impedance 1510 shows that the measured impedance for the electrodes on the left electrode lead was about 1400 ohms over three days. When pressed, the "Get Stored Data" button, causes the communications circuitry in the external programmer to transmit a request for stored data to the communications circuitry in the IPG for processing by the IPG controller. The IPG controller retrieves the stored data from its memory and causes the communications circuitry in the IPG to transmit the stored data to the communications circuitry in the external programmer for display on data graphs screen 1500.

As will be readily understood by one of ordinary skill in the art, a user may enter data into the user interface using suitable mechanisms known in the art, such as, entering numbers, letters, and/or symbols via a keyboard or touch screen, mouse, touchpad, selection from a drop-down menu, voice commands, or the like.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A system for alleviating or reducing low back pain in a patient, the system comprising:
    a first electrode and a second electrode configured to be implanted bilaterally on either side of a lumbar spine within a back of a patient experiencing low back pain to deliver electrical stimulation to tissue associated with one or more spine stabilizing muscles associated with local segmental control of the lumbar spine within the back of the patient;
    a pulse generator configured to be in electrical communication with the first and second electrodes, the pulse generator configured to be programmed to deliver the electrical stimulation to the tissue associated with the one or more spine stabilizing muscles via the first electrode to cause contraction of the one or more spine stabilizing muscles to improve neuromuscular control system performance of the one or more spine stabilizing muscles and via the second electrode to reduce pain, thereby alleviating or reducing the patient's low back pain; and
    a first electrode lead and a second electrode lead configured to electrically couple the pulse generator to the first electrode and second electrode, respectively.

2. The system of claim 1, wherein the first and second electrodes are configured to be implanted to deliver the electrical stimulation to a dorsal ramus nerve that innervates a multifidus muscle.

3. The system of claim 1, wherein the first and second electrodes are configured to be implanted to deliver the electrical stimulation to a medial branch of the dorsal ramus nerve that innervates a multifidus muscle.

4. The system of claim 1, wherein the pulse generator is programmed to deliver the electrical stimulation to the tissue to alleviate or reduce the patient's back pain by improving neural control function of the one or more spine stabilizing muscles.

5. The system of claim 1, wherein the pulse generator is programmed to deliver the electrical stimulation at a stimulation rate selected in a range of 12-30 Hz.

6. The system of claim 1, wherein the pulse generator is configured to be implanted.

7. The system of claim 1, wherein the pulse generator is programmed to the deliver electrical stimulation to the tissue associated with the one or more spine stabilizing muscles at stimulation parameters titrated for the patient.

8. The system of claim 7, wherein the stimulation parameters comprises at least one of timing, magnitude, or duration of treatment.

9. The system of claim 1, wherein the first electrode lead and the second electrode lead each comprise a plurality of electrodes.

10. The system of claim 1, wherein each of the first electrode lead and second electrode lead comprises an anchor angled relative to the respective electrode lead.

11. A system for alleviating or reducing low back pain in a patient, the system comprising:
    first and second electrodes configured to be implanted bilaterally on either side of a lumbar spine within a back of a patient experiencing low back pain to deliver electrical stimulation to tissue associated with one or more spine stabilizing muscles associated with local segmental control of the lumbar spine within the back of the patient;
    a pulse generator configured to be in electrical communication with the first and second electrodes, the pulse generator configured to be programmed to deliver the electrical stimulation to the tissue associated with the one or more spine stabilizing muscles via the first electrode to improve neuromuscular control system performance of the one or more spine stabilizing muscles and via the second electrode to reduce pain, thereby alleviating or reducing the patient's low back pain; and
    a first electrode lead and a second electrode lead configured to electrically couple the pulse generator to the first electrode and second electrode, respectively,
    wherein the one or more spine stabilizing muscles comprises at least one of a multifidus, transverse abdominis, quadratus lumborum, psoas major, internus abdominis, obliquus externus abdominis, or erector spinae muscles.

12. The system of claim 11, wherein the pulse generator is programmed to deliver the electrical stimulation to the tissue to cause the one or more spine stabilizing muscles to contract.

13. A system for alleviating or reducing low back pain in a patient, the system comprising:
   first and second electrodes configured to be implanted bilaterally on either side of a lumbar spine within a back of a patient experiencing low back pain to deliver electrical stimulation to tissue associated with a multifidus muscle associated with local segmental control of the lumbar spine within the back of the patient;
   a pulse generator configured to be in electrical communication with the first and second electrodes, the pulse generator configured to be programmed to deliver the electrical stimulation to the tissue associated with the multifidus muscle via the first electrode to improve neuromuscular control system performance of the multifidus muscle and via the second electrode to reduce pain, thereby alleviating or reducing the patient's low back pain; and
   a first electrode lead and a second electrode lead configured to electrically couple the pulse generator to the first electrode and second electrode, respectively.

14. The system of claim 13, wherein the pulse generator is programmed to deliver the electrical stimulation to the tissue associated with the multifidus muscle to cause contraction of the multifidus muscle.

15. The system of claim 13, wherein the pulse generator is programmed to deliver the electrical stimulation to the tissue at a stimulation rate selected in a range of 12-30 Hz.

16. The system of claim 13, wherein the pulse generator is programmed to deliver the electrical stimulation to the tissue at a pulse width selected in a range of 20-500 µs.

17. The system of claim 13, wherein the pulse generator is programmed to deliver the electrical stimulation to the tissue at a pulse amplitude selected in a range of 0.1-7 mA.

18. The system of claim 13, wherein the pulse generator is programmed to deliver the electrical stimulation to the tissue at a stimulation rate selected in a range of 1-30 Hz, at a pulse width selected in a range of 20-500 µs, and at a pulse amplitude selected in a range of 0.1-7 mA.

19. The system of claim 13, wherein the pulse generator is programmed to deliver the electrical stimulation to the tissue adjunctive to a spine surgery intervention.

20. The system of claim 13, wherein the pulse generator is programmed to deliver electrical stimulation to the tissue associated with the one or more spine stabilizing muscles at stimulation parameters titrated for the patient.

21. The system of claim 20, wherein the stimulation parameters comprises at least one of timing, magnitude, or duration of treatment.

22. The system of claim 13, wherein the pulse generator is configured to be implanted.

23. The system of claim 13, wherein the first electrode lead and the second electrode lead each comprise a plurality of electrodes.

24. The system of claim 13, wherein each of the first electrode lead and second electrode lead comprises an anchor angled relative to the respective electrode lead.

25. The system of claim 24, wherein each of the first electrode lead and second electrode lead further comprises a second anchor proximal to the anchor, the anchor and the second anchor angled towards one another to anchor the respective electrode lead in a position for stimulating the tissue.

26. The system of claim 13, further comprising:
   an external programmer configured to transmit programming data to the pulse generator,
   wherein the pulse generator is programmed to deliver the electrical stimulation to the tissue consistent with the programming data.

27. The system of claim 13, further comprising:
   an activator configured to transmit a stimulation command to the pulse generator,
   wherein the pulse generator is programmed to deliver the electrical stimulation to the tissue responsive to the stimulation command.

28. A system for alleviating or reducing low back pain in a patient, the system comprising:
   first and second electrodes configured to be implanted bilaterally on either side of a lumbar spine within a back of a patient experiencing low back pain to deliver electrical stimulation to a dorsal ramus nerve that innervates a multifidus muscle which is associated with local segmental control of the lumbar spine within the back of the patient;
   a pulse generator configured to be in electrical communication with the first and second electrodes, the pulse generator configured to be programmed to deliver the electrical stimulation to the dorsal ramus nerve via the first electrode to cause the multifidus muscle to contract improve neuromuscular control system performance and via the second electrode to reduce pain, thereby alleviating or reducing the patient's low back pain;
   a first electrode lead and a second electrode lead configured to electrically couple the pulse generator to the first electrode and second electrode, respectively.

29. The system of claim 28, wherein the pulse generator is programmed to deliver the electrical stimulation to the tissue to alleviate or reduce the patient's back pain by improving neural control function of the multifidus muscle.

30. The system of claim 28, wherein the pulse generator is programmed to deliver the electrical stimulation at a stimulation rate selected in a range of 12-30 Hz.

* * * * *